(12) United States Patent (10) Patent No.: US 9,492,484 B2
Yeghiazarians et al. (45) Date of Patent: Nov. 15, 2016

(54) CARDIOSPHERE DERIVED CELL POPULATION AND METHODS OF USE

(71) Applicant: Regents of the University of California, Oakland, CA (US)

(72) Inventors: Yerem Yeghiazarians, Burlingame, CA (US); Jianqin Ye, San Francisco, CA (US); Andrew Boyle, San Francisco, CA (US); Kevin E. Healy, Berkeley, CA (US); Amit K. Jha, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 40 days.

(21) Appl. No.: 14/038,571

(22) Filed: Sep. 26, 2013

(65) Prior Publication Data

US 2014/0120066 A1 May 1, 2014

Related U.S. Application Data

(60) Provisional application No. 61/706,203, filed on Sep. 27, 2012.

(51) Int. Cl.
| | |
|---|---|
| C12N 5/00 | (2006.01) |
| C12N 5/02 | (2006.01) |
| A01N 63/00 | (2006.01) |
| A01N 65/00 | (2009.01) |
| A61K 35/34 | (2015.01) |
| C12N 5/077 | (2010.01) |

(52) U.S. Cl.
CPC ............. *A61K 35/34* (2013.01); *C12N 5/0657* (2013.01); *C12N 2533/80* (2013.01)

(58) Field of Classification Search
None
See application file for complete search history.

(56) References Cited

U.S. PATENT DOCUMENTS

| | | | | |
|---|---|---|---|---|
| 2009/0118423 | A1* | 5/2009 | Kumar et al. | 524/850 |
| 2010/0203021 | A1* | 8/2010 | Goumans et al. | 424/93.7 |
| 2012/0039857 | A1* | 2/2012 | Smith et al. | 424/93.7 |
| 2015/0352156 | A1 | 12/2015 | Jha et al. | |

FOREIGN PATENT DOCUMENTS

| | | | | |
|---|---|---|---|---|
| WO | WO 2010/019769 | * | 2/2010 | ............... B32B 3/26 |
| WO | 2014/113573 A1 | | 7/2014 | |
| WO | 2014/165513 A1 | | 10/2014 | |

OTHER PUBLICATIONS

Yea et al, Ultramicro., 108:1144-1147 (2008).*
Gerecht et al., PNAS, 104(27):11298-11303 (2007).*
Kim et al., J. Biomed. Mater. Res., 88A(4):967-975 (2009).*
Habib et al., Biomaterials 32:7514-7523 (2011).*
Kim et al., J. Mater. Sci. Mater. Med., 19:3311-3318 (2008).*
Lutoff et al., PNAS, 100(9):5413-5418 (2003).*
Gillette et al., Nature Mater., 7:636-640 (2008).*
Zheng et al., Biomater., 25:1339-1348 (2004).*
Tan et al., Biomater., 30:2499-2506 (2009).*
Balakrishnan et al., Biomater., 26:3941-3951 (2005).*
Lei et al., Biomater., 32:39-47 (2011).*
Paterson et al., Mater. Today, 13(1-2):14-22 (2010).*
Burdick et al., Adv. Mater., 23(12):H41-H56 (2011).*
Dahlmann et al., Biomater., 34:940-951 (2013).*
Messina et al., "Isolation and expansion of adult cardiac stem cells from human and murine heart," *Cir. Res.* 95(9):911-921, Oct. 2004. *Epub* Oct. 7, 2004.
Smith et al., "Regenerative potential of cardiosphere-derived cells expanded from percutaneous endomyocardial biopsy specimens," *Circulation*, 115(7):896-90, Feb. 2007. *Epub* Feb. 5, 2007.
Takamiya et al., "Identification and Characterization of a Novel Multipotent Sub-Population of Sca-1+ Cardiac Progenitor Cells for Myocardial Regeneration," PLoS One, Sep. 2011, 6(9):e25265. doi:10.1371/journal.pone.0025265 (11 pages).
Tang et al., "A novel two-step procedure to expand Sca-1+ cells clonally," Biochem Biophys Res Commun., 359(4):877-883, Aug. 2007. *Epub* Jan. 11, 2007.

* cited by examiner

*Primary Examiner* — Thomas J Visone
(74) *Attorney, Agent, or Firm* — Kilpatrick Townsend & Stockton LLP

(57) ABSTRACT

Provided herein are compositions and methods for isolating and culturing cardiac progenitor cells, and for improved transplantation.

26 Claims, 34 Drawing Sheets

1. Synthesis of AcHyA

2. Thiolated Heparin (Heparin-SH)

Fig. 19
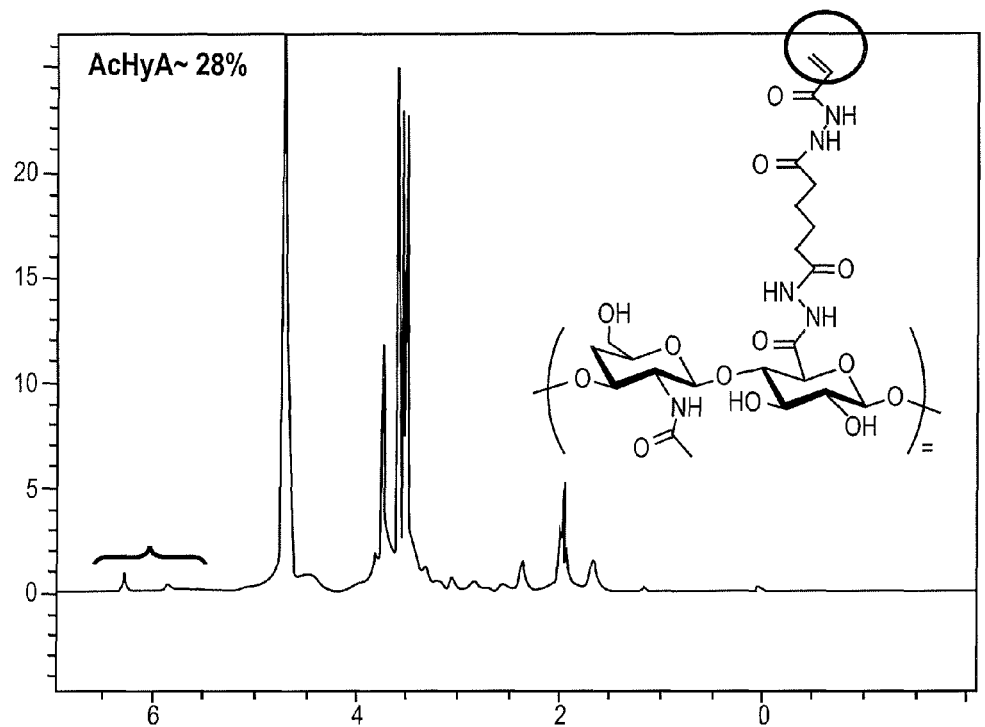
FIG. 19A
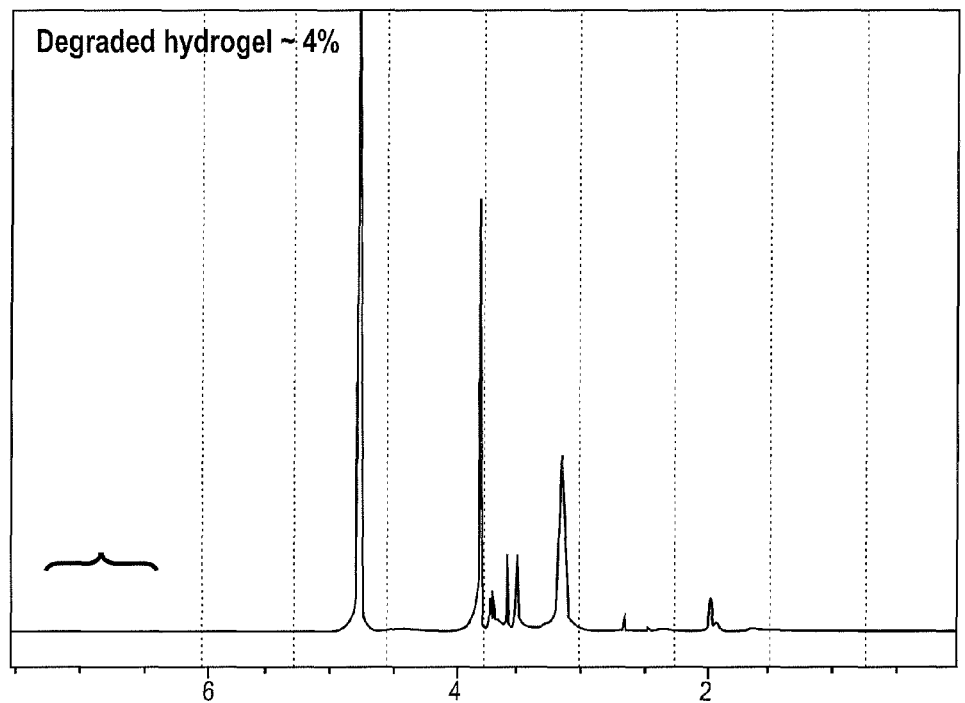
FIG. 19B

Fig. 19 (Cont.)
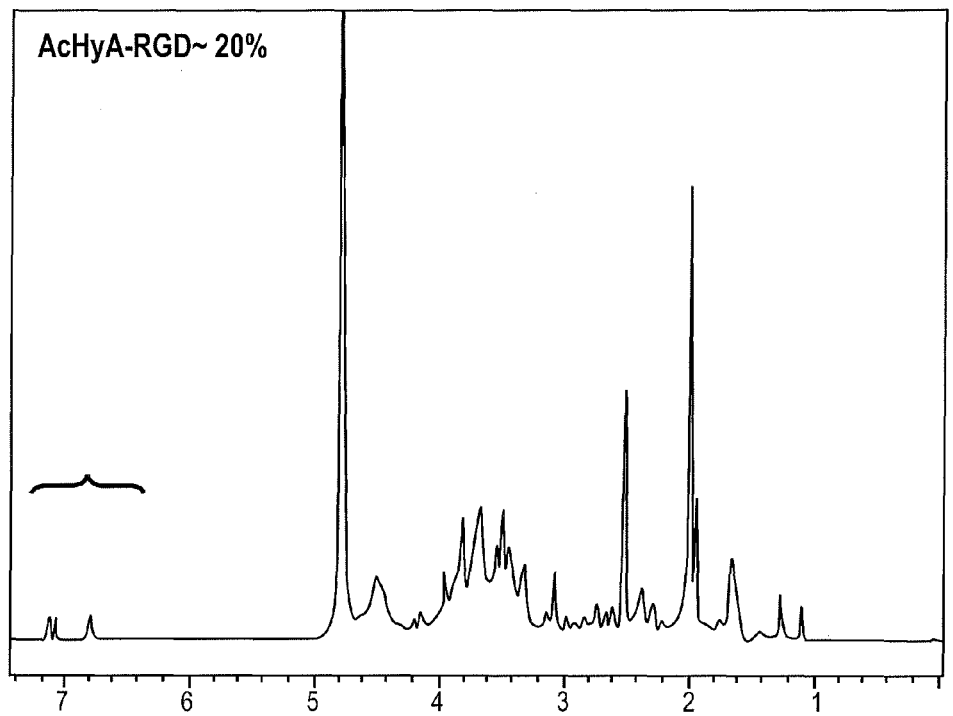
FIG. 19C
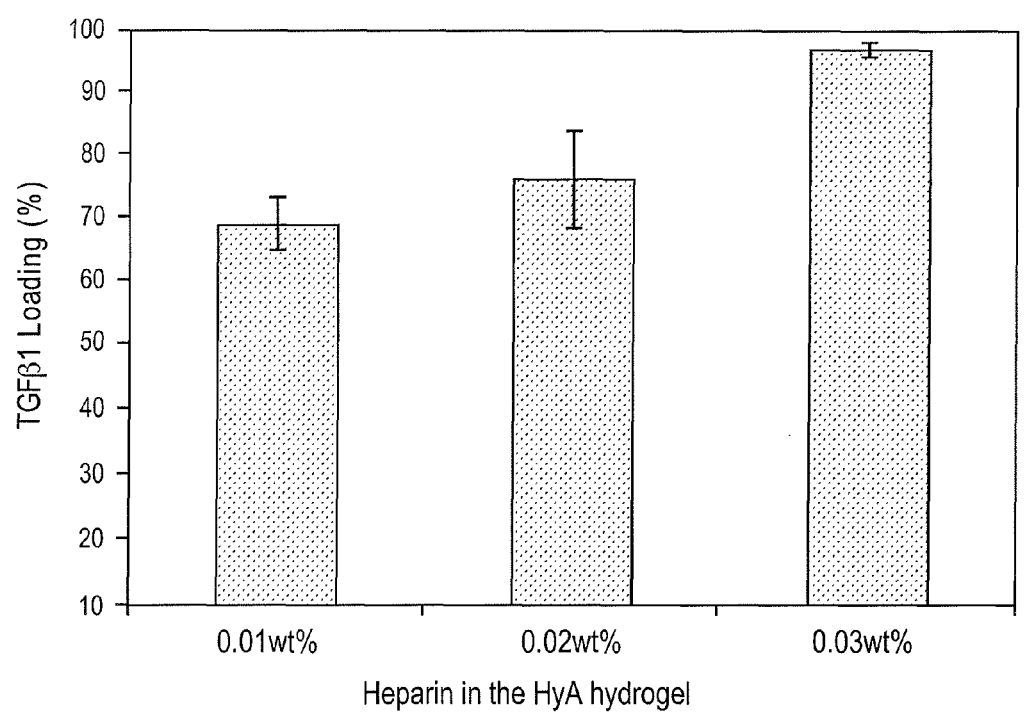
FIG. 19D

```
                          SEQUENCE LISTING

<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: synthetic adhesion peptide bsp-RGD, bspRGD(15)

<400> SEQUENCE: 1

Cys Gly Gly Asn Gly Glu Pro Arg Gly Asp Thr Tyr Arg Ala Tyr
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic adhesion peptide AG-10

<400> SEQUENCE: 2

Cys Gly Gly Asn Arg Trp His Ser Ile Tyr Ile Thr Arg Phe Gly
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: synthetic adhesion peptide LDVP

<400> SEQUENCE: 3

Cys Gly Gly Glu Ile Leu Asp Val Pro Ser Thr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: synthetic adhesion peptide AG73

<400> SEQUENCE: 4

Cys Gly Gly Arg Lys Arg Leu Gln Val Gln Leu Ser Ile Arg Thr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic adhesion peptide C16

<400> SEQUENCE: 5

Cys Gly Gly Lys Ala Phe Asp Ile Thr Tyr Val Arg Leu Lys Phe
1               5                   10                  15

<210> SEQ ID NO 6
<211> LENGTH: 12
<212> TYPE: PRT
<213> ORGANISM: Artificial Sequence
```

```
<220> FEATURE:
<223> OTHER INFORMATION: synthetic adhesion peptide P20

<400> SEQUENCE: 6

Arg Asn Ile Ala Glu Ile Ile Lys Asp Ile Gly Cys
 1               5                  10

<210> SEQ ID NO 7
<211> LENGTH: 18
<212> TYPE: PRT
<213> ORGANISM: Artificial Sequence
<220> FEATURE:
<223> OTHER INFORMATION: synthetic adhesion peptide P3

<400> SEQUENCE: 7

Cys Gly Gly Val Ser Trp Phe Ser Arg His Arg Tyr Ser Pro Phe Ala
 1               5                  10                  15

Val Ser

<210> SEQ ID NO 8
<211> LENGTH: 9
<212> TYPE: PRT
<213> ORGANISM: Artificial Sequence
<220> FEATURE:
<223> OTHER INFORMATION: synthetic MMP-13-17 cleavable peptide sequence,
      linker peptide

<400> SEQUENCE: 8

Cys Gln Pro Gln Gly Leu Ala Lys Cys
 1               5
```

CARDIOSPHERE DERIVED CELL POPULATION AND METHODS OF USE

CROSS-REFERENCES TO RELATED APPLICATIONS

This application claims priority to U.S. Provisional Appl. No. 61/706,203, filed Sep. 27, 2012, the disclosure of which is included by reference in its entirety.

STATEMENT AS TO RIGHTS TO INVENTIONS MADE UNDER FEDERALLY SPONSORED RESEARCH AND DEVELOPMENT

The invention was made with government support under Grant No. R01HL096525 awarded by the National Institutes of Health. The government has certain rights in this invention.

BACKGROUND OF THE INVENTION

REFERENCE TO A "SEQUENCE LISTING," A TABLE, OR A COMPUTER PROGRAM LISTING APPENDIX SUBMITTED AS AN ASCII TEXT FILE

The Sequence Listing written in file -2130-1.TXT, created on Nov. 12, 2013, 4,096 bytes, machine format IBM-PC, MS-Windows operating system, is hereby incorporated by reference in its entirety for all purposes.

According to the American Heart Association, an estimated 82.4 million American live with one or more types of cardiovascular disease. Annually, about 2.7% of Americans suffer a myocardial infarction (heart attack). Patients who survive acute myocardial infarction continue to suffer from loss of cardiomyocytes, cardiac scar formation, ventricular remodeling, and in most cases, eventual heart failure.

It has been discovered that a small population of cells in the adult heart have the capacity to self-renew and to differentiate into one or more cell types of the heart. It has been hypothesized that these cells can be used to repair or regenerate injured tissue. Thus, cell therapy holds much promise for treating cardiovascular disease.

BRIEF SUMMARY OF THE INVENTION

Provided herein are compositions of an isolated clonal population of cardiac progenitor cells wherein at least 3% (e.g., at least 3-10%, 15%, 25%, 30%, 50%, or more) of the cardiac progenitor cells express Isl1. In some aspects, at least 5% of the cardiac progenitor cells express Isl1. In some aspects, at least 10% of the cardiac progenitor cells express Isl1. In some aspects, about 3-10% of the cardiac progenitor cells express Isl1. In some aspects, about 50% of the cardiac progenitor cells express GATA4 and about 15% of the cells express NKX2.5. In some aspects, the cardiac progenitor cells are derived from a cardiospheres derived from injured heart tissue.

Provided herein are methods of obtaining a clonal population of cardiac progenitor cells, said method comprising (a) isolating a Sca-1 positive, CD45 negative cell from a cardiosphere derived from heart tissue; and (b) culturing the Sca-1 positive, CD45 negative cell to generate a clonal population of cardiac progenitor cells, wherein at least 3% of the cardiac progenitor cells express Isl1.

In some aspects, the cardiosphere is generated from cardiosphere-forming cells, wherein at least 5% of the cardiosphere-forming cells are Sca-1 positive, CD45 negative and at least 30% of the cardiosphere-forming cells are CD45 positive. In some aspects, the Sca-1 positive, CD45 negative cell expresses CD44, CD105, CD80, or combinations thereof. In some aspects, the culturing step of step (b) occurs for 7-30 days.

In some aspects, of the cardiac progenitors obtained by the method described herein, at least 5% of the cardiac progenitor cells express Isl1. In some aspects, at least 10% of the cardiac progenitor cells express Isl1. In some aspects, about 3-10% of the cardiac progenitor cells express Isl1. In some aspects, about 50% of the cardiac progenitor cells express GATA4 and about 15% of the cardiac progenitor cells express NKX2.5.

In some aspects, methods of obtaining a clonal population of cardiac progenitor cells further comprises administering the cardiac progenitor cells to a human subject. In some aspects, the subject has an injured heart, and the heart tissue is injured heart tissue from the subject. In some aspects, the injured heart is an infarcted heart. In some aspects, the injured heart is an ischemic heart. In some embodiments, the injured heart is a heart with heart failure.

In some aspects, administering the cardiac progenitor cells to the subject comprises injecting the cells into the infarcted heart tissue. In some aspects, administering the cardiac progenitor cells to the subject comprises injecting the cells into the ischemic heart tissue.

In some aspects, the subject has damaged blood vessels. In some aspects, administering the cardiac progenitor cells to the subject comprises injecting the cells at the site of the damaged blood vessels. In some aspects, the step of administering further comprises administering an angiogenesis promoting factor, wherein the angiogenesis promoting factor is IL-15, FGF, VEGF or angiopoietin.

Further provided are compositions of cardiac progenitor cells obtained by the methods of obtaining the cardiac progenitor cells as described herein.

Further provided are methods of treating a human subject with an injured heart, said method comprising administering cardiac progenitor cells to the injured heart, wherein at least 3% of the cardiac progenitor cells express Isl1. In some aspects, at least 5% of the cardiac progenitor cells express Isl1. In some aspects, at least 10% of the cardiac progenitor cells express Isl1. In some aspects, about 3-10% of the cardiac progenitor cells express Isl1. In some aspects, the cardiac progenitors are generated by (a) isolating the Sca-$1^+$CD45$^-$ cell from a cardiosphere derived from the injured heart of said subject; and (b) culturing Sca-$1^+$CD45$^-$ cell to generate cardiac progenitor cells (CPCs). In some embodiments, the Sca-$1^+$CD45$^-$ cells are cultured in a matrix comprising acrylated hyaluronic acid (AcHyA) to promote survival and differentiation prior to administering. In some embodiments, the matrix is directly or indirectly conjugated to (e.g., bound to or functionalized with) cysteine-terminating peptides. In some embodiments, the matrix is directly or indirectly conjugated to RGD peptides. In some embodiments, the matrix is directly or indirectly conjugated to heparin. In some embodiments, the Sca-$1^+$CD45$^-$ cells are cultured with TGFβ1.

In some aspects, administering comprises injecting the cardiac progenitor cells into the injured heart of said subject. In some aspects, the injured heart is an infarcted heart. In some aspects, the injured heart is an ischemic heart. In some embodiments, the injured heart is a heart with heart failure.

Provided herein are methods of stimulating angiogenesis in a subject in need thereof, said method comprising administering cardiac progenitor cells to the subject, wherein at least 3% of the cardiac progenitor cells express Isl1. In some aspects, the cardiac progenitors are generated by (a) isolating a Sca-1+CD45− cell from a cardiosphere derived from heart tissue of said subject; and (b) culturing the Sca-1+CD45− cell to generate cardiac progenitor cells. In some embodiments, the Sca-1+CD45− cell is cultured in a matrix comprising acrylated hyaluronic acid (AcHyA) to promote survival and differentiation prior to administering. In some embodiments, the matrix is directly or indirectly conjugated to (e.g., bound to or functionalized with) cysteine-terminating peptides. In some embodiments, the matrix is directly or indirectly conjugated to RGD peptides. In some embodiments, the matrix is directly or indirectly conjugated to heparin. In some embodiments, the Sca-1+CD45− cell is cultured with TGFβ1.

In some aspects, administering comprises injecting the cardiac progenitor cells (CPCs), optionally in the matrix, at the site of damaged blood vessels in the subject. In some aspects, the step of administering further comprises administering an angiogenesis promoting factor, wherein the angiogenesis promoting factor is IL-15, FGF, VEGF or angiopoietin.

Further provided are methods of promoting survival and differentiation of progenitor cells (e.g., CPCs, muscle progenitor cells, endothelial progenitor cells) comprising contacting Sca-1+CD45− cells with a matrix comprising acrylated hyaluronic acid (AcHyA), thereby supporting survival and differentiation of progenitor cells. In some embodiments, the progenitor cells are CPCs. In some embodiments, the method is practiced in in vitro culture. In some embodiments, the matrix is directly or indirectly conjugated to (bound to, functionalized with) cysteine-terminating peptides. In some embodiments, the matrix is directly or indirectly conjugated to (bound to, functionalized with) heparin. In some embodiments, the matrix is directly or indirectly conjugated to (bound to, functionalized with) RGD peptides. In some embodiments, the Sca-1+CD45− cells are obtained from heart tissue, e.g., injured heart tissue. In some embodiments, the Sca-1+CD45− cells are further contacted with TGFβ1. In some embodiments, the CPCs express Isl1 (e.g., at least 3%, 3-10%, 15%, 20%, 30%, 50% or more of the CPCs).

In some embodiments, the matrix and surviving and differentiated cells are administered to a subject, e.g., a human subject. In some embodiments, the administration is by injection to the affected area, e.g., to an injured or infarcted heart or to tissue in need of blood supply (e.g., hypoxic tissue). In some embodiments, the administration is to an autologous subject, and the progenitor cells are obtained from cardiospheres from heart tissue (e.g., injured or infarcted heart tissue) from the subject. In some embodiments, the administration is to an allogeneic subject, and the progenitor cells are obtained from cardiospheres from heart tissue (e.g., injured or infarcted heart tissue) from another subject.

Provided herein are methods of performing matrix-assisted cell transplantation (MACT) in a mammalian subject comprising contacting progenitor cells with a matrix comprising acrylated hyaluronic acid (AcHyA); culturing the progenitor cells to proliferate and differentiate; and administering the matrix and proliferated and differentiated cells to the mammalian subject. In some embodiments, the progenitor cells are Sca-1+CD45− cells. In some embodiments, the progenitor cells are obtained from cardiospheres from heart tissue, e.g., injured or infarcted heart tissue from the subject. In some embodiments, the administration is by injection to the affected area, e.g., to an injured or infarcted heart or to tissue in need of blood supply (e.g., hypoxic tissue). In some embodiments, the matrix is directly or indirectly conjugated to (bound to, functionalized with) cysteine-terminating peptides. In some embodiments, the matrix is directly or indirectly conjugated to (bound to, functionalized with) heparin. In some embodiments, the matrix is directly or indirectly conjugated to (bound to, functionalized with) RGD peptides. In some embodiments, the progenitor cells are cultured with TGFβ1.

Other objects, features, and advantages of the present invention will be apparent to one of skill in the art from the following detailed description and figures.

BRIEF DESCRIPTION OF THE DRAWINGS

FIG. 19: Validation of AcHyA components. Proton (1H) NMR spectra demonstrating the acrylate bound to (a) the AcHyA macromers and compared to (b) degraded hydrogel and (c) AcHyA-RGD. (d) Dependency on the percentage of TGFβ1 retained by the hydrogel on the weight percentage of incorporated heparin, as determined by ELISA.

DETAILED DESCRIPTION OF THE INVENTION

I. Introduction

Figure 1:
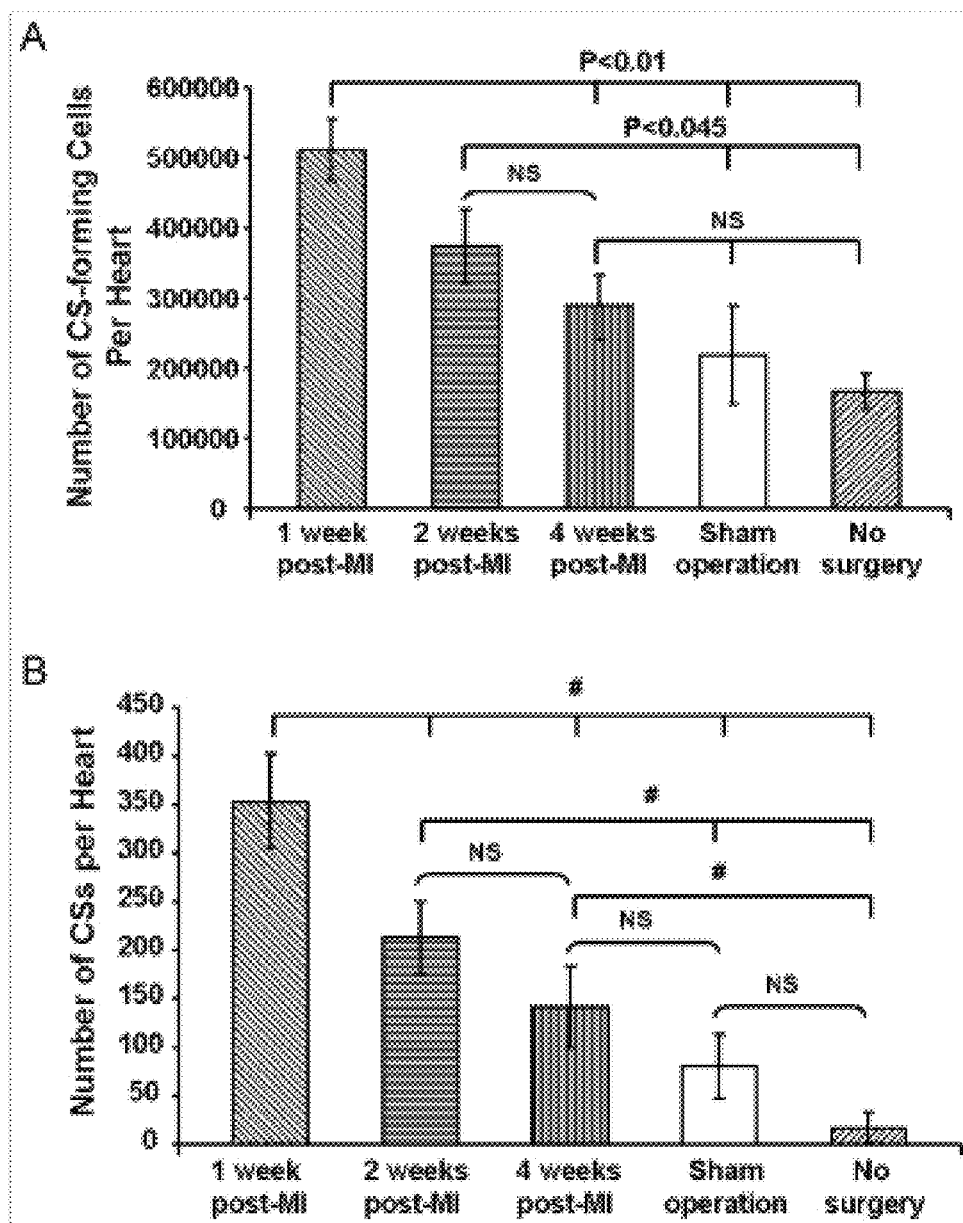
FIG. 1: Myocardial injury increases the production of CSs.

Provided herein are clonal populations of cardiac progenitor cells wherein a subset of the cells express Isl1. The cardiac progenitor cells have the capacity to expand and differentiate into cardiomyocytes, endothelial cells or smooth muscle cells. Further provided are methods of obtaining and expanding cardiac progenitor cells from a single Sca-1 positive, CD45 negative cells, and therapeutic uses thereof. Further provided are methods and compositions for effective transplantation of

II. Definitions

The following definitions are provided to facilitate understanding of certain terms used frequently herein and are not meant to limit the scope of the present disclosure.

As used herein, the following terms have the meanings ascribed to them unless specified otherwise.

The terms "derived from" when referring to cells or a biological sample (e.g., blood, tissue, bodily fluids, etc.) indicates that the cells were obtained from the stated source at some point in time. For example, a cell derived from an individual can represent a primary cell obtained directly from the individual (i.e., unmodified). In some instances, a cell derived from a given source undergoes one or more rounds of cell division and/or cell differentiation such that the original cell no longer exists, but the continuing cell (e.g., daughter cells from all generations) will be understood to be derived from the same source. The term includes directly obtained from, isolated and cultured, or obtained, frozen, and thawed.

The term "isolating" or "isolated" when referring to a cell or a molecule (e.g., nucleic acids or protein) indicates that the cell or molecule is or has been separated from its natural, original or previous environment. For example, an isolated cell can be removed from a tissue derived from its host individual, but can exist in the presence of other cells (e.g., in culture), or be reintroduced into its host individual.

The term "culturing" refers to growing cells or tissue under controlled conditions suitable for survival, generally outside the body (e.g., ex vivo or in vitro). The term includes "expanding," "passaging," "maintaining," etc. when referring to cell culture of the process of culturing. Culturing cells can result in cell growth, differentiation, and/or division.

The term "disaggregating" includes separating, dislodging, or dissociating cells or tissue using mechanical or enzymatic disruption to isolate single cells or small clusters of cells. In some instances, enzymatic disruption can be replaces with one of more enzyme alternatives having substantially the same effect as the enzyme.

The term "clonal" refers to a cell or a group of cells that have arisen from a single cell through numerous cycles of cell division. The cells of a clonal population are genetically identical. A clonal population can be a heterogenous population such that the cells can express a different set of genes at a specific point in time.

The term "progenitor cell" as used herein refers to a cell that has the capacity to differentiate into a specific type of cell, as well as replicate to generate a daughter cell substantially equivalent to itself. In some instances, a progenitor cell undergoes limited self-renewal such that it does not self-replicate indefinitely.

The term "self-renewal" or "self-renewing" refers to the ability of a cell to divide through numerous cycles of cell division and generate a daughter with the same characteristics as the parent cell. The other daughter cell can have characteristics different from its parent cell. The term includes the ability of a cell to generate an identical genetic copy of itself (e.g., clone) by cell division. For example, a self-renewing cardiac progenitor cell can divide to form one daughter cardiac progenitor cell and another daughter cell committed to differentiation to a cardiac lineage such as an endothelial, smooth muscle or cardiomyocyte cell. In some instances, a self-renewing cell does not undergo cell division forever.

The term "multipotent" refers to a cell having the potential to differentiate into multiple, yet a limited number of cell types or cell lineages. Typically, these cells are considered unspecialized cells that have the ability to self-renew and become specialized cells with specific functions and characteristics.

The term "endothelial cell" refers to a cell necessary for the formation and development of new blood vessel from pre-existing vessels (e.g., angiogenesis). Typically, endothelial cells are the thin layer of cells that line the interior surface of blood vessels and lymphatic vessels. Endothelial cells are involved in various aspects of vascular biology, including atherosclerosis, blood clotting, inflammation, angiogenesis, and control of blood pressure.

The term "smooth muscle cell" refers to a cell comprising non-striated muscle (e.g., smooth muscle). Smooth muscle is present within the walls of blood vessels, lymphatic vessels, cardiac muscle, urinary bladder, uterus, reproductive tracts, gastrointestinal tract, respiratory tract, and iris of the eye.

The term "cardiomyocyte cell" refers to a cell comprising striated muscle of the walls of the heart. Cardiomyocytes can contain one or more nuclei.

The term "cardiosphere" refers to a cluster of cells derived from heart tissue or heart cells. In some instances, a cardiosphere includes cells that express stem cell markers (e.g., c-Kit, Sca-1, etc.) and differentiating cells expressing myocyte proteins and the gap protein (connexin 43).

The term "positive" as used herein, refers to the presence of expression of a specific gene by a cell. For example, positive expression can correspond to the presence of RNA and/or protein encoded by a specific gene.

The term "negative" as used herein, refers to the absence of expression of a specific gene by a cell. For example, negative expression can correspond to the absence (e.g., undetectable presence) of RNA and/or protein encoded by a specific gene.

As used herein, the term "expression" or variants thereof to a gene refers to the generation of a transcriptional product (e.g., RNA) and/or translational product (e.g., protein) of said gene. The presence or level of RNA present in the cell or protein produced by the cell corresponds to the expression of the specific gene.

"Isl1" as referred to herein includes the islet-1 gene as well as RNA and protein encoded by the gene. Isl1 is a LIM homeodomain transcription factor. During fetal development, Isl1 is expressed in cells that give rise to the structures of the fetal heart including the vasculature. In some aspects, the Isl1 protein is a protein identified by the GenBank Accession No. NP_002193 and the corresponding RNA is identified by the GenBank Accession No. NM_002202.

"GATA4" as referred to herein includes the GATA4 gene as well as RNA and protein encoded by the gene. GATA4 is a zinc finger transcription factor. During fetal heart development, GATA4 protein regulates expression of genes involved in myocardial differentiation and function. In some aspects, the GATA4 protein is a protein identified by the GenBank Accession No. NP_002043 and the corresponding RNA is identified by the GenBank Accession No. NM_002052.

"NKX2.5" as referred to herein includes the NKX2.5 gene as well as RNA and protein encoded by the gene. NKX2.5 is a homeodomain transcription factor that regulates human heart formation. In some aspects, the NKX2.5 protein is a protein identified by the GenBank Accession No. NP_00437801 and the corresponding RNA is identified by the GenBank Accession No. NM_004387.

"Sca-1" as referred to herein includes a cell surface marker that is expressed on hematopoietic stem cells. Sca-1 positive cells are located in the adult bone marrow, fetal liver, mobilized peripheral blood and spleen in adults. Antibodies useful for the presently disclosed methods, and that recognize (e.g., bind to, are specific for, complex to) Sca-1 are commercially available from, for example, Abcam, eBioscience, Miltenyi Biotec, and R & D Systems.

"CD45" as referred to herein includes a lymphocyte common antigen that is also a receptor-linked protein tyrosine phosphatase. It is expressed on the surface of cells including leukocytes. Antibodies useful for the presently disclosed methods, and that recognize (e.g., bind to, are specific for, complex to) CD45 are commercially available from, for example, Abcam, Santa Cruz Biotechnology, Millipore, and R & D Systems.

The term "autologous" refers to deriving from or originating in the same subject or patient. An autologous transplant" refers to collection (e.g., isolation) and re-transplantation of a subject's own cells or organs. In some instances, an "autologous transplant" includes cells grown or cultured from a subject's own cells.

The term "allogeneic" refers to deriving from or originating in another subject or patient. An "allogeneic transplant" refers to collection (e.g., isolation) and transplantation of the cells or organs from one subject into the body of another. In some instances, an "allogeneic transplant" includes cells grown or cultured from another subject's cells.

The term "transplant", as used herein, refers to cells, e.g., cardiac progenitor cells, introduced into a subject. The source of the transplanted material include cultured cells, cells from another individual, or cells from the same individual (e.g., after the cells are cultured, enriched, or expanded ex vivo or in vitro).

The terms "treatment," "therapy," "amelioration" and the like refer to any reduction in the severity of symptoms. As used herein, the terms "treat" and "prevent" are not intended to be absolute terms. Treatment can refer to any delay in onset, amelioration of symptoms, improvement in patient survival, repair/regeneration of heart tissue or blood vessels, increase in survival time or rate, etc. The effect of treatment can be compared to an individual or pool of individuals not receiving the treatment. In some instances, the effect can be the same patient prior to treatment or at a different time during the course of therapy. In some aspects, the severity of disease, disorder or injury is reduced by at least 10%, as compared, e.g., to the individual before administration or to a control individual (e.g., healthy individual or an individual no longer having the disease, disorder or injury) not undergoing treatment. In some aspects, the severity of disease, disorder or injury is reduced by at least 20%, 25%, 50%, 75%, 80%, or 90%. In some cases, the symptoms or severity of disease are no longer detectable using standard diagnostic techniques.

The terms "subject," "patient," "individual" and the like are used interchangeably and refer to, except where indicated, mammals such as humans and non-human primates, as well as rabbits, rats, mice, dogs, cats, goats, pigs, cows, and other mammalian species. The term does not necessarily indicate that the subject has been diagnosed with a particular disease, but typically refers to an individual under medical supervision.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, $2^{nd}$ ed., J. Wiley & Sons (New York, N.Y. 1994); Sambrook et al., MOLECULAR CLONING, A LABORATORY MANUAL, $4^{rd}$ ed., Cold Springs Harbor Laboratory Press (Cold Spring Harbor, N.Y. 2012); Freshney R. I., CULTURE OF ANIMAL CELLS: A MANUAL OF BASIC TECHNIQUE AND SPECIALIZED APPLICATIONS, $6^{th}$ ed., J. Wiley & Sons (Hoboken, N.J. 2010). Any methods,

III. Compositions of Cardiac Progenitor Cells

In some aspects, provided herein are cell compositions of a population of cardiac progenitor cells (CPCs) derived from human heart tissue. In some aspects, provided herein are cardiac progenitor cells wherein at least 3%, 5%, 7%, 10%, 12%, or 15%, e.g., 3-50%, 3-20%, 3-10%, 5-30%, 5-10%, etc., of the cells express Isl1. In some aspects, CPCs comprise about 10%, 15%, 20%, 30%, 40%, or 50%, e.g., 10-50%, 10-40%, 10-30%, 15-40%, etc., GATA4 expressing cells. In some aspects, CPCs comprise about 5%, 8%, 10%, 13%, or 15%, e.g., 8-15%, 5-15%, 5-13%, etc., NKX2.5 expressing cells.

As described herein, CPCs are unmodified cells in that recombinant nucleic acids or proteins have not been introduced into them or the Sca-1+, CD45− cell from which it is derived. As such, CPCs are non-transgenic, or in other words have not been genetically modified. For example, expression of genes such as Isl1, GATA4, and NKX2.5 in CPCs is from the endogenous gene.

In some aspects, CPCs comprise Sca-1+, CD45− cells, c-kit+ cells, CD90+ cells, CD133+ cells, CD31+ cells, Flk1+ cells, GATA4+ cells, or NKX2.5+ cells, or combinations thereof. In some aspects, CPCs comprise about 50% GATA4 expressing cells. In some aspects, CPCs comprise about 15% NKX2.5 expressing cells.

The inventors have discovered that CPCs, as described herein, are self-renewing and multipotent cells. For instance, CPCs can replicate and are capable of differentiating into endothelial cells, cardiomyocytes, smooth muscle cells, and the like.

IV. Cell Culture Methods

The inventors have discovered that CPCs can be obtained, derived or generated from a single Sca-1+, CD45− cell isolated a cardiosphere derived from heart tissue. A single Sca-1+, CD45− cell can be expanded to generate a clonal population of CPCs, e.g., as described above. The inventors have also determined that CPCs can be derived from an injured heart, including an infarcted heart or an ischemic heart.

Methods of generating a cardiosphere, culturing heart tissue, culturing cardiosphere-derived cells are described in, e.g., Messina et al., *Circ res*, 95:911-921 (2004); Tan et al., "Isolation and Expansion of Cardiosphere-Derived Stem Cells", *Current Protocols in Stem Cell Biology*, Unit 2C.3, 2011; White et al., *Eur Heart Jour*, (2011).

Typically, heart tissue is collected from a patient during surgery or cardiac biopsy and harvested from the left ventricle, right ventricle, septum, left atrium, right atrium, or combinations thereof. The heart tissue can be taken from a patient and cultured directly. In other instances, the heart tissue can be frozen, thawed, and then cultured. The heart tissue can be cultured as an explant (e.g., ex vivo) such that cells including fibroblast-like cells and cardiosphere-forming cells grow out from the explant. In some instances, heart tissue is collected from a patient after cardiac injury and cultured on tissue culture plates coated with one or more components of the extracellular matrix (e.g., fibrobronectin, laminin, collagen, etc.). The heart tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy.

Cells surrounding the explant including cardiosphere-forming cells are collected and cultured under conditions to promote the formation of cardiospheres. In some aspects, the cells are cultured in cardiosphere growth medium comprising buffered media, amino acids, nutrients, serum or serum replacement, growth factors including but not limited to EGF and bFGF, cytokines including but not limited to cardiotrophin, and other cardiosphere promoting factors such as thrombin. In some instances, cardiosphere-forming cells are plated at an appropriate density necessary for cardiosphere formation, such as 100,000 cells/ml. Cardiospheres can appear about 7 days after cardiosphere-forming cells are plated.

A cardiosphere comprises Sca-1+, CD45− cells. Typically, a cardiosphere is a heterogenous mixture of cells formed by self-assembling into a spherical cluster. Cells in a cardiosphere can express cell surface markers such as, c-kit, CD44, CD80, CD90, CD105, CD133, CD34, Sca-1 and CD45, and cardiac markers such as Isl1, NR×2.5, and GATA4, and endothelial markers such as Flk1. In some instances, a cardiosphere include at least 5% Sca-1+, CD45− cells. The cardiosphere can also comprises at least 30% CD45+ cells. In some instances, the cardiosphere includes CD45+ cells, CD133+ cells, CD34+ cells, Flk1+ cells, CD31+ cells, Isl1+ cells, Nkx2.5+ cells, or GATA4+ cells, or combinations thereof.

A Sca-1+, CD45− cell can be isolated from the heterogeneous mixture of cells in the cardiosphere using standard tissue culture and cell isolation methods. The cardiosphere can be disaggregated to generate a single cell suspension (e.g., mixture of single, isolated cells) using mechanical disruption or enzymes such as collagenase, protease, or variants thereof. Methods such as fluorescence-activated cell sorting (FACS sorting) and magnetic-activated cell sorting are useful for isolating the Sca-1+, CD45− cell. For instance, as described in Example 1, antibodies to CD45, Sca-1 and other cell surface antigens expressed by cells of the cardiosphere can be used to identify and isolate the desired Sca-1+, CD45− cell. Using a FACS sorter, the desired cell can be separated from the population of undesired cells. In some instances, the Sca-1+, CD45− cell can be isolated using antibodies and magnetic bead technology commercially available from, e.g., Miltenyi Biotec and Invitrogen. The Sca-1+, CD45− cell can be isolated by any method that allows the cell to be cultured and expanded.

The inventors have determined that Sca-1+, CD45− cells can express CD44, CD105, and/or CD80. In some instances, 38% of Sca-1+, CD45− cells express CD44; 86% of Sca-1+, CD45− cells express CD105; and/or 44% of Sca-1+, CD45− cells express CD80.

The Sca-1+, CD45− cell can be cultured and expanded in cardiosphere growth medium including buffered media containing 35% IMDM, 65% DMEM-F12, 3.5% FBS, 0.1 mM β-mercaptoethanol, 2% B27, 10 ng/ml EGF, 20 ng/ml bFGF, 40 nmol/L thrombin and 4 nmol/L cardiotrophin. Any component of the growth medium originating from an animal can be substituted for a non-animal derived equivalent.

In some embodiments, the Sca-1+, CD45− cell is cultured for about 7-30 days, e.g., at least 7, 8, 9, 10, 11, 12, 13, 14, 15, 20, 22, 24, 26, 28, or more days (i.e., the course or duration of cardiac progenitor cell growth and/or differentiation). The Sca-1+, CD45− cell can be passaged about 2-20 times, e.g., at least 2, 4, 6, 8, 10, 12, 14, 16, 18, 19 or more times. As is understood by one of skill in the art, the cells can be passaged and the cell media changed periodically during the course of culturing.

The Sca-1+, CD45− cell is clonally expanded in vitro, such that the single cell gives rise to a population of CPCs, e.g., as described above. CPCs, obtained by the method of isolating a Sca-1+, CD45− cell from a cardiosphere derived from heart tissue, and culturing the Sca-1+, CD45− cell comprise at least 3%, 5%, 7%, 10%, 12%, or 15%, e.g., 3-50%, 3-20%, 3-10%, 5-30%, 5-10%, etc., Isl1 expressing cells. CPCs of the method described herein can comprise about 10%, 15%, 20%, 30%, 40%, or 50%, e.g., 10-50%, 10-40%, 10-30%, 15-40%, etc., GATA4 expressing cells. Further, CPCs can comprise about 5%, 8%, 10%, 13%, or 15%, e.g., 8-15%, 5-15%, 5-13%, etc., NKX2.5 expressing cells.

The clonal population of cardiac progenitor cells can express cell surface markers such as, c-kit, CD44, CD80, CD90, CD105, CD133, CD34, Sca-1 and CD45, and cardiac markers such as Isl1, Nkx2.5, and GATA4, and endothelial markers such as Flk1.

The expression of specific genes or markers (e.g., Isl1, GATA4, NKX2.5) can be determined by detecting or measuring the presence of RNA or protein encoded by the specific genes. The expression of cell surface markers can be determined by detecting or measuring the protein (e.g., marker or antigen) on the surface of the cell. Useful methods for detecting RNA include qPCR, RT-PCR, microarray, and capillary electrophoresis, and are described in, e.g., Sambrook et al., MOLECULAR CLONING, A LABORATORY MANUAL, 4$^{rd}$ ed., Cold Springs Harbor Laboratory Press (Cold Spring Harbor, N.Y. 2012). Useful methods for detecting protein include flow cytometry, Western blot, immunoassay, ELISA, immunocytochemistry, and are described in, e.g., Sambrook et al., MOLECULAR CLONING, A LABORATORY MANUAL, 4$^{rd}$ ed., Cold Springs Harbor Laboratory Press (Cold Spring Harbor, N.Y. 2012).

Additional information regarding cell culture techniques can be found, e.g., in Picot (2005) HUMAN CELL CULTURE PROTOCOLS; Piper (1990) CELL CULTURE TECHNIQUES IN HEART AND VESSEL RESEARCH; and Mather (2008) STEM CELL CULTURE, vol. 86, *Meth. Cell Biol*. Freshney R. I., CULTURE OF ANIMAL CELLS: A MANUAL OF BASIC TECHNIQUE AND SPECIALIZED APPLICATIONS, 6$^{th}$ ed., J. Wiley & Sons (Hoboken, N.J. 2010). Suitable culture conditions for growing and expanding cells are described herein including Example 1, and can include standard tissue culture conditions. Reagents and protocols for cell culture can also be found commercially, e.g., from Invitrogen, Gen-Probe, Lonza, and Clonagen, to name a few.

In some embodiments, the injured or damaged heart is from a subject having acute myocardial infarction. In some embodiments, the injured or damaged heart is from a subject having ischemic cardiomyopathy. In other embodiments, the injured or damaged heart is from a subject with cardiovascular disease.

In some embodiments, CPCs are administered back to the individual from which the cells were derived. CPCs can be used for autologous transplantation to treat an individual with cardiovascular disease and related disorders. Non-limiting examples of cardiovascular disease include acute myocardial infarction, myocardial ischemia, chronic heart failure, peripheral artery disease, critical limb ischemia, stroke (e.g., ischemic and hemorrhagic).

In some embodiments, CPCs are administered to a different individual from which the cells were derived. CPCs can be used for allogeneic transplantation to treat an individual with cardiovascular disease and related disorders. Non-limiting examples of cardiovascular disease include acute myocardial infarction, myocardial ischemia, chronic heart failure, peripheral artery disease, critical limb ischemia, stroke (e.g., ischemic and hemorrhagic).

V. Methods of Treatment

Provided herein are methods of treating a human subject with an injured heart by administering CPCs, as described herein. In some embodiments, CPCs are administered to patient with acute myocardial infarction or having myocardial ischemia. Further provided are methods of treating a patient in need of angiogenesis (e.g., growth of blood vessels) by administering CPCs, as described herein. CPCs can be used to ameliorate the effects of any type of injury to the heart.

In some embodiments, CPCs are generated by isolating a Sca-1+, CD45− cell from a cardiosphere derived from the injured heart of the subject, and culturing the Sca-1+, CD45− cell, as detailed above to generate CPCs. The method of treatment can include obtaining CPCs from the subject prior to treatment. In some aspects, CPCs are isolated, frozen down (e.g., preserved and stored), thawed, and cultured prior to use for treatment. In some embodiments, the CPCs can be preserved at −20° C., −70° C., or in liquid nitrogen freezer in a standard preservation solution comprising, e.g., DMSO. In some aspects, CPCs are stored frozen, thawed and cultured when needed for treatment.

CPCs can be administered back to the individual from which the cells were derived or to a different individual. Thus, CPCs can be used for autologous or allogeneic transplantation to treat an individual with an injured heart or an individual who can benefit from angiogenesis. CPCs, as described herein, are non-transgenic. Therefore, they are more suitable for transplantation into a patient compared to genetically modified cells or cells transduced with viruses and the like.

In some embodiments, provided herein are methods comprising administering CPCs to an individual who has damaged blood vessels. In some instances, the damaged blood vessels are due to disease or conditions such as peripheral arterial disease, critical limb ischemia, or chronic wounds (e.g., diabetic lower extremity ulcers, venous leg ulcers, pressure ulcers, arterial ulcers), to name a few. For example, CPCs can be administered to an individual suffering from a stroke (e.g., acute or chronic) or a condition causing blood vessel injury in the brain in order to repair the brain.

To repair and/or regenerate blood vessels, CPCs can be administered alone or in combination with angiogenesis promoting factors including IL-15, FGF, VEGF, angiopoietin (e.g., Ang1, Ang2), PDGF, TGF-β, and MCPJ.

Methods of administration include injection, transplantation, or other clinical methods of getting cells to a site of injury in the body. Non-limiting examples of injection methods that can be used to administer CPCs include intravenous injection, intracoronary injection, transmyocardial injection, epicardial injection, direct endocardial injection, catheter-based transendocardial injection, transvenous injection into coronary veins, intrapericardial delivery, or combinations thereof.

The injection of CPCs can be either in a bolus or in an infusion. The CPC composition can comprise a pharmaceutical carrier. Pharmaceutically acceptable carriers are determined in part by the particular method used to administer the cell composition, but are typically isotonic, buffered saline solutions. Accordingly, there are a wide variety of suitable formulations of pharmaceutical compositions for the presently described compositions (see, e.g., Remington's Pharmaceutical Sciences, 17th ed., 1989). The CPC compositions described herein can be administered in a single dose, a plurality of doses, or on a regular basis (e.g., daily) for a period of time (e.g., 2, 3, 4, 5, 6, 7, days, weeks, months, or as long as the condition persists).

The dose (e.g., amount of cells) administered to the subject, in the context of the present disclosure should be sufficient to effect a beneficial response in the subject over time, e.g., repair or regeneration of heart tissue, repair of regeneration of blood vessels, or a combination thereof. The optimal dose level for any patient will depend on a variety of factors including the efficacy of the specific modulator employed, the age, body weight, physical activity, and diet of the patient, on a possible combination with other drugs, and on the severity of the cardiac or angiogenic injury. The size of the dose also will be determined by the presence, existence, nature, and extent of any adverse side-effects that accompany the administration of the CPCs in a particular subject.

CPCs can be transplanted into the individual at a single or multiple sites. CPCs can be administered alone or in combination with biomaterials (e.g., hydrogel or 3-dimensional scaffolds) prior to transplantation in order to promote engraftment and stimulate tissue repair. CPCs can be embedded in a biodegradable or biocompatible material that is applied to the site in need of cell-based therapy. Scaffolds can increase the retention of the CPCs and the viability of the cells upon delivery to the site of injury.

EXAMPLES

Example 1

Sca-1+ Cardiosphere-Derived Cells are Enriched for Isl1 Expressing Cardiac Precursors and Improve Cardiac Function after Myocardial Injury Introduction Growing evidence demonstrates the existence of endogenous cardiac progenitor cells in the adult mammalian heart, which can divide and differentiate into cardiomyocytes, endothelial cells and smooth muscle cells, and potentially play an important role in maintaining normal cardiac homeostasis, as well as myocardial response to injury. Various methods have been used to isolate cardiac progenitor cells, including immune selection of cells using various cell surface markers or in vitro culture of cardiospheres (CSs). See, e.g., Messina E et al., *Circ Res.*, 2004; 95:911-921; Smith R R et al., *Circulation.* 2007; 115:896-908; Tang Y L et al., *Biochem Biophys Res Commun.*, 2007; 359:877-883. Endogenous cardiac progenitor cells can be collected from the hearts of patients by myocardial biopsy, expanded in vitro, and then potentially be transplanted back to the same patient to repair damaged myocardium. This approach would avoid immune rejection and may therefore represent an ideal model for cell therapy to achieve long term reconstitution of lost myocardium and preservation of cardiac function. However, the myocardiogenic potential of cardiospheres and adult cardiac progenitor cells has recently been questioned.

During fetal development, the LIM homeodomain transcription factor Islet-1 (Isl1) is expressed in a cell population that gives rise to second heart field structures and the myocardial vasculature, and is accepted as a marker of endogenous cardiac progenitors. Since Isl1 is expressed in the nucleus, it has been difficult to isolate and purify genetically unmodified endogenous Isl1+ cells for therapeutic evaluation. Cells bearing the surface markers c-kit and Sca-1 have been isolated from the adult heart and recognized as adult resident cardiac progenitor cells.

Questions remain regarding the behavior and cellular composition of cardiospheres and their response to signals from the myocardial tissue environment, including: (1) whether acute myocardial infarction (MI) effects the generation of cardiospheres; (2) whether cardiospheres derived from injured myocardium have therapeutic potential to repair ischemically damaged hearts in vivo; and (3) whether specific subpopulations of cardiosphere cells bear the therapeutic potential of cardiosphere in vivo. In this study we demonstrate that the Sca-1+CD45− cardiosphere subpopulation from post-MI "middle-aged" hearts are enriched in Isl1+ cells, have the potential to differentiate into both cardiomyocytes and vascular cells, indicating that the Sca-1+CD45− population are cardiac progenitor cells. Furthermore, we show that these cardiac progenitor cells can be transplanted and used to improve cardiac function in the injured heart.

Endogenous cardiac progenitor cells are a promising option for cell-therapy for myocardial infarction (MI). However, obtaining adequate numbers of cardiac progenitors after MI remains a challenge. Cardiospheres (CSs) have cardiac regenerative properties.

Methodology/Principal Finding

Using "middle aged" mice as CSs donors, we found that acute MI induced a dramatic increase in the number of CSs in a mouse model of MI, and this increase was attenuated back to baseline over time. We also observed that CSs from post-MI hearts engrafted in ischemic myocardium induced angiogenesis and restored cardiac function. To determine the role of Sca-1+CD45− cells within CSs, we cloned these from single cell isolates. Expression of Islet-1 (Isl1) in Sca-1$^+$CD45− cells from CSs was 3-fold higher than in whole CSs. Cloned Sca-1$^+$CD45− cells had the ability to differentiate into cardiomyocytes, endothelial cells and smooth muscle cells in vitro. We also observed that cloned cells engrafted in ischemic myocardium induced angiogenesis, differentiated into endothelial and smooth muscle cells and improved cardiac function in post-MI hearts.

Results

CSs Enrichment with Injury

Figure 11:
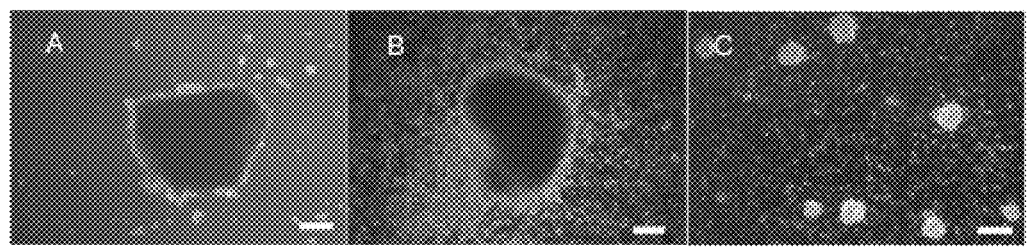
FIG. 11: CS culture. (A) Typical explants of cardiac tissue, one day after placing into culture. (B) CS-forming cells are seen as small, round, phase-bright cells arising from the fibroblast-like monolayer around the attached explant after 14 days. (C) CSs appear 3 days after the CS-forming cells are re-plated in separate wells. Typical results are shown (N=12). Scale bar=200 μm.
Figure 12:
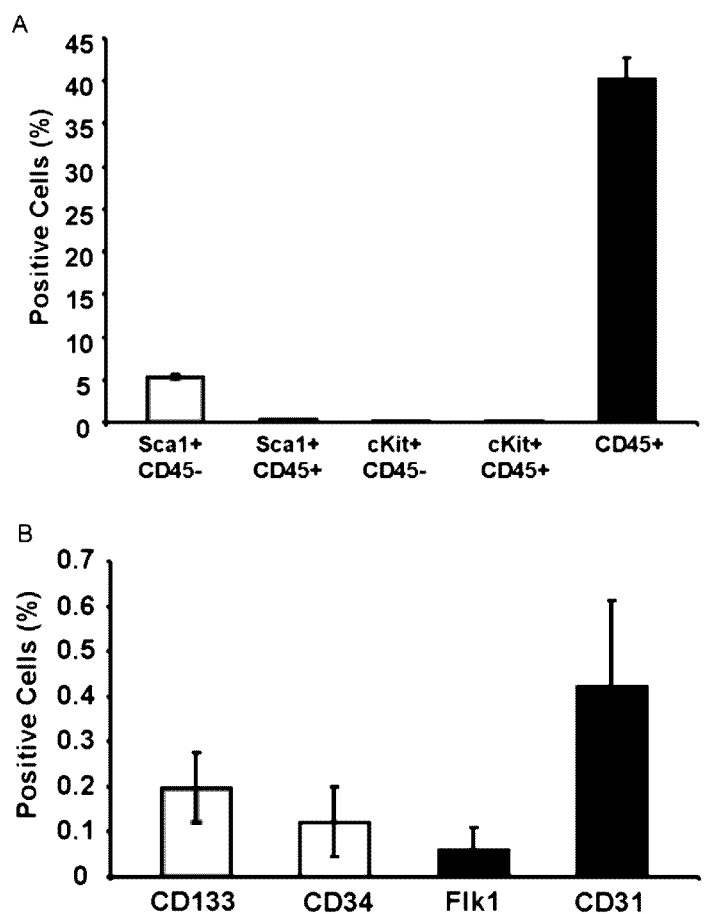
FIG. 12: Cellular composition of CS-forming cells from mouse hearts. (A) Flow cytometric analysis of Sca-1, CD45 and c-kit expression in disaggregated CS cells (N=5). (B) Bar graph showing the profile of progenitor cell markers in CSs by FACS(N=5). Data are shown as mean±SEM.

To determine whether myocardial injury influences the generation of CS-forming cells, whole hearts including the infarct area were removed from mice following experimental MI, as well as from sham-operated and non-operated mice, and were cut to small pieces as "explants". A monolayer of fibroblast-like cells migrated out from the cardiac explants over several weeks in culture. From this monolayer, small, round, phase-bright cells (CS-forming cells) were seen to emerge (FIG. 11A, B). CS-forming cells from non-operated hearts contained several populations of cells, based on their expression of Sca-1, c-kit, CD45, CD133, CD34, Flk1 and CD31 (FIG. 12A, B). We observed that explants took less time to form confluent monolayer in culture when isolated from injured hearts (14±1, 13±1 and 18±2 days from 1-, 2- and 4-weeks post-MI hearts, respectively), compared to explants derived from sham-operated and non-operated hearts (21±1 and 32±2 days, respectively). Thus, cells derived from 1- and 2-week post-MI cardiac explants expanded more rapidly than both control groups (P<0.004), however, the growth rate of these cells was attenuated by 4-weeks post-MI and was not significantly different from the sham-operated hearts (P>0.05).

In addition to faster growth rates, the number of putative CS-forming cells harvested from hearts at 1-week ($5.12 \times 10^5 \pm 0.45 \times 10^5$/heart) and 2-weeks ($3.75 \times 10^5 \pm 0.52 \times 10^5$/heart) post-MI was significantly higher than those from sham-operated ($2.20 \times 10^5 \pm 0.70 \times 10^5$/heart) and non-operated hearts ($1.67 \times 10^5 \pm 0.26 \times 10^5$ cells/heart) ($P < 0.045$) (FIG. 1A). MI therefore produced more than twice as many CS-forming cells in approximately half the culture time, equivalent to an approximate four-fold increase in proliferative rate. However, the number of putative CS-forming cells harvested 4-weeks post-MI ($2.88 \times 10^5 \pm 0.46 \times 10^5$ cells/heart) hearts was not significantly different from sham-operated and non-operated hearts ($P > 0.05$), suggesting that the increase in the number of CS-forming cells was also attenuated by 4-weeks post-MI (FIG. 1A).

Consistent with our observation of an increase in CS-forming cell number with injury, we observed that the number of CSs derived from hearts harvested 1-week ($354 \pm 50$/heart) and 2-weeks ($213 \pm 38$/heart) post-MI were significantly higher than from sham-operated hearts ($80 \pm 33$/heart) ($p < 0.001$) and non-operated hearts ($18 \pm 14$/heart) ($P < 0.01$) (FIG. 1B). Our results also showed that the number of CSs from hearts 4-weeks post-MI ($141 \pm 42$/heart) was not significantly different compared to sham operated hearts ($P > 0.05$), but still higher than from non-operated hearts ($P = 0.02$) (FIG. 1B). Thus, the effect of injury on CS formation was attenuated by 4-weeks post-MI.

We have demonstrated that at each of the three stages of CS formation (explant outgrowth, CS-forming cell generation and number of CSs), the proliferative was greater at 1-2 weeks post-MI, and this then returned toward baseline by 4 weeks post-MI.

No Regional Differences in CS-Yield from Infarcted Hearts

Figure 13:
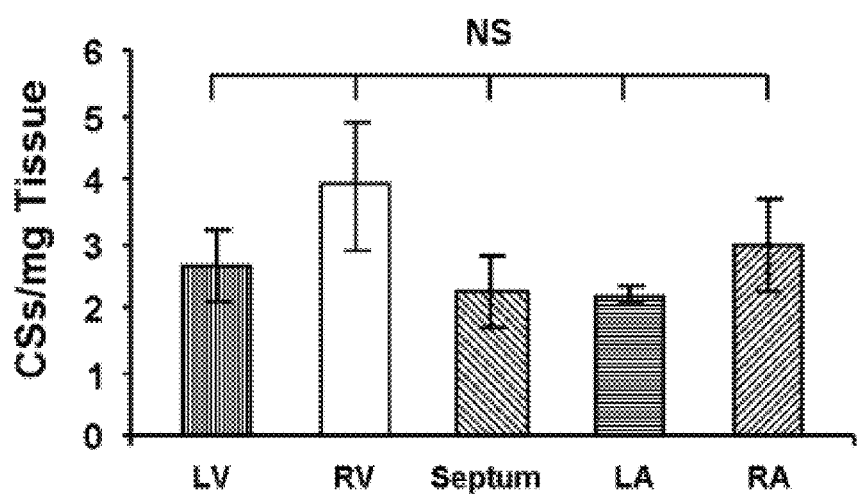
FIG. 13: CSs generated from different cardiac regions. Different cardiac regions generated similar number of CSs per milligram of tissue at 1 week post-MI. LV, left ventricle excluding scar; RV, right ventricle; LA, left atrium and RA, right atrium. Data are shown as mean±SEM (N=4).

To determine the CS generating potential of different regions of the heart, we separated the hearts 1-week post-MI into five regions: left ventricle (LV) excluding scar, right ventricle (RV), septum, left atrium (LA) and right atrium (RA), and cultured them separately. The number of CSs from each region of the heart was counted and adjusted for tissue weight. We observed no statistically significant regional differences in CS production (LV: $2.6 \pm 0.6$ CSs/mg; RV: $3.8 \pm 1.0$; septum: $2.3 \pm 0.5$; LA: $2.2 \pm 0.2$; RA: $2.9 \pm 0.7$; $P > 0.05$) (FIG. 13).

CSs Contain Isl1+ Cells

Figure 2:
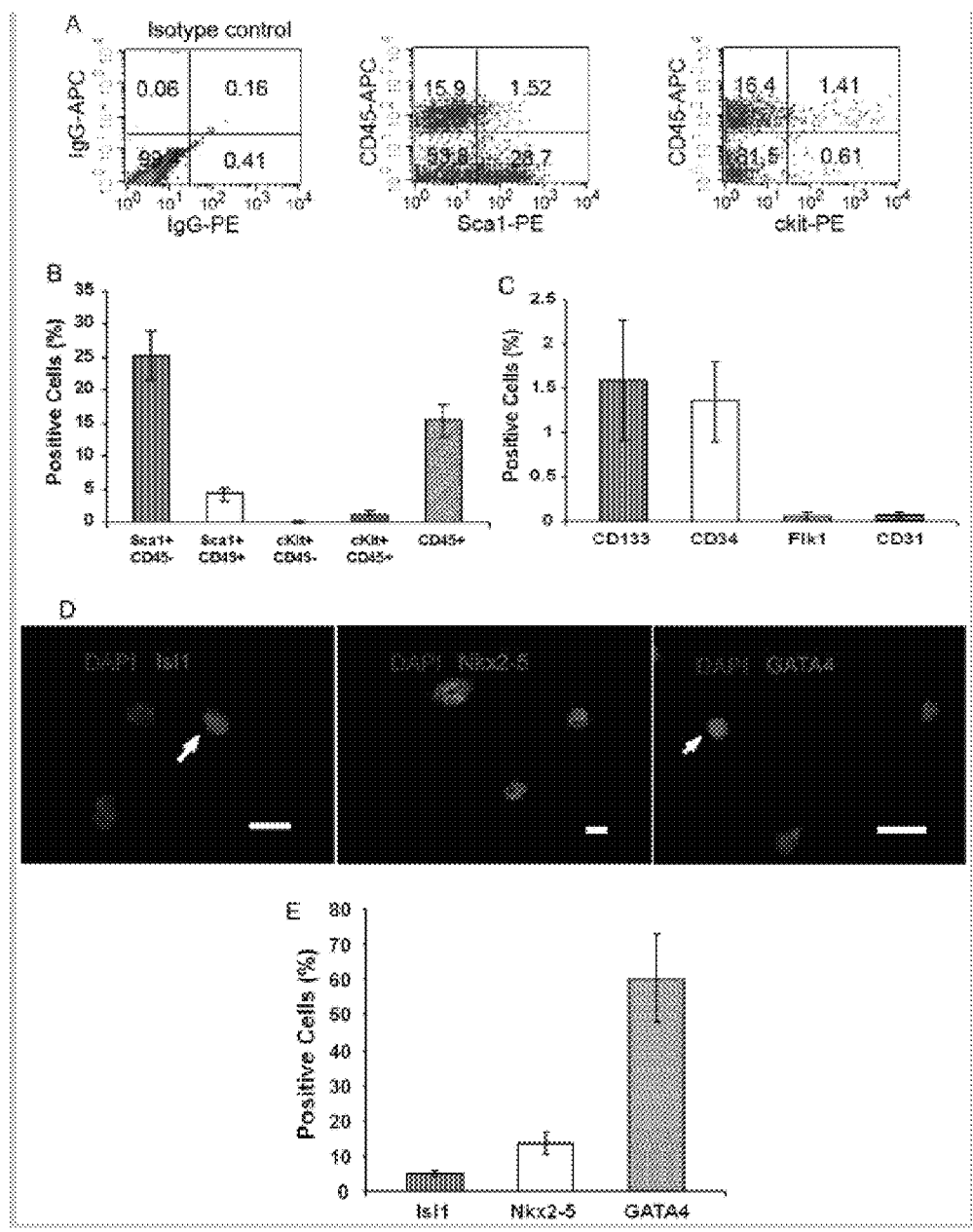
FIG. 2: Cellular composition of CSs from mouse hearts.

We used fluorescence-activated cell sorting (FACS) to determine the cellular composition of CSs derived from control and infarcted hearts after 14 days in culture. CSs from non-operated hearts contained several populations of cells, based on their expression of Sca-1, c-kit, CD45, CD133, CD34, Flk1 and CD31 (FIGS. 2A, B and C). Immunocytochemical staining showed that the cardiac transcription factors, Isl1, Nkx2-5 and GATA4, were expressed in $5.0 \pm 1.0\%$, $13.6 \pm 1.4\%$, and $60.1 \pm 5.6\%$ of CS cells, respectively (FIGS. 2D and E). These were confirmed by real-time RT-PCR (FIG. 3A) and semi-quantitative RT-PCR (FIG. 4C). To determine whether Isl1 expression occurred only with culture ex vivo, we checked Isl1 expression in adult whole heart by real-time RT-PCR, and found that Isl1 was indeed expressed in whole heart. This finding is consistent with a recent report that showed cells expressing Isl1 protein in adult non-operated murine hearts by immunohistochemical staining Notably however, the expression level of Isl1 mRNA in CSs was 17-fold higher than in the adult heart (FIG. 3A).

Figure 3:
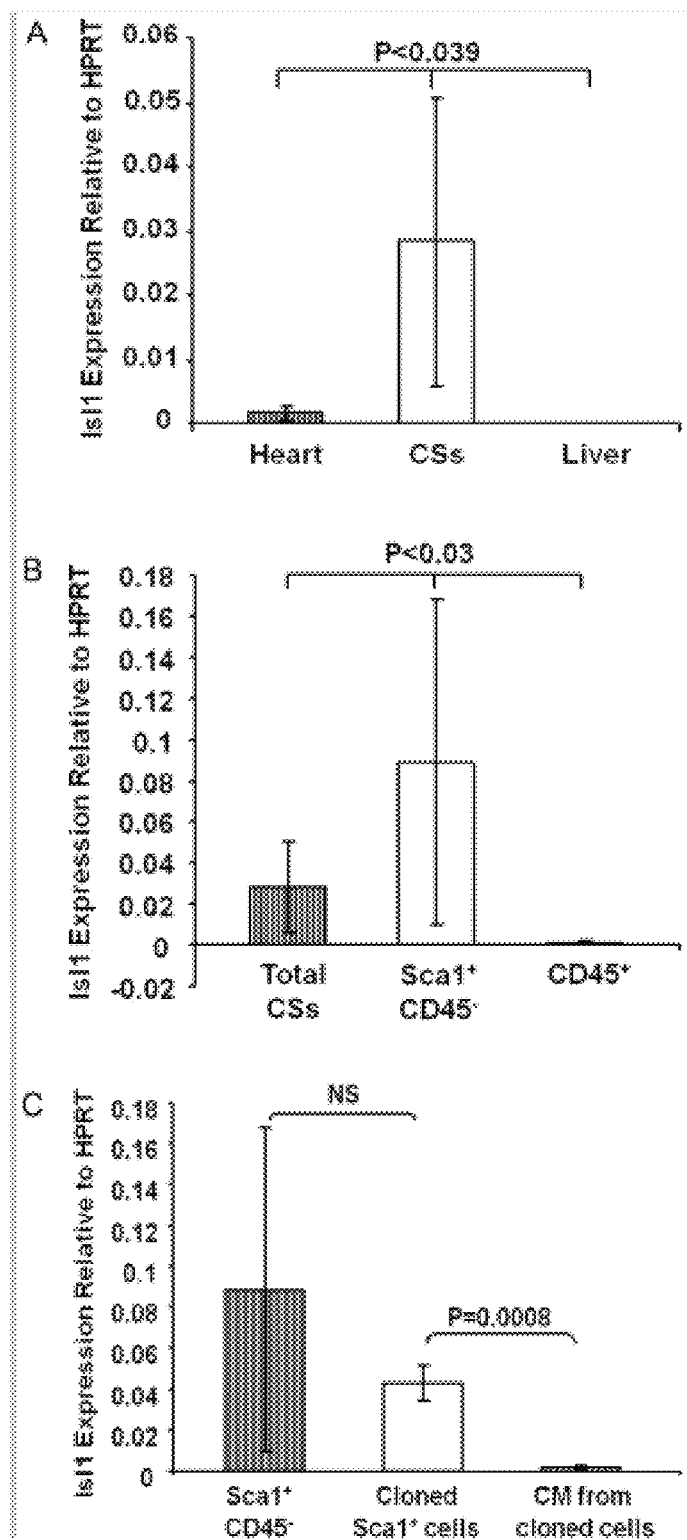
FIG. 3: Isl1+ cells are present in adult heart and CSs.
Figure 4:
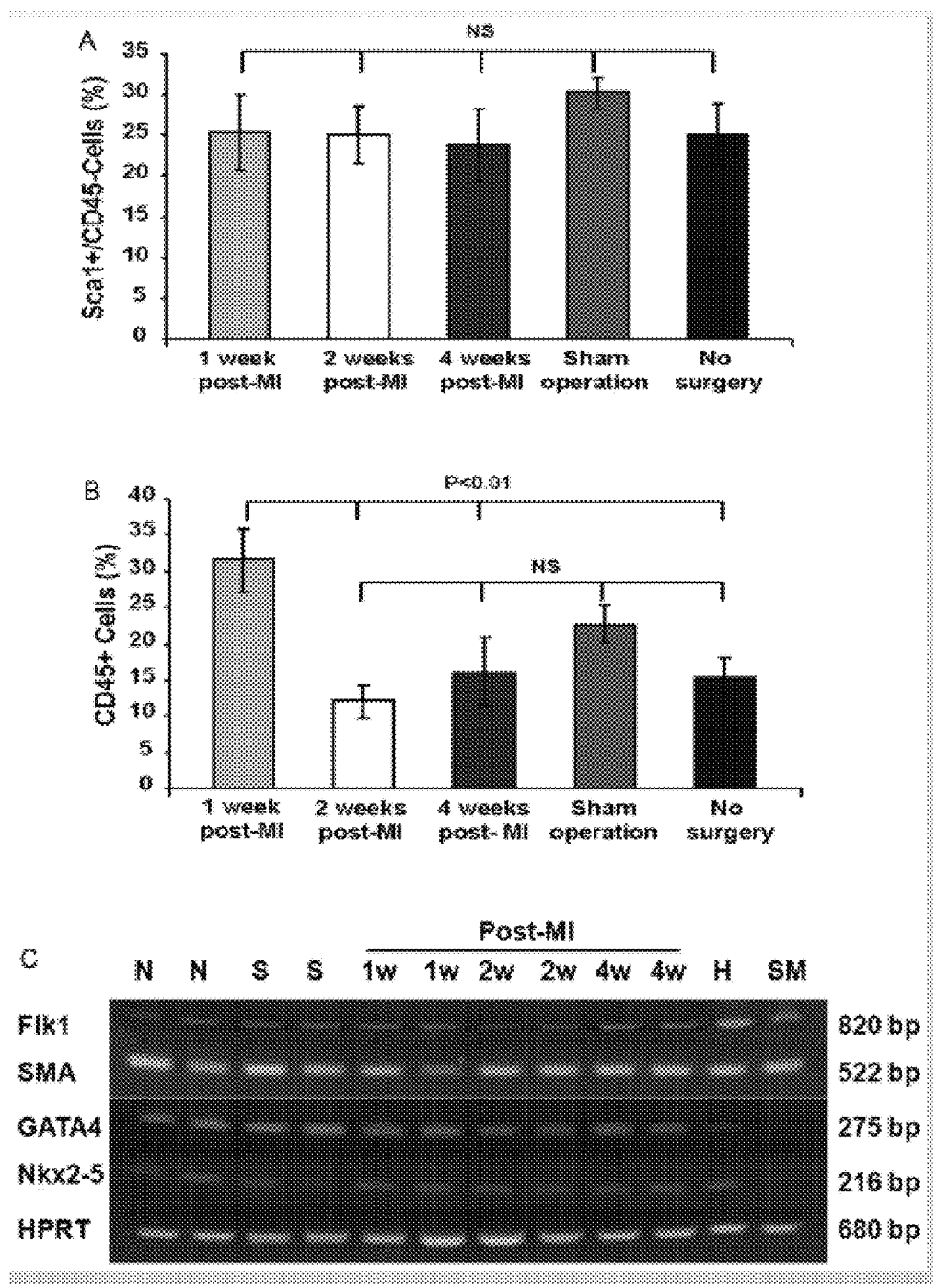
FIG. 4: Cellular composition of CSs from injured hearts.

To determine the source of Isl1 enrichment in CSs, we analyzed RNA from Sca-1+CD45− and CD45+ cells sorted from CSs, and found that Isl1 expression in Sca-1$^+$CD45− cells was 3-fold higher than in whole CS cells, and that the CD45+ fraction did not express Isl1 (FIG. 3B). These results suggested that Sca-1$^+$CD45− cells derived from CSs are enriched for Isl1+ cells, and, as expected, no Isl1+ cells were detected among hematopoietic cells of bone marrow origin. In addition, with the exception of CD45+ cells, which likely represent inflammatory cells that migrate into the heart post-MI, the proportions of other cell populations in CSs from infarcted heart were not altered compared to non-operated hearts (FIG. 4A, B, C).

Figure 14:
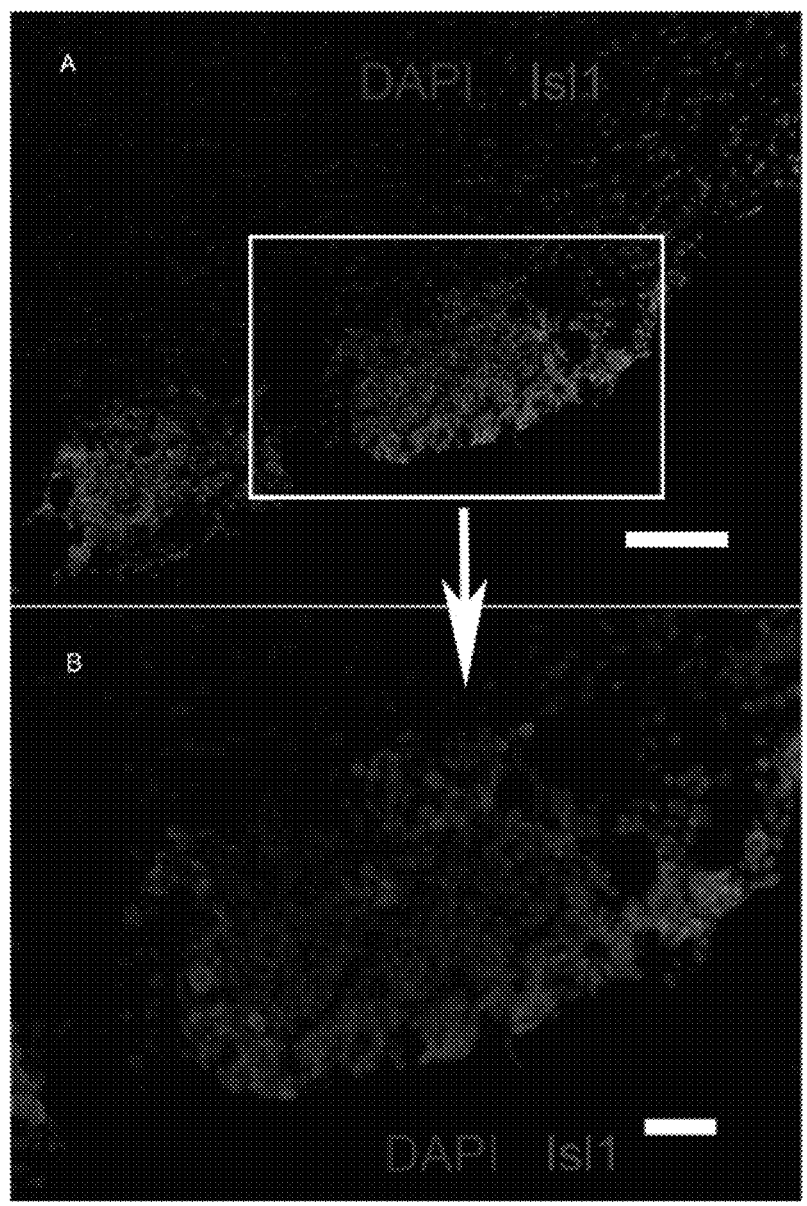
FIG. 14: Isl1+ cells in post-MI heart. After 7 days post-MI, Isl1+ cells were detected in epicardium at the border of infarct region by immunohistochemical staining in 9 month old mice at lower power (scale bar=35 μm) (A) and higher power (scale bar=100 μm) (B) (N=3).

We investigated whether Isl1 protein expression was detected in the post-MI hearts of "middle aged" mice using immunohistochemical staining and found Isl1+ cells in the epicardium at the border of the infarct region at 1 week post-MI (FIG. 14). A significant number of Isl1+ cells in the epicardium and subepicardial regions are found at the border of the infarct scar at 7 days post-MI by genetic tracing and immunohistochemical staining Together, these indicate that Isl1-expressing cells are present in the post-MI heart of middle aged mice.

Figure 5:
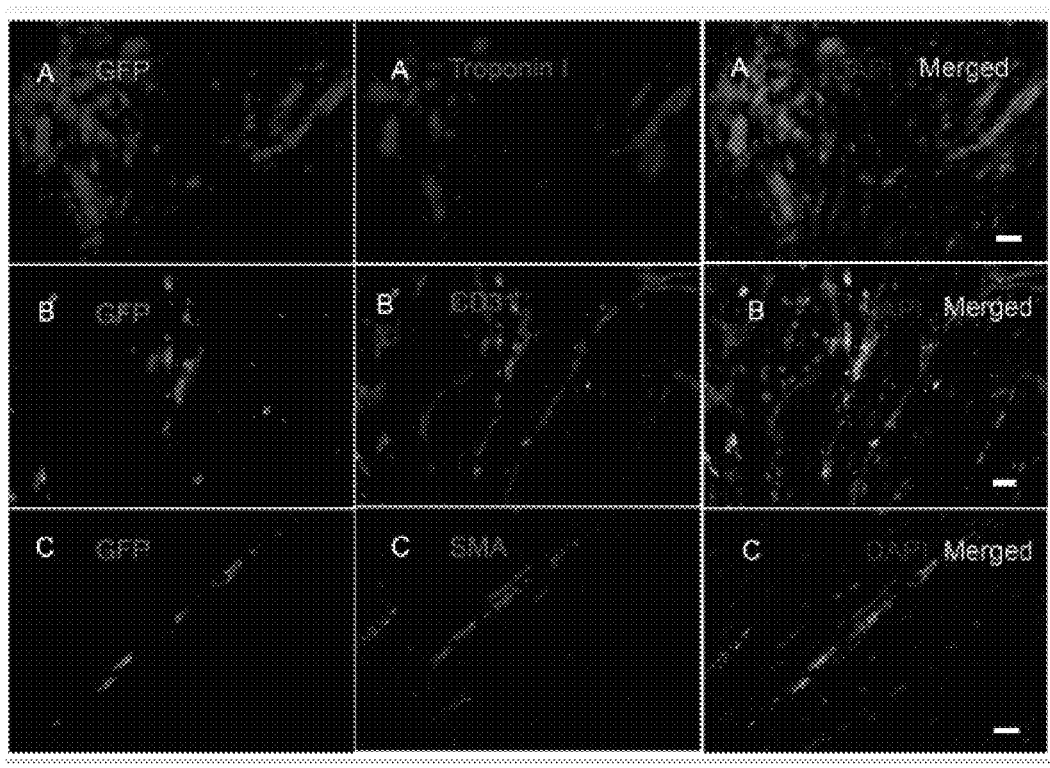
FIG. 5: CS cells engraft in ischemic myocardium.

CS Cells Derived from Infarcted Myocardium Engraft in Ischemic Myocardium In Vivo To determine whether CSs from infarcted myocardium differentiate into cardiac cells in vivo, we harvested CSs derived from 1-week post-MI hearts of GFP transgenic mice, injected $10^5$ GFP+ cells into the peri-infarct zone (PZ) of syngeneic wild type mice at 3 days post-MI, and analyzed hearts by immunohistochemistry at 25 days post-injection. Numerous GFP+ cells were found in infarct and peri-infarct zones (FIGS. 5A, B and C). Approximately 10% of engrafted GFP+ cells expressed cardiac Troponin I, and ~10% of engrafted GFP+ cells expressed either the endothelial cell marker, CD31, or the smooth muscle cell marker, a smooth muscle actin ($\alpha$-SMA) (FIGS. 5A, B and C). However, Troponin I+GFP+ cells lacked the sarcomeric structure seen in typical mature cardiomyocytes, and CD31+ or SMA+ cells were not incorporated into vascular structures. Nevertheless, our findings demonstrated that the injected CSs cells derived from infarcted heart survived in the ischemic, inflammatory microenvironment for at least 25 days in vivo, and expressed markers of nascent cardiac muscle, endothelium, and vascular smooth muscle.

CSs from Infarcted Myocardium Promote Angiogenesis In Vivo

Figure 6:
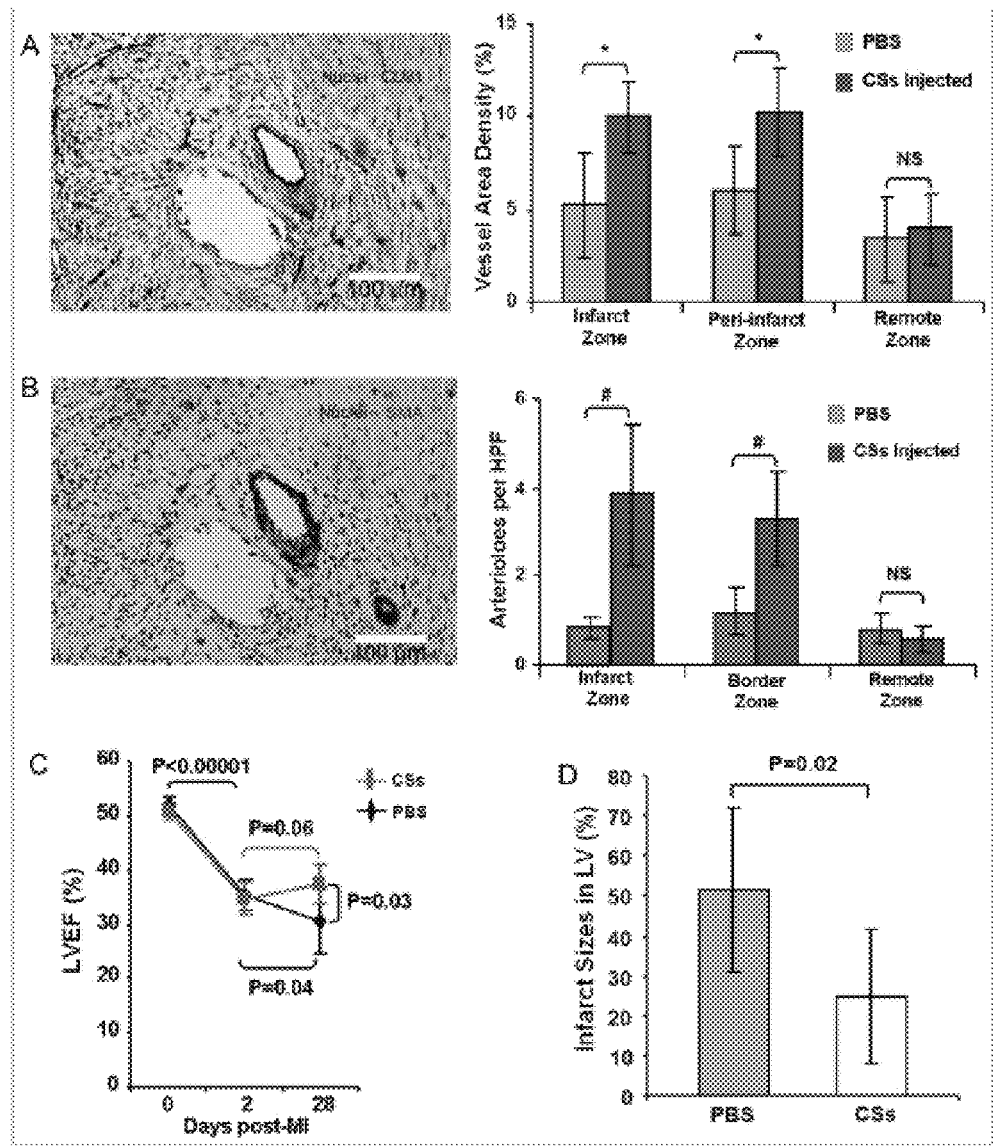
FIG. 6: Injected CS cells promote angiogenesis, limited infarct size and improve cardiac function.

To determine whether transplantation of CSs promoted angiogenesis in ischemic myocardium, we quantified the capillary and arteriole density in hearts at day 25 post-injection The results showed a greater density of CD31+ vessels in the infarct zone (IZ) ($10.0 \pm 1.9\%$ vs. $5.3 \pm 2.8\%$, $P = 0.002$) and PZ ($10.3 \pm 2.4\%$ vs. $6.0 \pm 2.4\%$, $P = 0.0004$) in CS-injected versus control hearts (FIG. 6A). Moreover, the CS-injected group had a significantly higher number of arterioles (SMA+) in the IZ and PZ vs. control ($3.8 \pm 1.6$ and $3.2 \pm 1.1$/high power field (HPF) vs. $0.8 \pm 0.2$ and $1.2 \pm 0.5$/HPF, $P < 0.0005$) respectively (FIG. 6B). Vessel counts did not differ between the CS-injected and control groups in the remote zone (RZ) (CD31+ vessels: $4.0 \pm 1.9\%$ vs. $3.4 \pm 2.3\%$, $P > 0.05$; SMA+ arterioles $0.6 \pm 0.3$ vs. $0.8 \pm 0.3$/HPF, $P > 0.05$) (FIG. 6A, B). Because engrafted CD31+ and SMA+ cells did not contribute to vessel-like structures at this time point, these results suggest that injection of CSs promoted endogenous angiogenesis.

Injected CSs from Infarcted Myocardium Reduced Infarct Size and Improved Cardiac Function To determine whether injection of CSs from infarcted myocardium improved cardiac function in a MI mouse model, we evaluated left ventricular ejection fraction (LVEF) by echocardiography and measured infarct size by histochemical staining at 25 days post-injection. LVEF was significantly reduced from an average of 51.2±1.7% before MI to 35.1±2.9% at 2 days post-MI in both groups, with no significant difference between two groups (P>0.05). At 28 days post-MI (25 days post-injection), LVEF was significantly higher in the CS-injected group (37.5±3.5%) compared to control (30.9±6.6%, P=0.03) (FIG. 6C). Furthermore, we found that the CS-injected group had significantly smaller relative infarct size compared to control (24.8±16.5% vs. 48.4±19.8%, P=0.02) (FIG. 6D). These findings suggest that CSs from injured myocardium have a beneficial effect in the MI mouse model.

Sca-1+CD45− Cells in CSs have the Characteristics of Cardiac Progenitor Cells In Vitro In our studies, the Sca-1$^+$CD45− subpopulation comprised the largest fraction of CS cells, and contained more Isl1+ cells.

Figure 15:
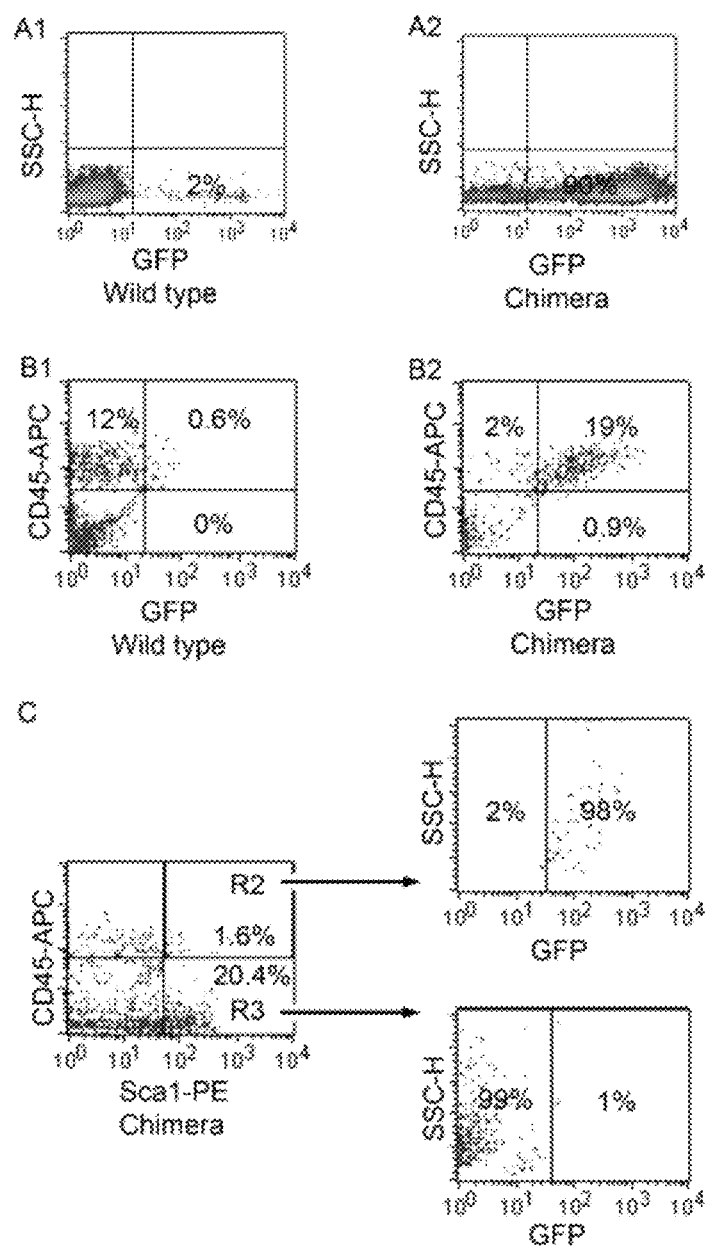
FIG. 15: Sca-1+CD45− cells in CSs from chimeric mouse are GFP negative. Flow cytometric analysis GFP+ cells in peripheral blood mononuclear cells in wild type mouse (A1) and in chimeric mouse 5 months post-transplantation (A2). FACS showed CD45+ cells in CSs from wild type mouse (B1) and CD45+GFP+ cells in CSs from chimeric mouse (B2). FACS showed Sca-1+CD45− cells in CSs from chimeric mouse were GFP negative, whereas Sca-1+CD45+ cells were GFP positive (C). Typical results are shown (N=4).
Figure 16:
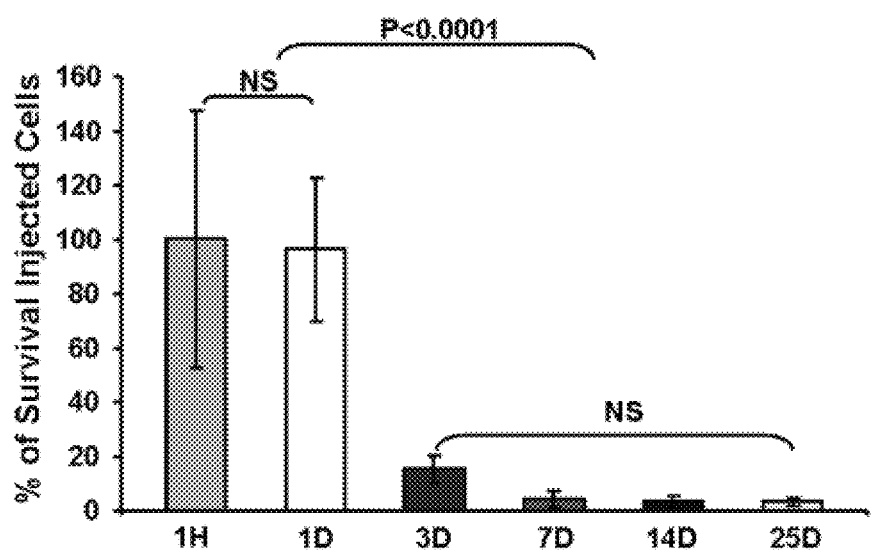
FIG. 16: The level of engraftment and persistence of injected cells in infarcted hearts. Real-time RT-PCR (Taqman) was used to compare GFP expression in hearts injected with cloned Sca-1+CD45−GFP+ cells. The injected hearts were harvested at 1 hour and 1, 3, 7, 14 and 25 days post-injection. Results show as GFP mRNA expression relative to histone 3.3A. The expression level of GFP in the heart collected 1 hour post-injection was used to represent 100% of injected cells. H: hour; D: day. Typical results are shown (N=3).

To further investigate the origin of Sca-1$^+$CD45− in CSs, chimeric mice were generated by transplantation of bone marrow cells isolated from GFP transgenic mice to lethally irradiated C57BL/6 mice. Flow cytometric analysis demonstrated that 88±0.5% of peripheral blood mononuclear cells were GFP+ in the chimeric mice 5 months post-transplantation (FIG. 15A), indicating stable bone marrow engraftment. About 18.4±4.5% of cells in CSs derived from the no-surgery or 2-week post-MI hearts of chimeric mice co-expressed GFP and CD45 (FIG. 15B), indicating they originated from bone marrow. All of the Sca-1$^+$CD45− cells were GFP negative (FIG. 15C), suggesting that they did not originate from the bone marrow.

Figure 7:
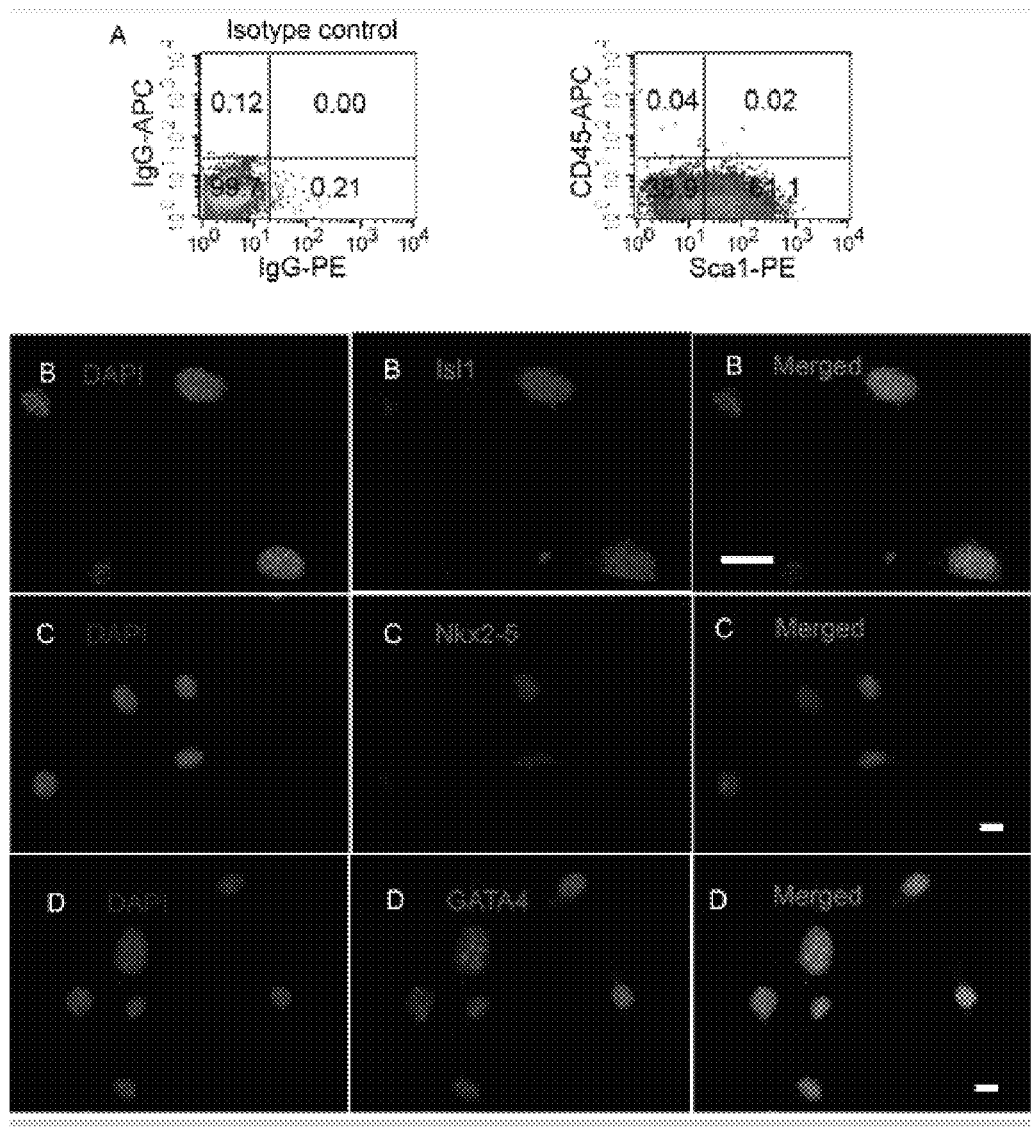
FIG. 7: Analysis of cloned Sca-1+CD45− cells.

To further investigate whether these cells play a key role in restoring cardiac function and reducing infarct size, we sorted Sca-1$^+$CD45− cells from CSs from 1-week post-MI hearts of adult GFP transgenic mice, and clonally expanded these in culture from single cells. After culturing for 14 days, 5.6% ($^{16}/_{288}$) of the single cells grew to colonies. About 30% ($^{3}/_{10}$) of clones grew to >106 cells after 30 days in culture. To determine the cellular composition of cloned cells derived from a single Sca-1$^+$CD45− cell, we analyzed the cell-types of cloned cells by FACS after 30 days at passage 4, 15 and 22. FACS analysis showed that 61.8±12.4% of the clonally derived cells was still Sca-1$^+$CD$_{45}$− (FIG. 7A), 0.164±0.007% c-kit+, 1.7±0.1% CD90+, 0.03±0.02% CD133+, 1.1±0.6% CD$_{34}$+, 0.6±0.3% CD31+ and 0.3±0.2% Flk1+. In addition, GATA4, Nkxx2-5, and Isl1 were expressed in 60%, 20% and 10% of cloned cells, respectively (FIGS. 7B, C and D).

Figure 8:
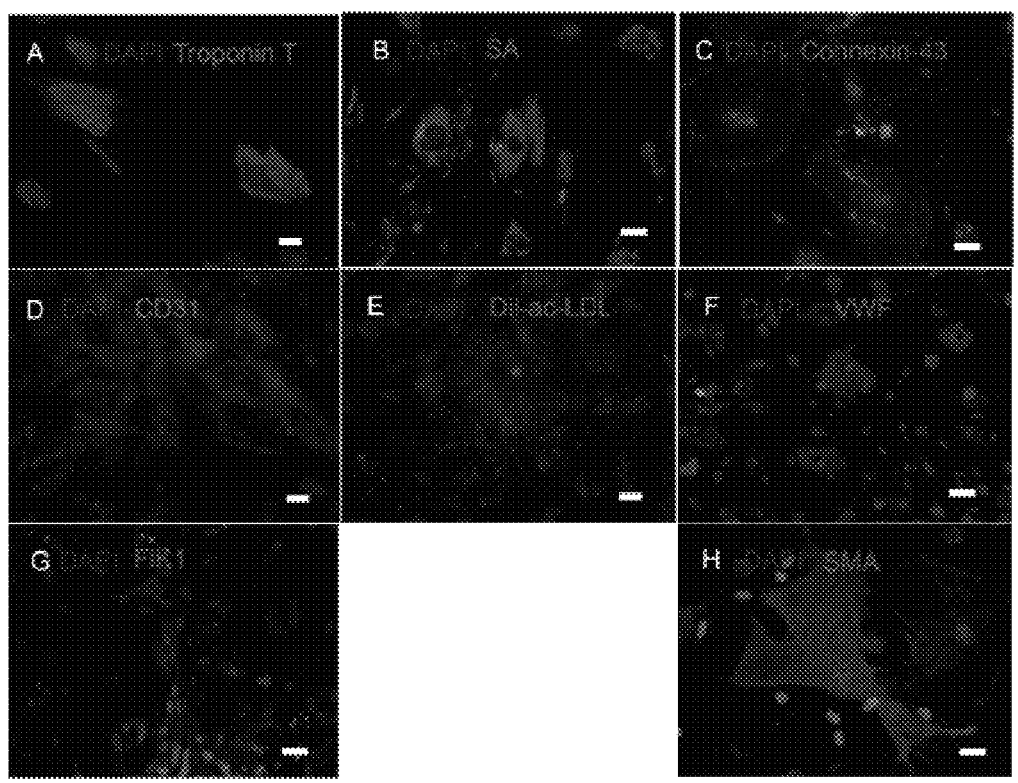
FIG. 8: Cloned Sca-1+CD45− cells differentiate into cardiac cells in vitro.

After treatment with 5-azacytidine, transforming growth factor β1 (TGF-β1), and vitamin C, cloned Sca-1$^+$CD45− cells at 4 and 20 passages differentiated into cardiomyocytes (~25% of cells expressed sarcomeric α actinin (SA) (FIG. 8B), and ~60% of cells expressed connexin-43 (FIG. 8C), the first connexin to be expressed in developing cardiomyocytes. Alternatively, treatment with by vascular endothelial growth factor (VEGF) resulted in differentiation into endothelial cells (~20% of cells expressed CD$_{31}$, Von Willebrand Factor (VWF), and FLK-1, and accumulated acetylated low density lipoprotein labeled with 1,1'-dioctadecyl-3,3,3',3'-tetramethylindo-carbocyanine perchlorate (Dil-acLDL)) and smooth muscle cells (~34% of cells expressed SMA) (FIGS. 8D, E, F, G and H). Thus, the Sca-1+CD$_{45}$− cells within CSs were clonogenic, multipotent (i.e., formed cardiomyocytes, endothelial cells, and smooth muscle cells), and were capable of long-term self-renewal in vitro, all characteristics of cardiac progenitor cells.

To determine whether Isl1 expression persisted in clonally expanded Sca-1$^+$CD45− cells, we compared Isl1 transcript levels between primary Sca-1$^+$CD45− isolates, clonally expanded Sca-1$^+$CD45− cells, and cardiomyocytes differentiated from Sca-1$^+$CD45− clones by real-time RT-PCR. We found that expression of Isl1 was not significantly different between primary Sca-1$^+$CD45− cells and cloned cells. However, Isl1 expression decreased in cardiomyocytes, consistent with differentiation beyond the progenitor stage (FIG. 3C).

Figure 9:
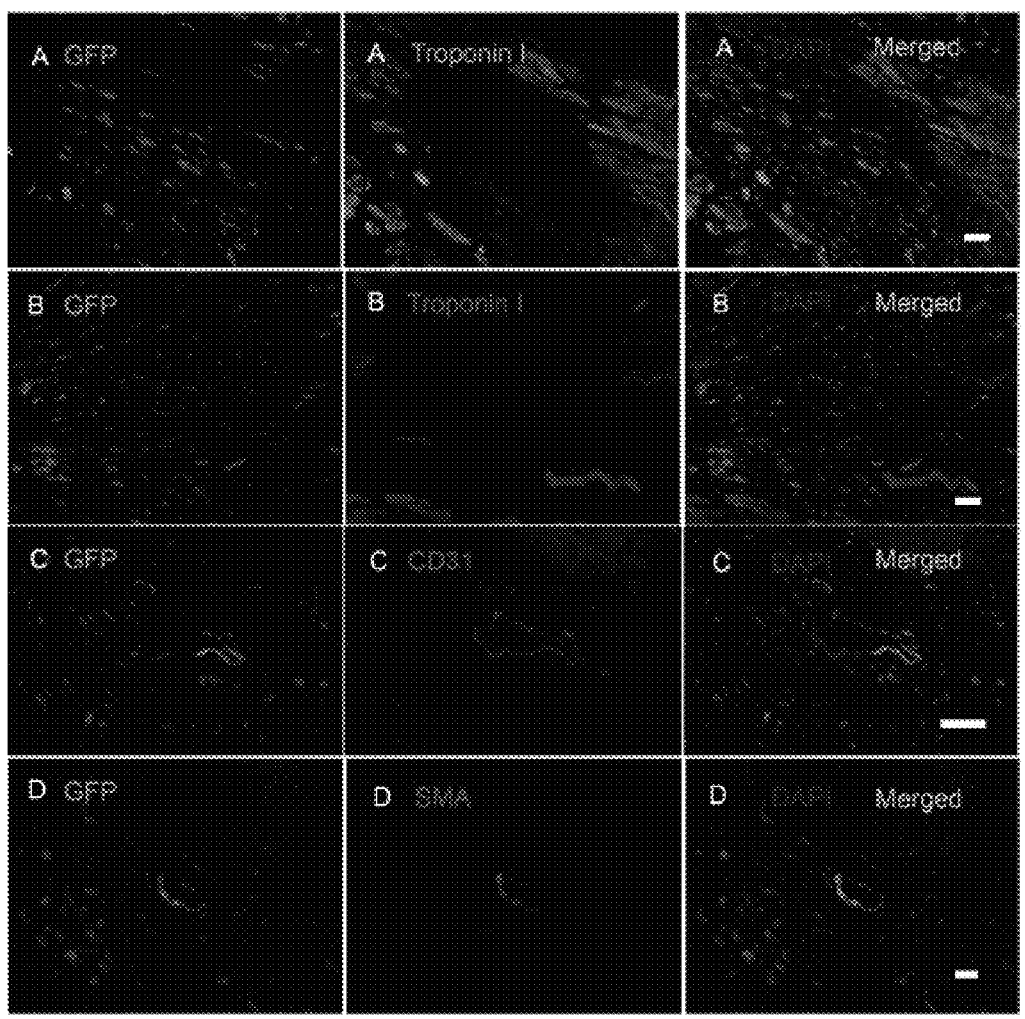
FIG. 9: Cloned Sca-1+CD45− cells differentiate into endothelial and smooth muscle cells in vivo.

Transplanted Sca-1+CD45− Cells Differentiate into Endothelial and Smooth Muscle Cells In Vivo To determine whether cloned Sca-1$^+$CD45− cells can differentiate after implantation in vivo, we injected 10$^6$ dissociated cloned GFP+Sca-1$^+$CD45− cells into the PZ of syngeneic wild-type mice 3 days post-MI. Twenty five days after injection, the hearts showed numerous implanted cells present in the PZ, but none of the injected cells had differentiated into cardiomyocytes (FIG. 9A), endothelial cells and smooth muscle cells at this early time-point after implantation. In contrast, hearts harvested 75 days after cell injection showed that ~10% of retained transplanted GFP+ cells differentiated into CD31+ endothelial cells (FIG. 9C) or SMA+ smooth muscle cells (FIG. 9D), but not troponin I+ cardiomyocytes (FIG. 9B). These findings demonstrate that the cloned Sca-1+CD45− cells not only survived in the ischemic microenvironment at 75 days post-injection, but also differentiated into two vascular lineages in vivo.

To quantify the level of engraftment and persistence of injected cells in infarcted hearts, cloned Sca-1+CD45− (GFP+) cells were injected into infarcted hearts of wild type mice. The injected hearts were harvested at 1 hour and 1, 3, 7, 14 and 25 days post-injection. RNA was isolated from whole heart and mRNA expression of GFP was quantified by real-time RT-PCR as a surrogate for the number of engrafted cells. The expression level of GFP in the heart collected 1 hour post-injection was used to represent 100% of injected cells. Approximately 15% and 4% of injected cells were detected in injected heart 3 and 7 days post-injection respectively. Approximately 3% of injected cells were detected 14 to 25 days post-injection.

Cloned Sca-1+CD45− Cells Promote Angiogenesis in Ischemic Myocardium

Figure 10:
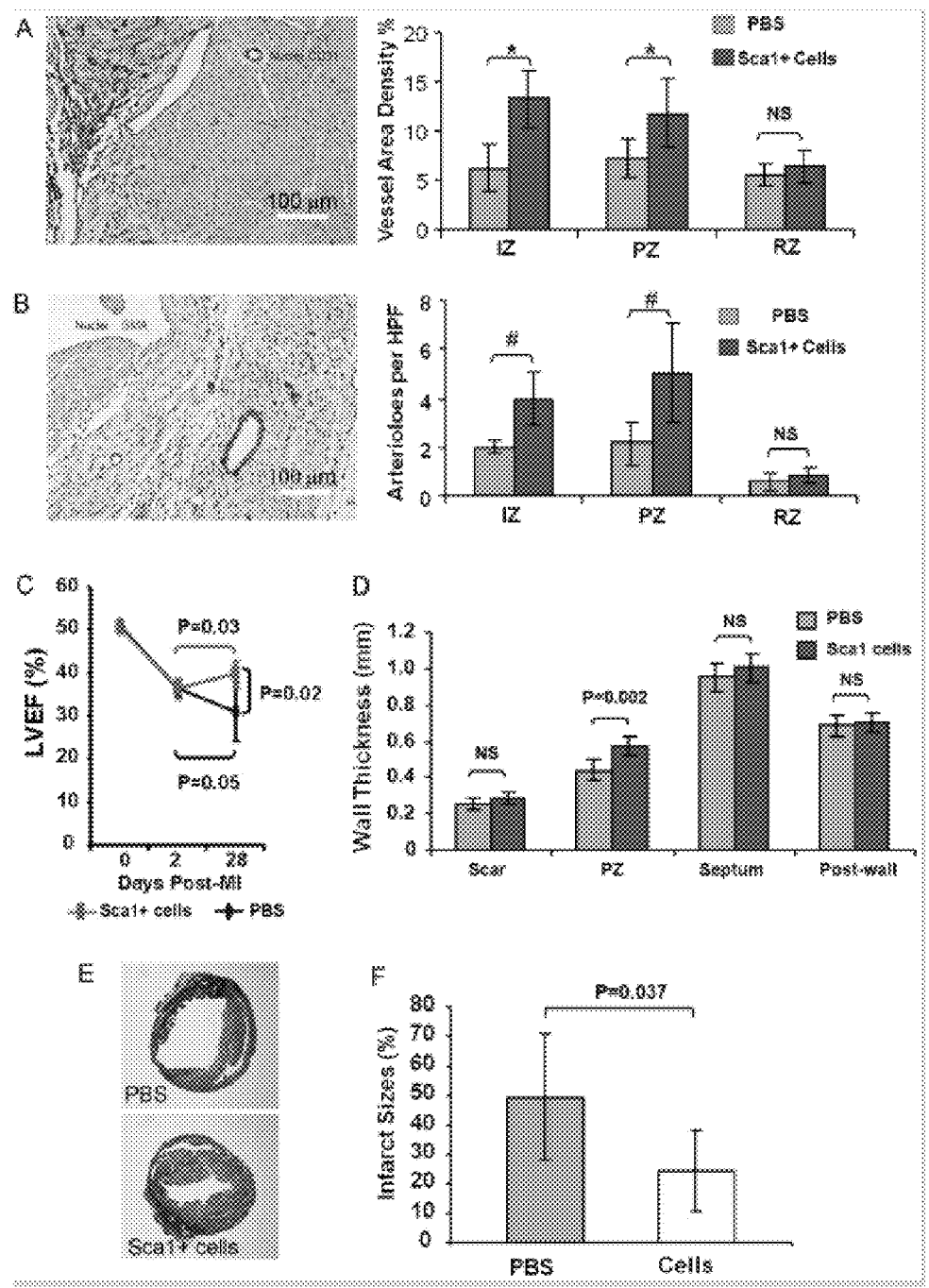
FIG. 10: Injected Sca-1+CD45− cells promote angiogenesis, limit infarct size and improve cardiac function.

To determine whether transplantation of cloned Sca-1$^+$CD45− cells promote angiogenesis in ischemic myocardium, we quantified the capillary and arteriole density in hearts 25 days after cell-injection. The results showed that there were more CD31+ vessels at the IZ (13.2±2.9% vs. 6.2±2.4%, P=0.001) and PZ (11.7±3.6% vs. 7.2±1.9%, P=0.02) in the cell-injected group vs. control (FIG. 10A). Moreover, the cell-injected group had a significantly higher number of SMA+ arterioles in the IZ (3.9±1.1 vs. 1.9±0.3/HPF, P=0.001) and PZ (5.0±2.0 vs. 2.1±0.9/HPF, P=0.009) vs. control (FIG. 10B). Cell-injection had no effect on vascular density in the RZ (CD31+ vessels: 6.4±1.7% vs. 5.7±1.1%, P>0.05; SMA+ arterioles 0.8±0.3 vs. 0.7±0.3/HPF, P>0.05) (FIG. 10A, B). However, none of the vessels contained GFP+ cells 25 days after cell-injection, suggesting that cloned Sca-1+CD45− cells promoted endogenous angiogenesis by paracrine mechanisms, rather than by direct participation in new blood vessel formation at this time point. Together, it is likely that transplanted cloned Sca-1+CD45− cells induce angiogenesis through both paracrine effects and transdifferentiation. However, the small number of vessels with GFP+ cells detected 75 days post-transplantation suggests that angiogenesis is induced mainly through paracrine effects of the engrafted cells.

Cloned Sca-1+CD45− Cells Reduce Apoptosis of Cardiomyocytes

Figure 17:
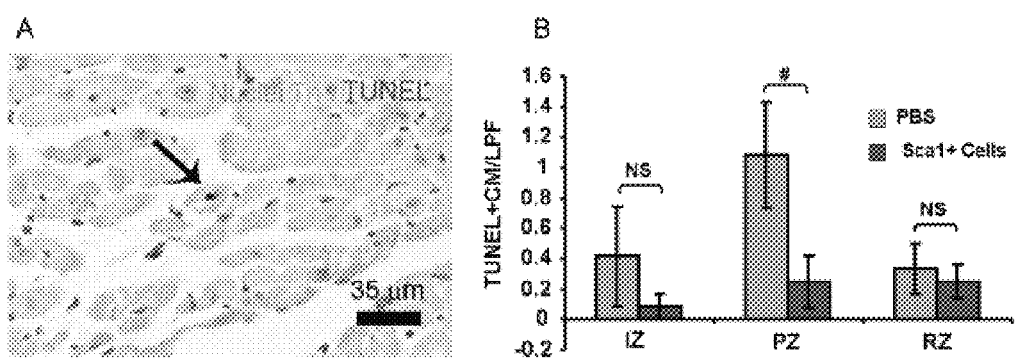
FIG. 17: Injected Sca-1+CD45− cells reduce cardiomyocyte apoptosis. Typical image showed TUNEL+/Troponin I+ cells (black arrow) (A). Sca-1+ cell injection resulted in a significant reduction of TUNEL+/Troponin I+ cells in the peri-infarct zone (PZ), but not in the infarct zone (IZ) and remote zone (RZ) compared to the control group 25 days post-injection (B). TnI, troponin I; TUNEL, terminal deoxynucleotidyl transferase dUTP nick end labeling; CM, cardiomyocyte; LPF, low power field (20× magnification); Data are shown as mean±SEM (N=6). #<0.05.

To evaluate the effects of Sca-1+CD45− cells injection on cardiomyocyte apoptosis, we used terminal deoxynucleotidyl transferase dUTP nick end labeling (TUNEL) and co-staining troponin I in the hearts 25 days after cell-injection. Cell injection resulted in significant reduction in the number of TUNEL+/troponin I+ cells in PZ compared to control (0.25±0.17 vs. 1.08±0.35/low power field (LPF), P<0.05) (FIG. 17). The number of TUNEL+/troponin I+ cells did not differ between cell-injected and control groups in IZ and RZ (FIG. 17).

Cloned Sca-1+CD45− Cells Reduce Infarct Size and Improve Cardiac Function

To determine whether the cloned Sca-1+CD45− cells alone improve cardiac function in the MI mouse model, we evaluated LVEF by echocardiography and measured infarct size by histochemistry 25 days after cell injection. LVEF was significantly reduced from an average of 51.2±1.5% before MI to 36.3±2.0% at 2 days post-MI in both groups, with no significant difference between the two groups (P=0.9). At 28 days post-MI (25 days post-injection), LVEF was significantly higher in the cell-injected group compared to control (39.7±3.2% versus 30.9±6.6%, P=0.02) (FIG. 10C). In addition, the myocardium was significantly thicker in the peri-infarct wall in the cell injected group compared to control (0.57±0.05 vs. 0.44±0.06 mm, P=0.002), but there was no statistically significant difference in the thickness of the posterior wall (0.70±0.05 vs. 0.69±0.06 mm, P=N.S.), septum (1.0±0.08 vs. 0.95±0.08 mm, P=N.S.) or scar (0.29±0.03 vs. 0.25±0.03 mm, P=N.S.) between the groups (FIG. 10D). The cell-injected group had significantly smaller infarcts compared to control (24.4±13.8% vs. 49.4±21.5%, P=0.037) (FIG. 10E, D). These studies show that the cloned Sca-1$^+$CD45− cells confer the therapeutic benefits of CSs in the mouse MI model.

Figure 32:
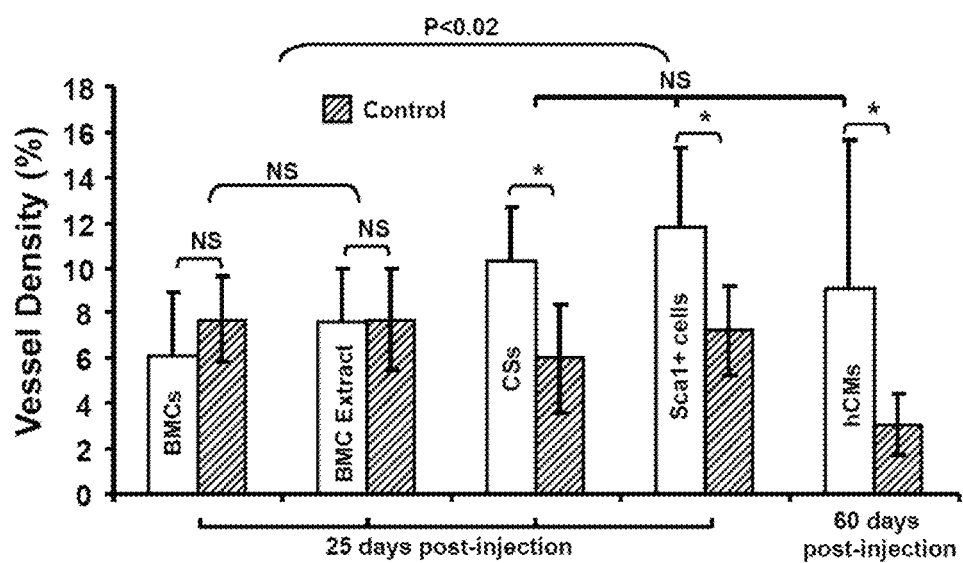
FIG. 32: Change of vessel density at peri-infarct zone after injection of indicated cells

Comparison of Effect of Various Cells Injected into Murine Infarcted Hearts (See Also FIG. 32)

3) transplanted CSs from infarcted myocardium engraft in ischemic myocardium, improve cardiac function, and promote endogenous angiogenesis; 4) adult heart contains Isl1+ cells and Isl1 expression in CSs is 17-fold higher than in total adult cardiac tissue; 5) Isl1 expression in the Sca-1+CD45− subpopulation within CSs is 3-fold higher than in total CSs; 6) Sca-1+CD45− cells in CSs can be cloned, expanded, and have the characteristics of multipotent cardiac progenitor cells in vitro; and 7) after injection into ischemic myocardium, cloned Sca-1+CD45− cells not only survive long-term, but also differentiate into endothelial and smooth muscle cells, promote endogenous angiogenesis, reduce cardiomyocyte apoptosis, reduce infarct size, and improve cardiac function. Of special note, these experiments have been performed in middle-aged mice, rather than in young adults, to simulate a more clinically relevant disease model.

Rhe number of Sca-1+ cardiac progenitor cells increases post-MI. Our data agrees with these reports and further shows that the potential for CSs generation in vitro is highly time dependent post-MI. The number of CSs from 1- and 2-week post-MI hearts greatly increases compared to uninjured hearts, and this increase is attenuated by 4 weeks post-MI. This suggests that acute MI induces the proliferation of cardiac progenitor cells, and this increase in proliferation gradually dissipates over a 4-week period post-MI. Therefore early acquisition of tissue from post-MI hearts can facilitate higher yields of CSs in vitro. However, the optimal timing in humans may be different than the ones reported in our study and future research is necessary to better define the ideal timing of tissue acquisition in patients post-MI.

Stem cell niches distribute preferentially to the apex and atria of the heart, where the wall stress is relatively low. MI may affect their distribution. Our results show that various regions of 1-week post-MI hearts have similar abilities to produce CSs. This suggests that although MI mainly affects the LV, the CS-forming cells throughout the heart are

| Cells | Origin | Recipient | Cell# injected/ Heart | Cells engraft 25 d post-injection | LVEF improved 25 d post-injection | Reduce infarct size post-injection | Induce angiogenesis post-injection |
|---|---|---|---|---|---|---|---|
| BMCs | 2.5 months C57BL mice | 2.5 months C57BL mice | $10^6$ | No | Yes | Yes | 3 day post-injection |
| BMC extract | 2.5 month C57BL mice | 2.5 months C57BL mice | $10^6$ | No | Yes | Yes | 3 day post-injection |
| CSs | 9 month C57 BL mice | 2.5 months C57BL mice | $10^5$ | Yes | Yes | Yes | 25 day post-injection |
| Sca-1+ cells from CSs | 9 month C57 BL mice | 2.5 months C57BL mice | $10^6$ | Yes | Yes | Yes | 25 day post-injection |
| hESCs derived CMs | Human ESCs | 3 months SCID mice | $10^6$ | No | Yes | Yes | 60 day post-injection |

In this study, we have shown that: 1) there is a significant increase in the proliferative capacity of CS-forming cells isolated from the "middle aged" heart following acute MI resulting in a significant rise in the number of CSs in vitro; 2) this increase is time-dependent and is most pronounced within the first week post-MI in the animal model studied;

activated post-MI. As such, taking tissue from any region of the heart appears to yield similar numbers of CSs per unit of tissue. The mechanism by which MI increases CSs production is worthy of further investigation. Importantly, the septum and right ventricle yield the same numbers of CSs. Thus, percutaneous right ventricular endomyocardial biopsy, as is performed routinely for other clinical indications, could potentially be used to generate CSs in the post-MI setting.

CSs from non-infarcted hearts can differentiate into cardiac cells and preserve cardiac function. Whether CSs derived from early stage post-MI hearts have the same abilities has not been demonstrated until now. Our results show for the first time that the CS cells obtained from 1-week post-MI hearts engraft in ischemic myocardium and restore cardiac function at 25 days post-injection in vivo. However, we did not find evidence for differentiation of these cells into mature cardiomyocytes or new vessels. Our data demonstrate that the injected CSs promoted angiogenesis in vivo, suggesting that engrafted CSs cells likely have a paracrine, pro-angiogenic effect in the ischemic myocardium. Secreted VEGF from engrafted CSs may contribute to angiogenesis in the infarcted hearts. This paracrine effect may play an important role in attenuating adverse LV remodeling and preserving cardiac function.

Isl1+ cells can be found in adult mouse, rat and human hearts. Our results not only confirm the presence of Isl1+ cells in adult murine hearts, but we show that these can be efficiently isolated and expanded by culturing Sca-1+CD45− cells from CSs. Since Isl1 is not expressed on the cell surface, it has been difficult to isolate and purify these cells by immune selection. However, we now demonstrate that isolating Sca-1+CD45− cells from CSs results in an enriched population of Isl1+ cardiac progenitors for autologous cardiac cell-therapy.

While cloned Sca-1+CD45− cells improved cardiac function post-MI in transplanted mice, we did not find evidence for differentiation of these cells into cardiomyocytes in vivo. One possible explanation is that the cloned Sca-1+CD45− cells may need a longer time to differentiate into cardiomyocytes in situ. This is supported by the observation that there was no differentiation seen from cloned cells in the first 25 days, while endothelial and smooth muscle cell differentiation occurred only after 75 days. Another possible explanation is that there may be subpopulations of Sca-1+ CD45− CS cells with distinct differentiation capacities. The therapeutic effects of CS-derived Sca-1+CD45− cells in vivo suggest that these cells might be responsible for the overall effects of CSs. Since the Sca-1+CD45− cells can be clonally expanded in vitro, they provide a feasible approach to rapidly generating therapeutic quantities of cardiac progenitor cells.

CSs are known to be composed of fibroblasts. Although many fibroblasts grow out from the cardiac explant during the first stage of culture, we have demonstrated that CSs as described herein contain cardiac progenitor cells that are capable of clonal expansion and multi-lineage cardiac differentiation. Furthermore, our demonstration that cloned Sca-1+CD45− cells have a beneficial therapeutic effect, similar to heterogeneous CSs, argues strongly against the hypothesis that fibroblasts are the major contributors to cardiac repair in CSs.

We have demonstrated that Sca-1+CD45− cells derived from cardiospheres do indeed have "progenitor" characteristics given their ability to differentiate into other cell types both in vivo and in vitro. Second, we show increased angiogenesis and reduced cardiomyocyte apoptosis after injection of cloned Sca-1+CD45− cells. Recently, using a genetic lineage mapping approach, Loffredo et al. (28) have reported new cardiomyocyte formation in infarcted hearts derived from endogenous cardiac stem cells 8 weeks after injecting with murine bone marrow c-kit+ cells. There are several possible explanations for the consistent improvements in ventricular function including: reduction in cardiomyocyte apoptosis, prevention of infarct scar expansion by mechanically stiffening the infarct zone, facilitation of hypertrophy of the border zone cardiomyocytes by enhanced angiogenesis. Endogenous adult cardiomyocytes can be stimulated to re-enter cell cycle, divide, and recruit and/or activate resident cardiac progenitors. Each of these mechanisms has been implicated in improved cardiac function seen with cell therapy.

In summary, our data shows that the cloned Sca-1+CD45− cells derived from CSs from post-MI hearts are enriched in Isl1+ progenitors, have the characteristics of progenitor cells, and are source of autologous cells for myocardial therapy.

Materials and Methods

C57BL/6J mice and C57BL/6J GFP transgenic mice with chicken α-actin promoter driving EGFP expression were purchased from the Jackson Laboratory (Bar Harbor, Me.).

Myocardial Infarction Model

Nine month-old, male C57BL/6J mice were used for all experiments to simulate "middle-aged" subjects. Mice underwent total permanent ligation of the left anterior descending coronary artery (LAD) to induce MI, and hearts were collected 1, 2, and 4 weeks post-MI (n=6/group). Hearts were also harvested from animals that had undergone sham operation or no surgery (n=6/group). The surgical procedure for MI has been previously described (29, 33, 34). Briefly, mice were anesthetized using isoflurane, intubated and ventilated. A midline thoracotomy incision was made to expose the heart for surgery. LAD was ligated permanently. Sham operation was performed by passing a suture under the LAD and removing it without ligation.

Generating Chimeric Mouse

Bone marrow cells were harvested from 8-10 week old GFP transgenic mice and transplanted into lethally irradiated (9.5 Gy) 2 month-old C57BL/6 mice through tail vein injection ($2 \times 10^6$ nucleated unfractionated cells per mouse). The expression of GFP by peripheral blood mononuclear cells was analyzed by FACS 5-6 months later. CSs were isolated from no-surgery or 2-week post-MI hearts of chimeric mice.

Cell Transplant Studies

Nine month-old, male C57BL/6J GFP transgenic mice (n=12) were used as CSs donors. One week post-MI, hearts were harvested and used to generate CSs for injection. CSs were dissociated into single cell suspension by Blendzyme 4 and resuspended with phosphate buffered saline (PBS). Alternatively, cloned Sca-1+CD45− cells were dissociated into single cell suspension by trypsin and also resuspended with PBS. These cells in 10 μl PBS were injected into the hearts of 3-day post-MI mice by ultrasound-guided injection, a technique developed and reported by our laboratory (29, 34). PBS only was injected into infarcted hearts as control. Two month-old, wild-type C57BL/6J mice were used as recipients. The recipient mice received either CS cells (n=7), cloned Sca-1+CD45− cells (n=8) or PBS (n=12), and hearts were harvested 25 days post-injection or 75 days post-injection (Sca-1+CD45− cell injections only). For studying the retention of injected cloned Sca-1+CD45− cells, eighteen wild-type mice were used as recipients and whole hearts were harvested 1 hour and 1, 3, 7, 14 and 25 days post-injection (n=3/each time point) for RNA isolation.

Cardiosphere Culture

CSs were generated using the method described by Messina et al. (7) with some modification. The whole heart was removed from the mice and cut into 1-2 mm³ pieces. After being washed with Ca++Mg++ free PBS and digested three times, 5 minutes each at 37° C. with 0.25% trypsin (Invitrogen, Carlsbad, Calif.) and 0.1% collagenase D (Roche Diagnostics, Indianapolis, Ind.), the tissue pieces were cultured as "explants" on fibronectin (Sigma, St Louis, Mo.) coated 6-well plates, 2 wells for each heart in IMDM medium with 10% FBS and 0.1 mM β-mercaptoethanol at 370 C with 5% $CO_2$. A layer of fibroblast-like cells grew from explants, over which small, round phase-bright cells (CS-forming cells) appeared 2 to 4 weeks after initiating the culture. Once the fibroblast-like cells grew to 90% confluence determined visually, the cells surrounding the explants were harvested by two washes with PBS, one wash with 0.53 mmol/L EDTA and one wash with 0.05% trypsin (Invitrogen) at room temperature. The harvested cells were filtered by 70 mm cell strainer (BD Biosciences, San Jose, Calif.), and then cultured at a density of $1 \times 10^5$ cells/ml in each well of 24-well plates coated with Poly-D-Lysine (BD Biosciences) in cardiosphere growth medium (CGM), which included 35% IMDM, 65% DMEM-F12, 3.5% FBS, 0.1 mM β-mercaptoethanol, 2% B27 (Invitrogen), 10 ng/ml EGF (R&D systems), 20 ng/ml bFGF (R&D systems), 40 nmol/L thrombin (R&D systems) and 4 nmol/L cardiotrophin (R&D systems). The number of CSs in each well was counted on the $7^{th}$ days after the CS-forming cells were plated.

Flow Cytometry and Cells Sorting

CSs were dissociated into single cell suspension by Blendzyme 4 (5.6 U/ml) (Roche). The following phycoerythrin (PE) or allophycocyanin (APC) conjugated rat anti-mouse antibodies and conjugated isotype-matched control antibodies were used: Sca-1-PE, c-kit-PE, CD133-PE, CD34-PE, CD45-APC, Flk-1-APC and CD31-APC (eBioscience). The cells were incubated with antibodies for 25 min on ice, washed with PBS containing 0.2% BSA, and analyzed by FACSCabilur with CellQuest software (BD Biosciences).

For cell sorting, the dissociated CS cells from hearts of 1-week post-MI GFP transgenic mice were stained by the following antibodies: Sca-1–PE and CD45–APC. The Sca-1+CD45– cells were sorted by FACSAria with FACSdiva software (BD Biosciences) and were dropped into a 96-well plate, one cell/well, on top of mitomycin-C treated murine embryonic fibroblast cells (Millipore, N.J.). The cells were then cultured with CGM at 37° C. with 5% $CO_2$. For isolating RNA, sorted Sca-1+CD45– cells or CD45+ cells from CSs were collected into a tube with 1 ml of CGM respectively.

Directed Differentiation In Vitro

Cloned Sca-1+CD45– cells were loaded into chamberslides coated with gelatin at 15,000 cells/cm² in differentiation medium, treated by 5-Azacytidine (5 mM) for 3 days, and then we added TGF-β1 (1 ng/ml) and vitamin C (0.1 mM) for three weeks to induce cardiomyocyte differentiation (18). The cells were treated with VEGF (20 ng/ml) in IMDM medium with 10% FBS for 2 weeks for endothelial and smooth muscle cells differentiation (18).

Immunocytochemistry

The cells cultured in chamberslides were washed with PBS, fixed with cold methanol for 5 min or 4% paraformaldehyde/PBS for 15 min, and blocked with Dako antibody diluent (Dako Cytomation, Carpinteria, Calif.) for 1 hour. When using mouse derived monoclonal antibody, we also used Rodent Block M (Biocare Medical, Concord, Calif.) blocking for 30 min. The cells were incubated with the following primary antibodies diluted in Dako antibody diluent at 40 C overnight: rabbit anti-Nkx2-5, GATA4 (Santa Cruz Biotechnology, Santa Cruz, Calif.), mouse anti-Isl1 (39.4D5) (Developmental Studies Hybridoma Bank, Iowa City, Iowa), mouse anti-α SMA (Sigma), mouse anti-Troponin T (Thermo Fisher Scientific, Fremont, Calif.), mouse anti-SA (Abcam, Cambridge, Mass.), rabbit anti-connexin-43 (Sigma), mouse anti-$CD_{31}$ (Abcam) and rabbit anti-VWF (Abcam). The cells were then incubated with the Alexa Fluor 546 labeled goat anti-rabbit antibody or goat anti-mouse antibody (Invitrogen) at room temperature for 1 hour. The slides were mounted with ProLong Gold antifade reagent with DAPI (Invitrogen) and viewed with a Nikon E800 fluorescence microscope using Openlab software (Improvision, Lexington, Mass.).

Acetylated-LDL Uptake Assay

Acetylated low density lipoprotein labeled with Dil-ac-LDL (Invitrogen) was added into the medium with cells at 2 μg/ml as final concentration and incubated at 37° C. with 5% $CO_2$ for 1 hour. The medium was removed. The cells were washed with PBS and fixed with 4% paraformaldehyde/PBS for 15 min. The slides were mounted and viewed same as immunocytochemical staining.

RT-PCR and Real-Time RT-PCR

The total RNA from CSs and tissues were isolated by TRIzol reagent (Invitrogen). cDNA was generated from 0.3 μg of total RNA by using SuperScript III First-Strand Synthesis kit (Invitrogen). RT-PCR was performed using 1 μl of cDNA and Advantage 2 PCR kit (Clontech, Mountain View, Calif.) with the following program: 95° C. for 3 min, (95° C. for 30 s, 68° C. for 3 min)$_{x30}$ cycles, 68° C. for 10 min. PCR products were separated on 2% agarose gel. Every pair of PCR primers was designed to span one or several introns to distinguish the signals amplified from genomic DNA contamination. The primers sequence of Nkx2-5, GATA4, Flk-1, SMA and internal control hypoxanthine phosphoribosyltransferase (HPRT) are from previous publications (4, 35, 36).

The total RNA from sorted cells was isolated and the cDNA was generated by Taqman Gene Expression Cells-to-Ct kit (Applied Biosystems, Foster City, Calif., USA). The primers and probe for murine Isl1 and HPRT were purchased from Applied Biosystems. The real-time PCR were performed by ABI PRISM 7300 (Applied Biosystems) using Taqman Master Mix (Applied Biosystems) in duplicates and the average threshold cycles (CT) of duplicate were used to calculate the relative value of Isl1 in different cells and tissues. The CT for HPRT was used to normalize the samples. Expression of Isl1 mRNA relative to HPRT mRNA was calculated based on the CT, $\Delta CT_{LIsl1} = CT_{Isl1} - CT_{HPRT}$. The relative values of Isl1 were calculated as $2^{-\Delta CTIsl1}$.

For studying the retention of injected cloned GFP+Sca-1+CD45– cells, total RNA from whole heart was isolated by TRIzol, genomic DNA was removed from total RNA by RNeasy Mini Kit with RNase-free DNase (Qiagen) and 25 ng cDNA was used for real-time PCR. The sequences of primers and probes for GFP and histone 3.3A were as previously published (29). Expression of GFP mRNA relative to histone 3.3A mRNA was calculated based on the CT, $\Delta CT_{GFP} = CT_{GFP} - CT_{histone}$. The relative values of GFP were calculated as $2^{-\Delta CTGFP}$.

Tissue Analysis

Tissue was analyzed by two blinded reviewers. Mice were sacrificed 25 days post-injection of cells (28 days post-MI) or 75 day post-injection. The hearts were arrested in diastole with KCl, perfusion and fixed with 10% formalin, embedded in paraffin, cut into 5 mm sections and blocked with Dako antibody diluent for 1 hour. When using mouse or rat derived monoclonal antibody, we also incubated the sections with Rodent Block M or R blocking for 30 min. To detect GFP and troponin I double positive cells, sections were stained with anti-troponin I (Abcam) and rabbit anti-GFP (Invitrogen) overnight at 4° C. Alexa Fluor 546 goat anti mouse IgG and Alexa Fluor 660 goat anti rabbit IgG were used as secondary antibodies (Invitrogen). Detection of GFP and CD31 double-positive cells were stained with rat anti-CD31 (Biocare Medical) and Alexa Fluor 546 goat anti-rat IgG were used as secondary antibodies. GFP and α-SMA double positive cells were stained with mouse anti-α-SMA and without prior antigen retrieval but otherwise followed the steps described above. The slides were mounted with Pro-Long Gold antifade reagent with DAPI and viewed with a Nikon E800 fluorescence microscope using Openlab software.

In order to assess vascular density in the hearts, the sections from mid-ventricular level were stained by antibodies of rat anti-CD31 and mouse anti-α-SMA at room temperature for 1-2 hours. A CD31 signal was detected using a Rat on Mouse HRP-Polymer kit (Biocare) and 3,3' Diaminobenzidine (DAB) (Biocare). An α-SMA signal was detected by a MM AP-Polymer kit (Biocare) and a Vulcan Fast Red Chromogen kit (Biocare) for color development. The slides were mounted and observed as described above. ImagePro Plus 6.0 software (MediaCybernetics, Bethesda, Md.) was used to analyze the percentage area occupied by CD31 positive vessels. The number of arterioles, defined as vessels with CD31+ endothelial cells surrounded by α-SMA+ smooth muscle cells, per HPF in each region was counted (29).

For Isl1 staining, the hearts were perfused and fixed with 4% paraformaldehyde overnight, equilibrated with 20-30% sucrose and frozen in OCT for tissue sectioning using a cryostat. The sections were blocked with Rodent Block M and Dako antibody diluent for 30 min respectively, stained with mouse anti-Isl1 (39.4D5) overnight at 4° C. and Alexa Fluor 546 goat anti-mouse IgG used as secondary antibody.

TUNEL staining was performed with ApopTag® Plus Peroxidase In Situ Apoptosis Detection Kit (Chemicon, Temecula, Calif.) according to the manufacture's protocol and DAB was used for color development. For co-staining troponin I, the sections from mid-ventricular level were treated with denature solution (Biocare), blocked with Rodent Block M and then incubated with mouse anti-troponin I. The mouse-on-mouse alkaline phosphatase polymer (Biocare) was used as secondary antibody. Vulcan Fast Red Chromogen kit was used for color development. Finally the sections were counterstained with hematoxylin. TUNEL-positive cardiomyocytes were defined by the presence of both DAB nuclear staining and completely surrounded by troponin I staining.

In order to assess the size of infarct scar, the sections from mid-ventricular level (mid-papillary) were stained by picosirius red. The scar was stained as dark red. The slides were mounted and viewed same as above. All histological sections were examined with a Nikon Eclipse E800 microscope using a 1× objective with the use of Openlab software (Improvision, Lexington, Mass.). To assess the circumferential extent of the infarct, the epicardial and endocardial infarct lengths, epicardial and endocardial circumferences of LV were traced manually using the ImagePro Plus 6.0 software. Epicardial infarct ratio was obtained by dividing the epicardial infarct length by the epicardial circumference of LV. Endocardial infarct ratio was calculated by dividing the endocardial infarct length by the endocardial circumference of LV. The circumferential extent of the infarct scar was calculated as [(epicardial infarct ratio+endocardial infarct ratio)/2]×100.

Echocardiography

Echocardiography was accomplished under isoflurane anesthesia with the use of a Vevo-660 (VisualSonic, Toronto) equipped with a 30 MHz transducer. Echocardiograms were obtained at baseline, 2 days post-MI (before injection), and day 28 post-MI. We measured LVEF and wall thickness. Wall thickness was measured at the apical anterior wall (infarct wall thickness) and at the mid-anterior segment (peri-infarct wall thickness) separately on the parasternal long-axis view; posterior wall thickness was obtained at the papillary muscle level. Three cycles were measured for each assessment and average values were obtained (29, 33). Echocardiograms were analyzed by a blinded reviewer.

Statistical Analysis

One way ANOVA with Fisher's post hoc test was used to analyze the difference among multiple groups. Student's t-test was used to analyze differences between two groups. Values were expressed as mean±SD unless otherwise specified, with $P<0.05$ considered significant. SPSS 15.0 software was used to conduct all statistical analysis.

REFERENCES

1. Bergmann O et al., *Science,* 2009; 324:98-102.
2. Beltrami A P et al., *Cell,* 2003; 114:763-776.
3. Oh H et al., *Proc Natl Acad Sci USA.,* 2003; 100:12313-12318.
4. Matsuura K et al., *J Biol. Chem.,* 2004; 279:11384-11391.
5. Bu L et al., *Nature.* 2009; 460:113-117.
6. Laugwitz K L et al., *Nature.* 2005; 433:647-653.
7. Messina E et al., *Circ Res.,* 2004; 95:911-921.
8. Smith R R et al., *Circulation.* 2007; 115:896-908.
9. Tang Y L et al., *Biochem Biophys Res Commun.,* 2007; 359:877-883.
10. Barile L et al. *Cardiac stem cells: isolation, expansion and experimental use for myocardial regeneration;* 2007 February pp. S9-S14.
11. Barile L et al., *Prog Cardiovasc Dis.,* 2007; 50:31-48.
12. Boyle A J et al., *Circulation.* 2006; 114:339-352.
13. Andersen D C et al., *Stem Cells.* 2009; 27:1571-1581.
14. Zaruba M M et al., *Circulation.* 2010; 121:1992-2000.
15. Cai C L et al., *Dev Cell.* 2003; 5:877-889.
16. Khattar P et al., *Stem Cells Dev.,* 2011; 20:1043-1052.
17. Smart N et al., *Nature.* 2011; 474:640-644.
18. Smits A M et al., *Nat. Protoc.,* 2009; 4:232-243.
19. Delorme B et al., *Circ Res.,* 1997; 81:423-437.
20. Wang X et al., *Stem Cells.* 2006; 24:1779-1788.
21. Urbanek K et al., *Proc Natl Acad Sci USA.,* 2006; 103:9226-9231.
22. Chimenti I et al., *Circ Res.,* 2010; 106:971-980.
23. Genead R et al., *Stem Cells Dev.,* 2010; 19:1601-1615.
24. Itzhaki-Alfia A et al., *Circulation.* 2009; 120:2559-2566.
25. D'Alessandro D A et al., *Circ Res.* 2009; 105:1128-1140.
26. Fischer K M et al., *Circulation.* 2009; 120:2077-2087.
27. Tang X L et al., *Circulation.* 2010; 121:293-305.
28. Loffredo F S, Steinhauser M L, Gannon J, Lee R T, *Cell Stem Cell.* 2011; 8:389-398.
29. Yeghiazarians Y et al., *Mol. Ther.,* 2009; 17:1250-1256.
30. Yeghiazarians Y et al., Cytotherapy in press. 2011.

Example 2

Hydrogels Promote Survival and Neovascular Integration of Transplanted Cardioprogenitor Cells Introduction Several technological challenges and relevant cell transplantation parameters must be considered before cell transplantation can become widely viable. For example, immediately after transplantation into damaged tissue, donor cells encounter a harsh environment with substantial death-promoting stimuli (e.g., hypoxia, reactive oxygen species, etc.). For therapies designed to repair damaged tissue, in particular, post myocardial infarction (MI) cardiac tissue, the vast majority of donor cells are lost to necrosis and/or apoptosis within hours to days after transplantation. General consensus has been that the ability of cell transplantation therapies to promote tissue regeneration is limited to trophic paracrine signaling and occurs only during a short temporal therapeutic window. Yet cell transplantation yields an empirical functional improvement to their host tissues. Provided herein are methods and compositions for improving cell survival after transplantation that enhance therapeutic effect by prolonging the window of paracrine trophic signaling and improve engraftment of donor cells.

One strategy for improving the survival of implanted cells, termed Matrix-Assisted Cell Transplantation (MACT), is to engineer an environment that exposes the donor cells to prosurvival signaling immediately after transplantation and promotes mechanisms of engraftment with the host tissues. Matrigel™ was initially proposed as a material for MACT, but heterogeneous batch-to-batch material composition has led to significant problems in establishing consistent data. Additional work has focused on naturally occurring biopolymers such as collagen, alginate, fibrin, chitosan, and HyA. Ideally, a material for MACT would exploit the prosurvival potential of naturally occurring biopolymers and also allow for a wide design space to modulate parameters that are relevant in the native extracellular matrix, including cell-surface receptor ligands, growth factor sequestration, and mechanical properties.

To overcome the limitations associated with MACT, we have developed tunable, artificial extracellular matrixes for use in cellular transplantation procedures. HyA was selected as the primary component of this structural matrix since it plays a crucial role in regulating angiogenesis by stimulating cytokine secretion and endothelial cell (EC) proliferation, as well as being biocompatible, biodegradable, non-immunogenic, and playing critical role in fostering tissue development and repair. After chemical modification to functionalize HyA by the addition of acrylate side groups, conjugation of peptides to promote cell adhesion and heparin domains to sequester growth factors was achieved by exploiting the Michael-type addition reaction with thiols presented from terminal cysteines on either the peptides or proteins. The same reaction was used with thiol-terminated crosslinkers to generate hydrogels with tunable mechanical properties.

Using this easily tunable hydrogel, we sought to demonstrate how a suitable material for MACT can support donor cell survival during transplantation and encourage integration into the host tissue. In this study, we focused on murine cardiac progenitor cells (CPCs), a pluripotent population of GFP+Sca-1+/CD45− cells that contribute to cardiac regeneration, at least in part by undergoing neovascular differentiation that is characteristic of endothelial cells. With this versatile cell type, we examined how the biochemical and mechanical parameters of the HyA hydrogels influenced: (1) CPC survival, proliferation, and differentiation in vitro; and, (2) CPC survival and functional integration via neovascularization in vivo.

Results

Figure 20:
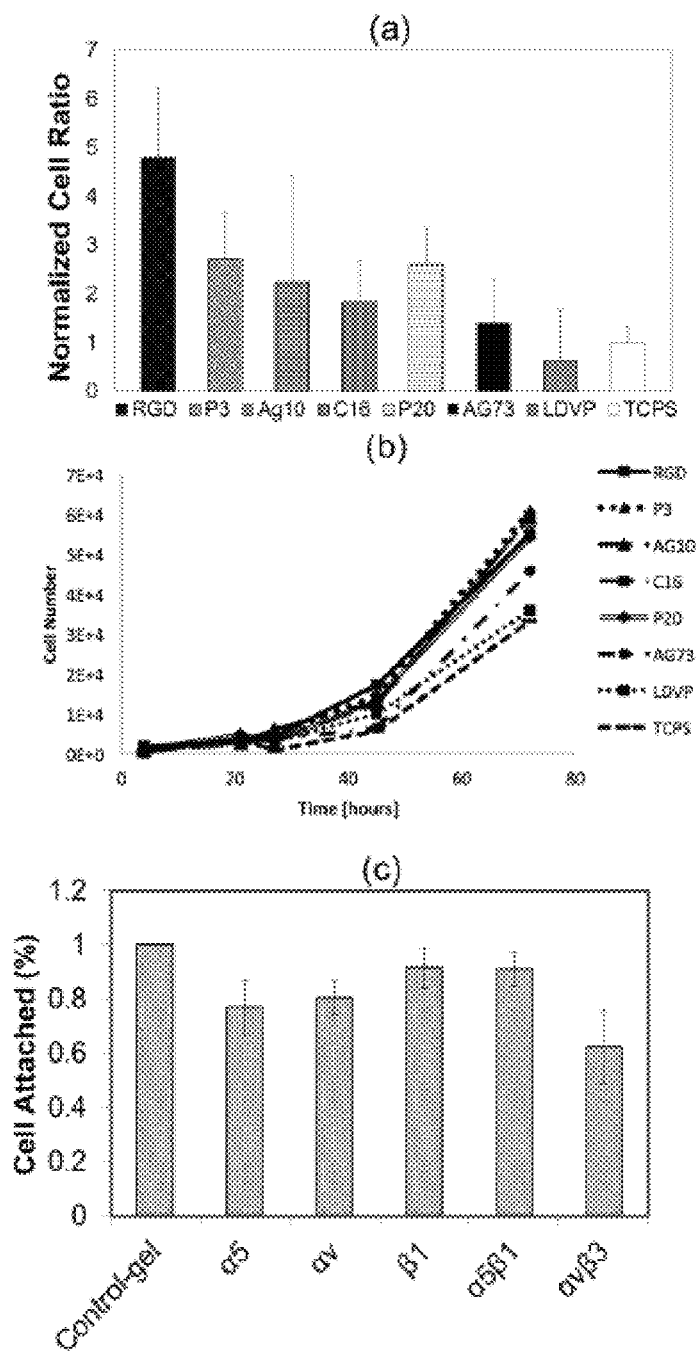
FIG. 20: bspRGD(15) adhesion peptides enhances CPC function. Adhesion peptides CGGNGEPRGDTYRAY (bspRGD; SEQ ID NO:1), CGGNRWHSIYITRFG (AG-10; SEQ ID NO:2), CGGEILDVPST (LDVP; SEQ ID NO:3), CGGRKRLQVQLSIRT (AG73; SEQ ID NO:4), and CGG-KAFDITYVRLKF (C16; SEQ ID NO:5), RNIAEIIKDIGC (P20; SEQ ID NO:6), CGGVSWFSRHRYSPFAVS (P3; SEQ ID NO:7) were evaluated to determine which sequences provided the greatest (a) cellular adhesion and (b) proliferation of the CPCs. bspRGD(15) was capable of maximizing both functions, and (c) its significance was validated using blocking antibodies for various integrins, as blocking αvβ3 resulted in the greatest loss in adhesion function.

Defined Material Parameters were Achieved Using Acrylated HyA (AcHyA) Hydrogel Synthesis For this study, two discrete hydrogel components were synthesized (see FIGS. 18 and 19 for detailed synthesis and characterization of AcHyA components): AcHyA conjugated with the adhesion peptide bspRGD(15) (AcHyA-RGD) and AcHyA conjugated with the glycosaminoglycan heparin (AcHyA-Heparin). The adhesion peptide was chosen based on a screen of seven peptides with known integrin engagement for both adhesion and proliferation (FIG. 20). TGFβ1 was added to AcHyA-Heparin and up to 95% of the growth factor was sequestered by the heparin via the protein's heparin-binding domain (i.e., AcHyA-Heparin-TGFβ1), which was dependent on the weight percentage of heparin (FIG. 19B). These functionalized AcHyA components were combined at defined ratios (FIG. 21a), and then in situ crosslinking of the HyA hydrogel was achieved via the Michael-type addition reaction with short peptide sequences presenting terminal cysteine residues (FIG. 21b) to generate hydrogels over a range of biochemical and physical parameters.

TABLE

| Range of hydrogel parameters evaluated in this study | |
|---|---|
| HyA Hydrogel Parameters | Range of values evaluated |
| bspRGD(15) peptide density | 120-380 μM |
| crosslinking density peptide density | 25%-100% |
| HyA weight percentage | 1-3 wt % HyA (15-850 Pa) |
| heparin weigh density | 0.01-0.03 wt % |
| TGFβ1 concentration | 40 nM |

Gelation of the hydrogel was initiated after approximately 60 seconds and was completed within 15 min, as determined by measuring a time-sweep of its mechanical response to 0.1% strain at 1 Hz using an oscillatory rheometer (FIG. 21c). The viscoelastic properties of the resulting hydrogel were dependent on both the weight percentage of AcHyA and the crosslinking density, which was defined as the moles of available cysteines on the peptide crosslinker relative to the moles of acrylate groups on the AcHyA (FIG. 22). The retention kinetic of TGFβ1 within the hydrogel was measured over 20 days and was dependent on the weight percentage of the incorporated heparin. At the end of this period, as much as 75% of the TGFβ1, relative to the initial concentration, was retained within the hydrogel (FIG. 21d).

CPC Adhesion and Proliferation was Dependent on the AcHyA Hydrogel Parameters

To evaluate the effect of each AcHyA component on CPC function, four combinations of HyA hydrogels were synthesized: (1) AcHyA only, (2) AcHyA and AcHyA-RGD, (3) AcHyA, AcHyA-RGD and AcHyA-Heparin, and (4) AcHyA, AcHyA-RGD and AcHyA-Heparin-TGFβ1 (i.e., HyA, HyA-P, HyA-PH and HyA-PHT; see Table below for the concentration ranges used for each of these components).

TABLE

Synthesis parameters for typical AcHyA hydrogel components

|  | HyA | HyA-P | HyA-PH | HyA-PHT | HyA-P + TGFβ1 |
|---|---|---|---|---|---|
| AcHyA 3 wt % HyA* | 8 mg | 2 mg | 2 mg | 2 mg | 2 mg |
| AcHyA-RGD 3 wt % HyA* 380 uM RGD* | — | 6 mg | 6 mg | 6 mg | 6 mg |
| Heparin-SH | — | — | 0.03 wt % | 0.03 wt % | — |
| TGFβ1 | — | — | — | 40 nM | 40 nM |
| Peptide Cross linker | 9 μM | 9 μM | 9 μM | 9 μM | 9 μM |

Figure 23:
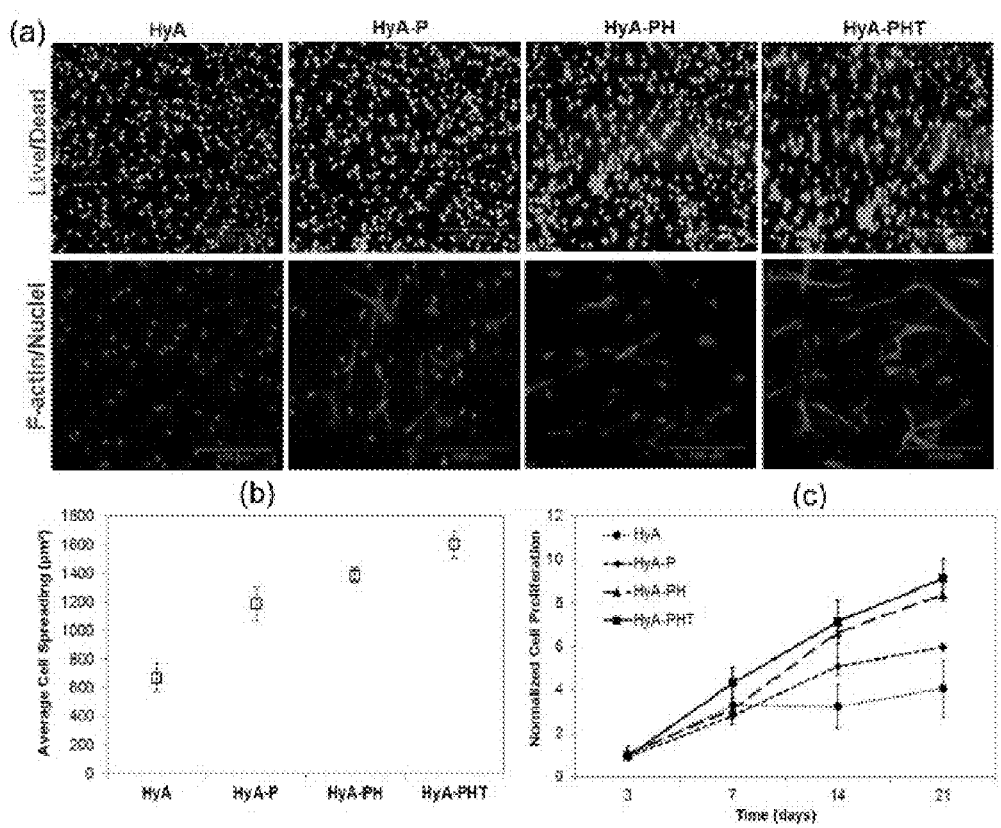
FIG. 23: CPC Viability, proliferation, and adhesion in HyA hydrogels. (a, upper panels) The viability of CPCs encapsulated by the HyA-, HyA-P, HyA-PH and HyA-PHT hydrogels was high after one day of culture, as assessed by double staining with calcein (live cells) and propidium iodide (dead cells). (a, lower panels) CPCs were capable of adhering and spreading within the hydrogel networks containing the adhesive ligand bspRGD(15), as assessed by imaging for f-actin stress fibers (TRITC-phalloidin) and nuclei (DAPI). (b) The area of spread cells was enhanced significantly by the addition of adhesion peptide and TGFβ1; (c) Cell proliferation within the HyA hydrogels was affected by the presence of heparin and TGFβ1, and at day 21, proliferation in both HyA and HyA-P were significantly less than HyA-PH and HyA-PHT hydrogels (ANOVA with Tukey, p<0.05).

Minimal (<5%) CPC death was observed in each of the hydrogels, independent of the combination of components (FIG. 23a). After 3 days of culture, cell adhesion and morphology within the matrices were observed by visualizing the filamentous actin (FIG. 23b). CPCs seeded within all three hydrogels containing AcHyA-RGD exhibited robust spreading and elongated cellular morphology, whereas CPCs seeded in the hydrogel containing only HyA remained rounded and did not assume a typical adherent cell morphology. We calculated the area of CPC spreading in the hydrogels and found the cells in HyA-PHT spread the most (1600 μm2). However, the relative difference in cell area for any of the hydrogels containing AcHyA-RGD was small compared to the area of rounded cells in the HyA hydrogel (660 μm$^2$, FIG. 23c).

Figure 24:
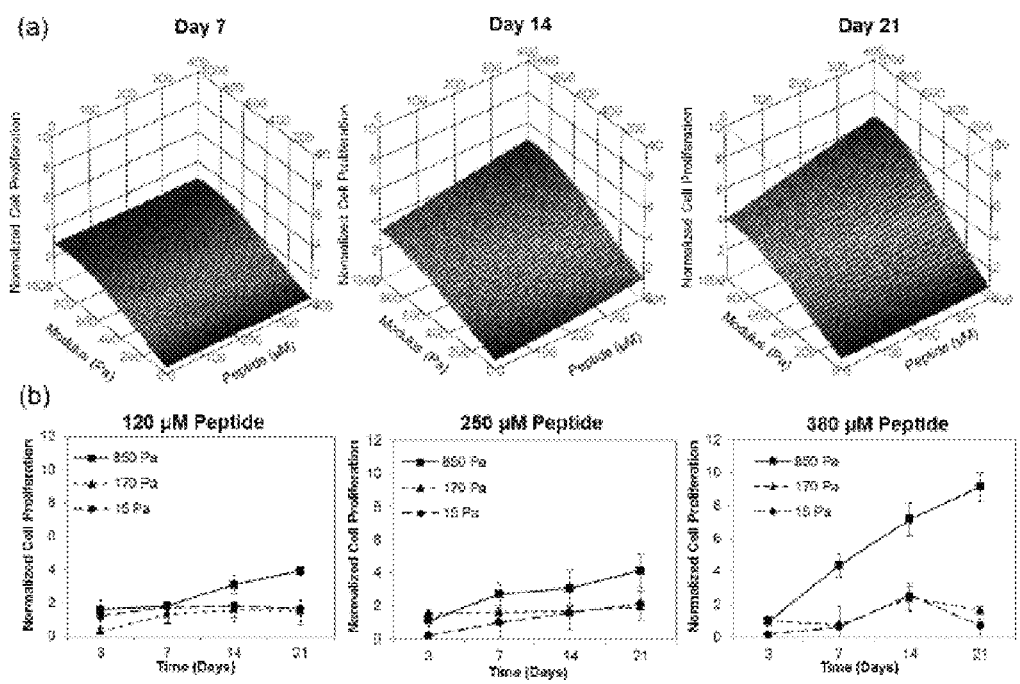
FIG. 24: Dependency of cell proliferation on hydrogel stiffness and adhesion peptide density. (a) RSM plots of CPC proliferation in HyA-PHT hydrogels containing various weight percentages of HyA precursors (1-3 wt %) and concentrations of the cell adhesive ligand bspRGD(15) (120-380 μM). CPC proliferation was dose-dependent on the RGD density, and plateaued at ~800 Pa. All data was normalized to the cell number in HyA hydrogels at day 3 data. (b) Kinetic observations of CPC proliferation as a function of hydrogel stiffness in HyA-PHT hydrogels shown at three different bspRGD(15) densities.

The proliferation of CPCs in the same four hydrogels was quantified over 21 days (FIG. 23d). Statistically, there was no significant difference between any of the gets at Days 3 and 7, and only marginal proliferation was observed in the HyA hydrogel through day 21. By contrast, CPCs proliferated consistently from day 3 to day 21 in all three hydrogels containing AcHyA-RGD (i.e., HyA, HyA-PH and HyA-PHT). At day 14, HyA was significantly less than HyA-PH and HyA-PHT, and at day 21, both HyA and HyA-P were significantly less than HyA-PH and HyA-PH ($p<0.05$). These results reveal that the additional AcHyA components with heparin and TGFβ1 enhanced the proliferation of CPCs. The effect of bspRGD(15) density and hydrogel stiffness on CPC proliferation was evaluated using response surface methodology (RSM) to analyze the multiparametric data (FIG. 24). CPC proliferation was linearly dependent on bspRGD(15) density within the range we evaluated, whereas the effect of hydrogel stiffness plateaued at approximately 800 Pa. Furthermore, the matrix stiffness had greater influence on the proliferation rate of the CPCs compared to peptide density, as the former appeared to dominate the response surfaces at every time point. The highest proliferation rate was found for 380 μM bspRGD(15) and modulus of 850 Pa, and unless otherwise noted, these parameters were used for all of the HyA gels throughout the remainder of the study.

Figures 25, 25A:
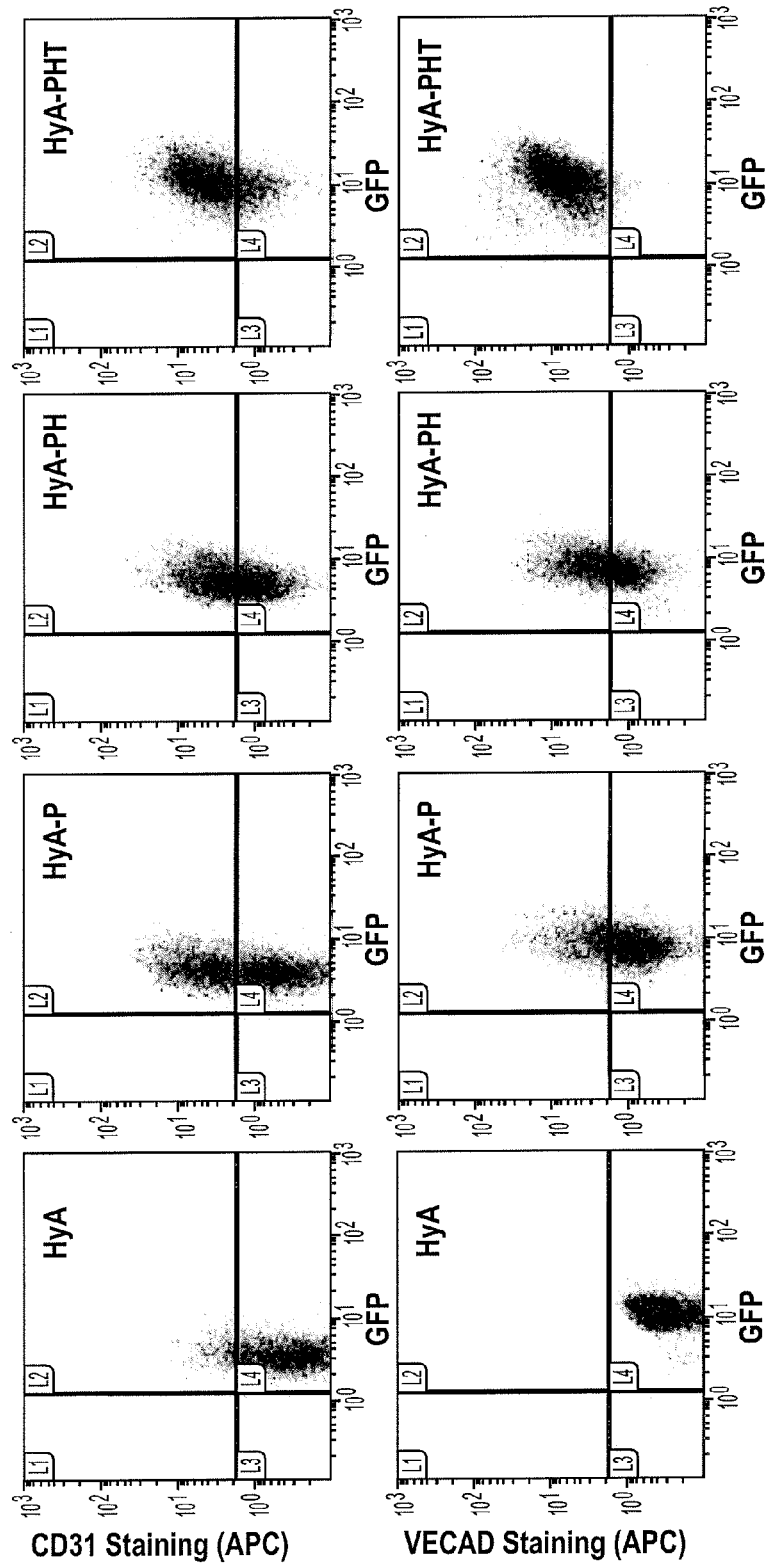
FIG. 25: Validation of endothelial cell differentiation. (a) Bivariate histograms are demonstrate differentiation of CPCs into ECs based on increasing CD31 and VE-cadherin expression in HyA, HyA-P, HyA-PH and HyA-PHT hydrogels. (b) CD31 and VE-cadherin expression by CPCs increased over time in HyA-PHT, which indicates the time-course of EC differentiation within this hydrogel.
Figures 25, 25B:
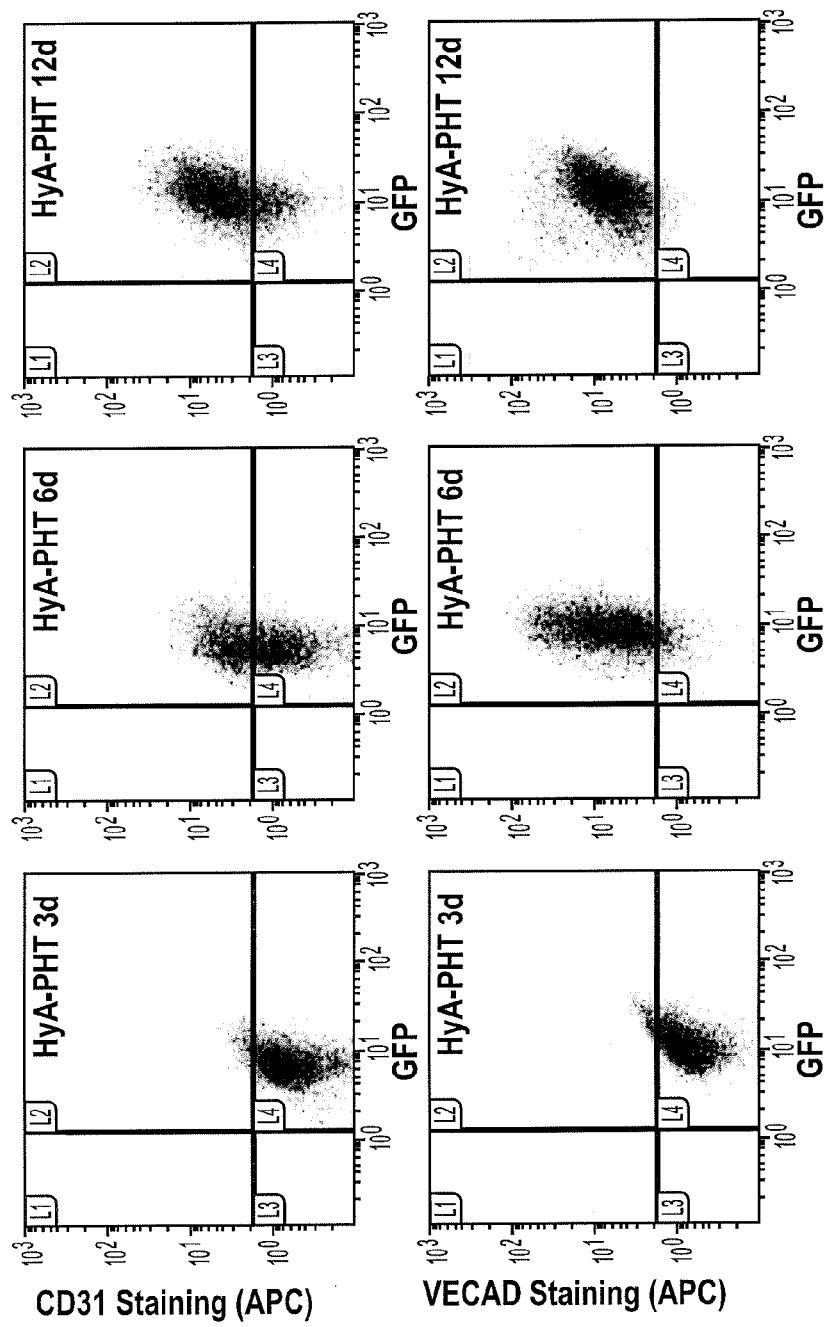
Figure 26:
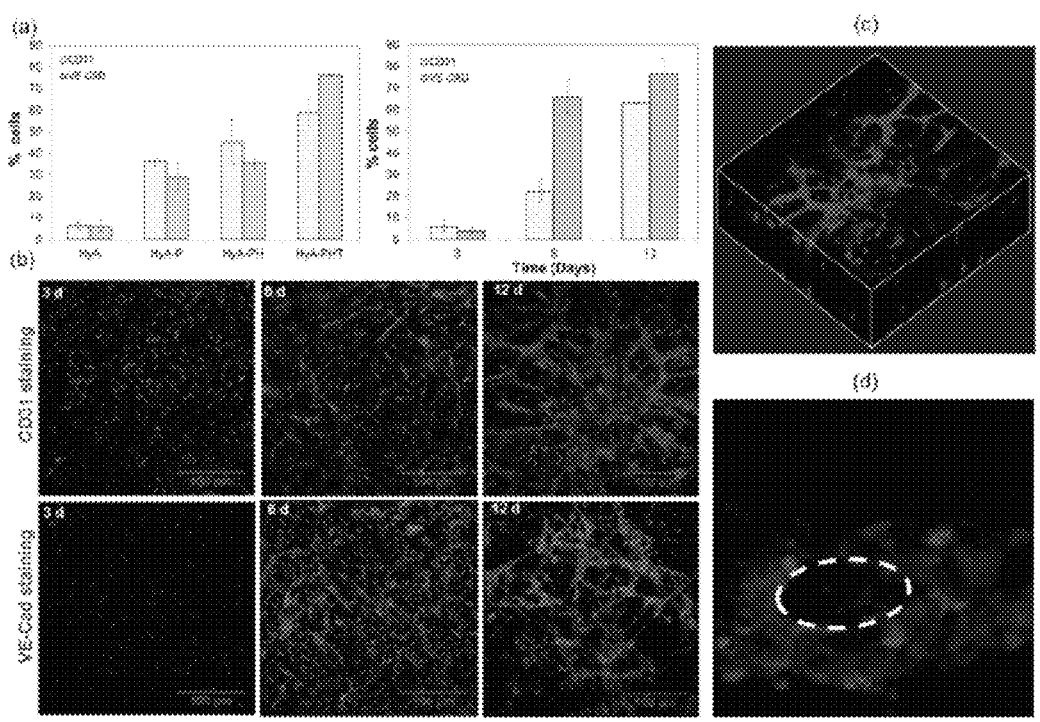
FIG. 26: CPCs differentiate into endothelial cells within the hydrogels. (a) The percentage of differentiated endothelial cells within the different HyA hydrogels expressing CD31 and VE-cadherin was quantitatively measured using flow cytometry. The time dependency of EC differentiation was also observed by measuring the expression of these cell surface markers over the 12 days following CPC seeding into the HyA-PHT hydrogels. (b) Endothelial cell differentiation in situ was assessed using immunocytochemistry to identify CD31 and VE-cadherin positive cells within the HyA-PHT hydrogels, where network structures resembling vascular morphology were observed within 12 days. (c) The 3D network structure of the CD31 positive cells and (d) the appearance of a central lumen within the network structures suggested they were hollow nascent vessels, e.g. tubular structures.

CPC Formation into Endothelial Networks could be Controlled Via AcHyA Hydrogel Parameters The Sca-1+/CD45− population of CPCs readily differentiate into endothelial cells under the appropriate induction conditions. In this study, CPC differentiation was measured by immunostaining for CD31 and VE-Cadherin, two EC-specific markers, followed by quantification by flow cytometery (see FIG. 25). All of the HyA gels containing bspRGD (15) significantly increased the expression of both EC markers ($p<0.05$: FIG. 26a). Inclusion of TGFβ1 increased the number of cells expressing CD31 relative to the HyA-P hydrogels, and it increased the number of cells expressing VE-cadherin relative to both the HyA-P and HyA-PH hydrogels. TGF β1 signaling was sufficient to induce the formation of a tubule network, which increased in density and complexity between days 6 and 12 (FIG. 26b). Interestingly, network formation was only observed in HyA-PHT hydrogels (see, FIG. 27), which indicated that neither the base HyA hydrogel matrix, bspRGD(15), nor heparin were sufficient to induce terminal differentiation of the CPCs into endothelial tubes. By comparison, the HyA-PHT hydrogels promoted the formation of network structures that were CD31+ and capable of acetylated low-density lipoprotein (Ac-LDL) uptake (FIG. 27), which is characteristic of fully-differentiated endothelial cells. These complex three-dimensional networks (FIG. 26c) contained a central lumen (FIG. 26d), suggesting that CPCs in the HyA-PHT hydrogels were capable of forming nascent vessels.

Figure 28:
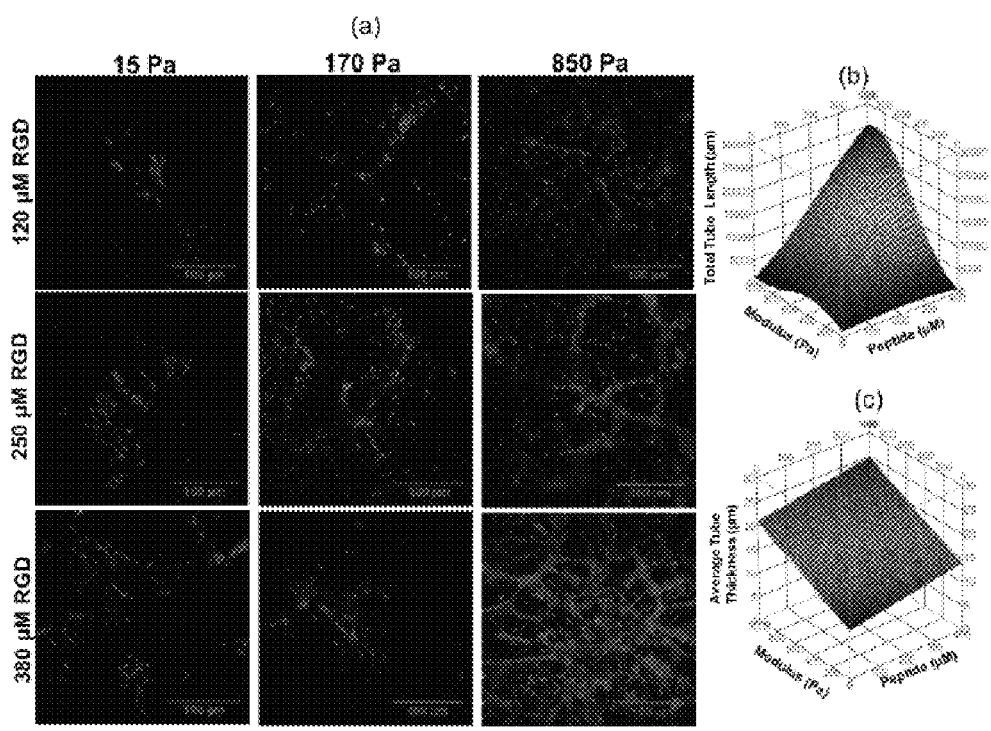
FIG. 28: Tube formation by CPCs was dependent on hydrogel stiffness and adhesion peptide density. (a) Vascular-like tube formation of CD31 positive cells in the HyA-PHT hydrogel was observed as a function of bspRGD(15) peptide density (120-380 μM) and gel modulus (15-850 Pa). RSM plots of the combined effects of peptide ligand and material modulus on (b) total tube length and (c) average tube thickness.

We next investigated the effect of HyA hydrogel stiffness and bspRGD(15) density on nascent endothelial tube formation. After culture for 12 days in HyA-PHT hydrogels, synthesized over a range of material parameters, CPC formation of tubular networks was dependent on both hydrogel modulus and peptide density (FIG. 28a). To quantify tube formation, we generated high-resolution, z-stack images of the differentiated CD31+ cells using 2P confocal microscopy. After analyzing the three-dimensional reconstructions, we generated response surfaces for total tube length and average tube thickness as a function of HyA-PHT modulus and adhesion peptide density (FIGS. 28b and 28c). The effect of the hydrogel modulus on total tubule length in the network appeared to reach a maximum at approximately 800 Pa, whereas the response of total tubule length to the bspRGD(15) peptide density was approximately linear within the range evaluated in this study. Similarly, the thickness of the tubules formed in HyA-PHT hydrogels exhibited a linear response to both hydrogel modulus and bspRGD(15) peptide density, although this tubule characteristic was more sensitive to the matrix stiffness parameter.

Figure 29:
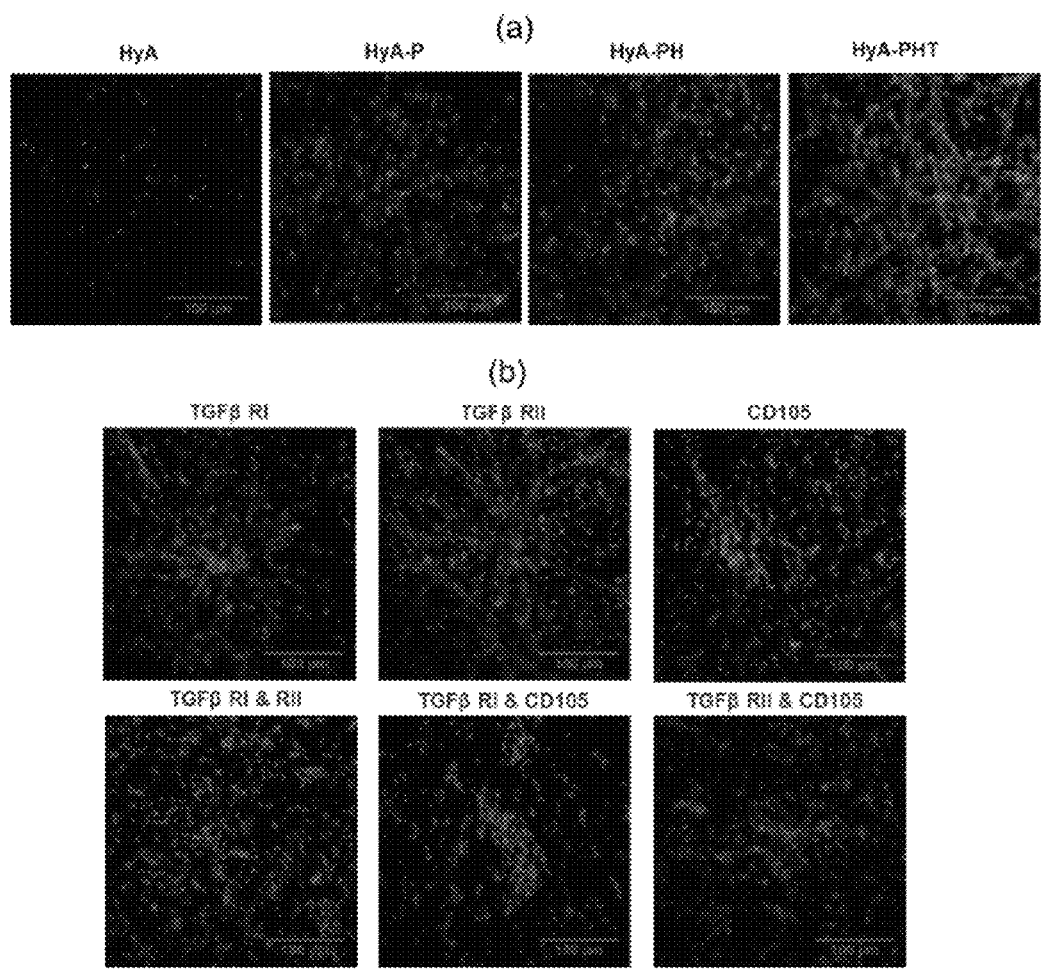
FIG. 29: Dependency of CPC tube formation on the TGFβ1 treatment. (a) Expression of CD105 (endoglin), a TGFβ1 coreceptor, was dependent on the inclusion of bspRGD(15) adhesion peptide in the HyA hydrogels. Addition of TGFβ1 in the matrix enhanced the CD105 expression. (b). CD31+CPCs were imaged 12 days after seeing in HyA-PHT hydrogels with blocking antibodies for either TGFβ receptor I, TGFβ receptor II, endoglin (CD105) or for two of these receptors in combination. Blocking either TGFβ receptor I or TGFβ3 receptor II allowed some tube formation, whereas blocking CD105 provided equivalent inhibition of tube formation as blocking both TGFβ receptor I and TGFβ receptor II simultaneously.

To further understand the mechanism, we investigated the interaction of TGFβ1 with the TGFβ receptors I and II in conjunction with the CD105/endoglin receptor known to direct the fate of vascular network forming endothelial cells. We first determined via flow cytometry that 80% of the CPC population was CD105+, and these cells readily differentiated into endothelial cells in vitro in the HyA-P hydrogels, but their most robust expression was in the HyA-PHT gels (FIG. 29a). Since endoglin/CD105 interacts with the TGFβ receptors (TGFβR1 and TGFβR2) to promote terminal endothelial differentiation via mechanisms associated with tubulogenesis and capillary stability (32), we interrupted TGFβ1 signaling in the HyA-PHT using neutralizing antibodies for TGFβR1, TGFβR2 and CD105 to determine their role in the CPC differentiation (FIG. 29b) Inhibiting CD105 resulted in a reduction in tube formation, and the simultaneous inhibition of CD105 and either of the TGFβR1 or TGFβR2 completely abrogated tubulogenesis. Inhibition of both TGFβR1 or TGFβR2 also reduced tube formation. Collectively these data indicate the TGFβ-induced terminal differentiation of CPCs within the HyA-PHT hydrogels was CD105-dependent, which is a non-canonical pathway for TGFβ1, that activates a mitogenic response mediated by an increase in TGF-β1 induced ALK1 signaling.

Figure 27:
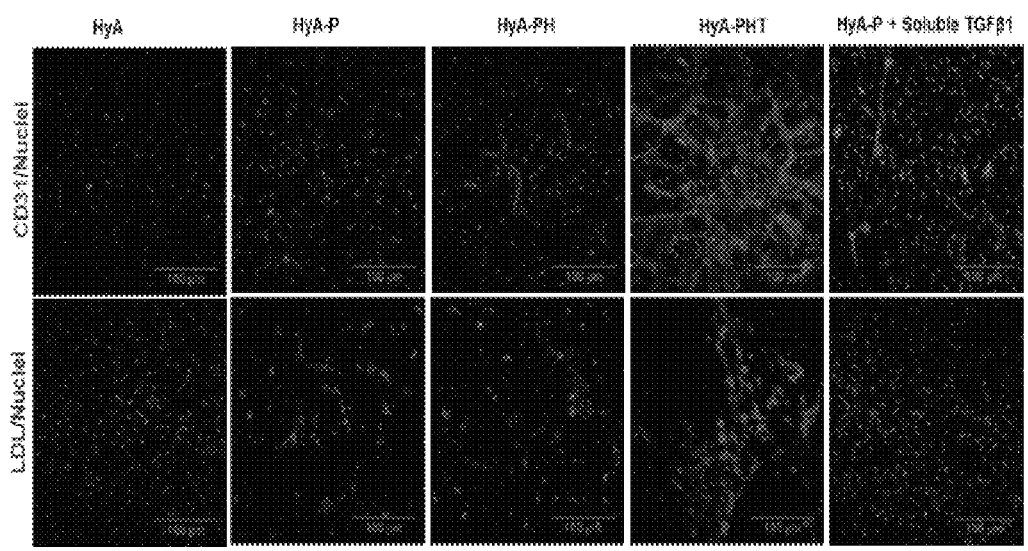
FIG. 27: Validation of endothelial cell differentiation. Representative confocal microscopy images of immunostaining of endothelial cell marker CD31, acetylated low density lipoprotein (Ac-LDL) uptake by the cells after 12 days of culture in HyA, HyA-P, HyA-PH and HyA-PHT hydrogel. We also included a HyA-P treated with an equivalent concentration of soluble TGFβ1 as delivered in HyA-PHT. Both TGFβ1 and heparin were necessary in the HyA hydrogels to promote endothelial cell differentiation, as determined by CD31 expression and Ac-LDL uptake, and tubule formation.
Figure 30:
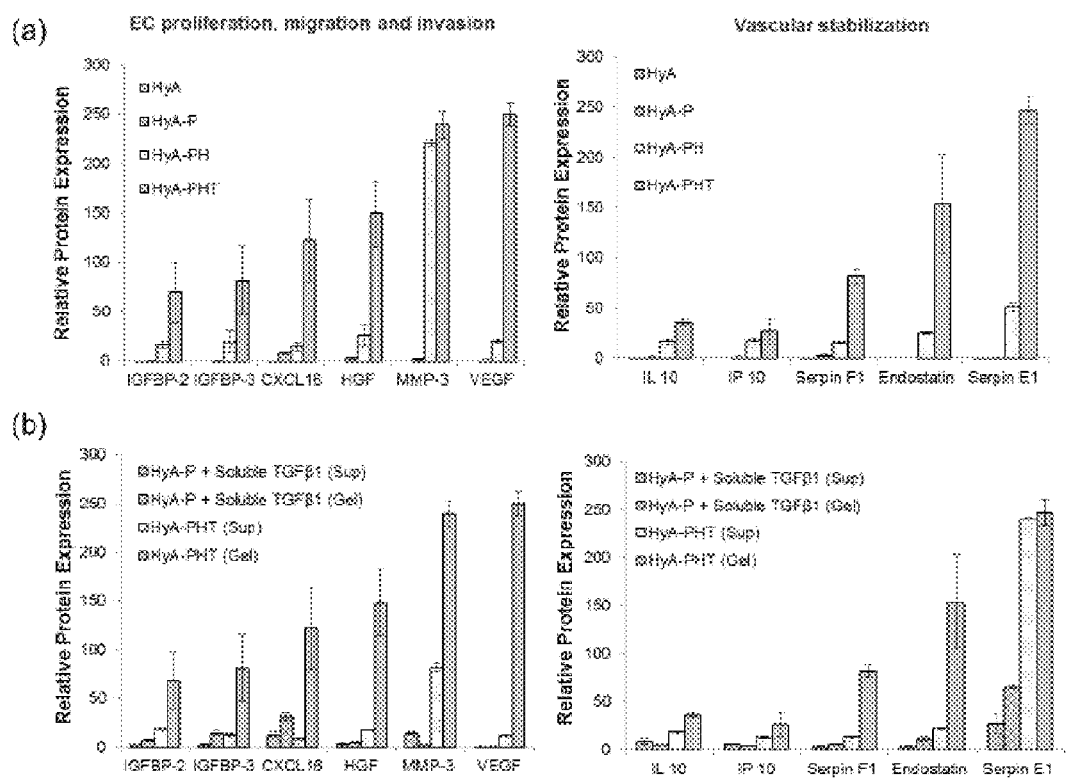
FIG. 30: HyA-PHT hydrogels encouraged angiogenic cytokine expression by CPCs. (a) The concentration of secreted angiogenic factors produced by CPCs and sequestered within HyA-PHT hydrogel after 12 days. These include factors that promote EC proliferation and those associated with vascular stability. (b) The presentation of TGFβ1 affected the production of angiogenic proteins, which were detected in the cell supernatant (Sup) and within the hydrogel (Gel). HyA hydrogels containing heparin-bound TGFβ1 demonstrated significant increases in expression of proteins associated with proliferation and vascular stability relative to identical hydrogels exposed to an equimolar concentration of TGFβ1, but without heparin.

Finally, the effect of AcHyA hydrogel components on CPC trophic function was investigated. CPCs were cultured for 12 days in the four HyA hydrogel combinations used previously (i.e., HyA, HyA-P, HyA-PH and HyA-PHT) and the concentration of secreted angiogenic paracrine factors retained by the hydrogel matrix were measured (FIG. 30). Only low paracrine factor expression was observed by CPCs entrained in any of the hydrogels without TGFβ1 exposure, and by contrast, the cells seeded in the HyA-PHT expressed high levels of paracrine factors that were associated with angiogenesis. Interestingly, the cells seeded in HyA-P and treated with soluble TGFβ1 also produced some paracrine factors, but only a limited subset relative to the HyA-PHT hydrogel and at lower expression levels in both the hydrogel and supernatant. In the absence of heparin, the differentiation of CPCs into ECs, as measured by CD31 expression and Ac-LDL uptake, and the formation of tubule structures was also diminished (FIG. 27). Taken together, these data suggest that HyA hydrogels can promote the trophic function of entrained CPCs, which depends not only on TGFβ1 treatment, but also on the specific presentation of TGFβ1 via its heparin-binding domain and the solid phase presentation of a unique subset of angiogenic factors. Furthermore, the AcHyA-Heparin component sequestered the secreted paracrine factors to generate a higher localized concentration within the hydrogel.

The AcHyA Hydrogels Enhance CPC Survival and Neovascularization In Vivo

Figure 31:
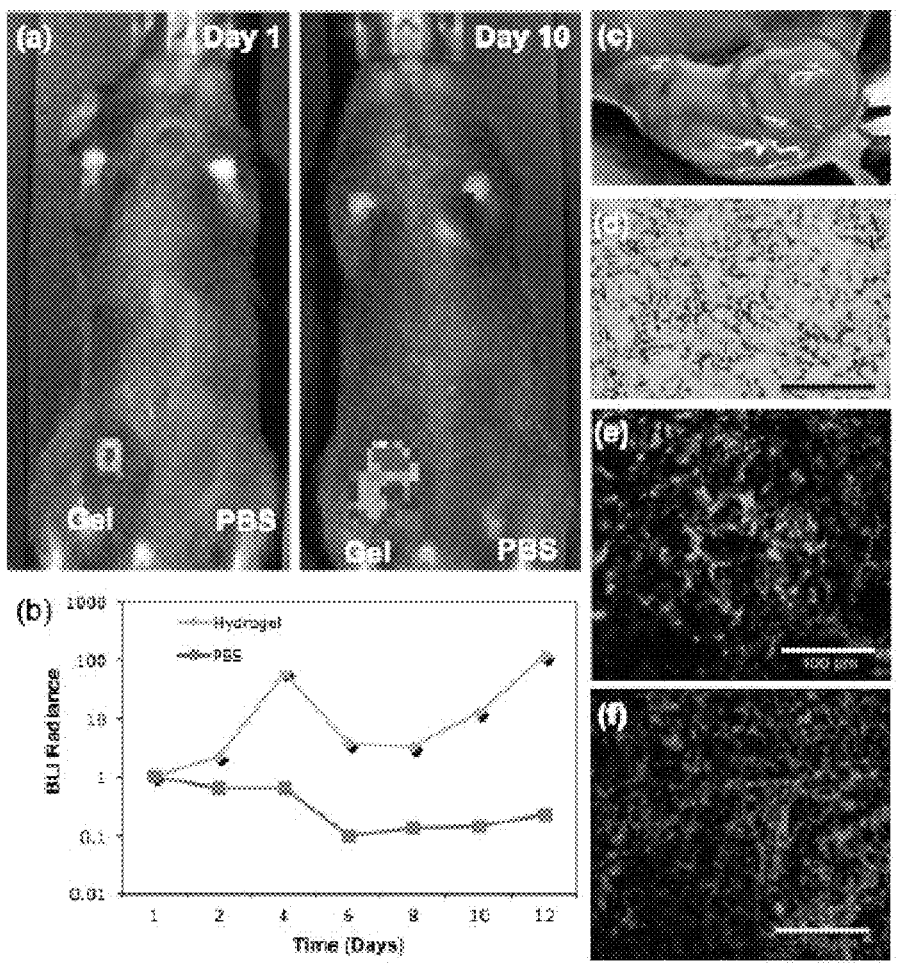
FIG. 31: HyA-PHT hydrogels promoted CPC survival and neovascular function in vivo. (a) 1d post-implantation of GFP-rLuc-mCPCs (~500,000) into syngenic mouse hindlimbs, the cells transplanted using PBS were not bright enough to be visualized on the same BLI scale as implants. The population of cells transplanted using the HyA-PHT hydrogels increased over 12d. (b) Radiance generated by the transplanted CPCs over 12 days (n=5, normalized to day 1) demonstrated that the hydrogels promoted cell survival and prevented detrimental cell diffusion in vivo (which could be responsible for the miniscule signal from the PBS delivered cells). (c-f) The transplanted hydrogels were infiltrated by host cells and recruited a host vascular network (non-GFP expressing), in addition to one developed by the seeded CPCs. (d) Masson's trichrome staining of excised transplants after 12 days demonstrated high cellular density, ECM production, and negligible inflammatory cells or inflammation. (e) Verification of the persistence of donor mCPCs with GFP expression, where (f) many of these cells expressed CD31, suggesting that they had undergone vascular differentiation. Scale bars=100 μm.

The in vivo performance of the hydrogels was evaluated using a subcutaneous implantation model in syngenic C57BL/6 mice. For this experiment, the CPCs were stably transduced with the gene for renilla luciferase (rLuc) under transcriptional control by human ubiquitin promoter to induce constitutive expression. CPCs (~500,000) were entrained within 100 µL of the HyA-PHT hydrogel into and injected into murine hindlimbs. As a control, an equal number of CPCs were suspended in vehicle saline and injected into the contralateral limb. Over the next 12 days, the rLuc reporter was used to measure CPC survival non-invasively with in vivo bioluminescent (BLI) imaging (FIG. 31a). The CPCs entrained in the HyA-PHT hydrogel experienced a peak of BLI signal after 4 days followed by a steady increase in BLI signal from day 6 to day 12 (FIG. 31b). The early increase in BLI signal was anticipated due to activity that is likely to occur on the ubiquitin promoter as the CPCs recover from initial proteotoxic stresses encountered by the CPCs following in vivo implantation. An overall smaller BLI signal was detected from the control CPCs in saline, indicating that fewer cells survived the transplantation procedure, and a drop on BLI signal detected between days 4 and 6 never recovered. Based on these data, the HyA-PHT hydrogel-based MACT maintained the CPCs at the implantation site, helped them overcome the stresses associated with transplantation, and supported their proliferation in vivo.

After 12 days, mice were sacrificed and the transplanted regions were inspected. There was no discernible evidence of CPC transplantation in the limbs where we had injected the saline controls. In the limbs injected with HyA-PHT, a well-defined subcutaneous nodule could be observed at the site of transplantation. When the limbs were dissected, the hydrogel was easily identified in the subcutaneous tissue, and it was evident that the transplants had become integrated with the host vasculature (FIG. 31c). The hydrogel transplants were recovered with the adjacent tissue for analysis with immunohistochemistry. The hydrogels exhibited a high cellular density, and many of the entrained cells were GFP+ (FIG. 31d), indicating that they were derived from the GFP+ CPCs. However, approximately 18% of the cells were not expressing GFP, which suggest that the HyA-PHT hydrogels were conductive to the host cells. Endothelial cell differentiation was also verified in the hydrogel implants, as approximately 93% of the cells were positive for CD31+ (FIG. 31e). Interestingly approximately 5% of the CD31+ cells were negative for GFP, and thus it is likely that these were endothelial cells recruited from the host vasculature. Finally, extracellular matrix production was evaluated within and around the implants using hematoxylin and eosin (FIG. 31f) and Masson's trichrome stain (FIG. 31g). There was evidence of collagen development inside the hydrogel, suggesting that the cells were remodeling the hydrogel and depositing their own extracellular matrix. Collectively these observations show that the HyA-PHT implant encouraged neovascularization and integration with the host tissue, and its effects were mediated on both the transplanted CPCs and the neighboring host cells.

Discussion

The above results demonstrate how a suitable biomaterial can support donor cell survival during transplantation and encourage integration into the host tissue. We employed a tunable method of HyA hydrogel synthesis that enabled independent control over both the concentration of functionalized hydrogel components and the mechanical properties of the resulting matrix. First, we determined the role of each hydrogel component to promote survival and adhesion of CPCs, a population of Sca-1+CD45− cells that contributes to regeneration and revascularization of cardiac tissues. We further determined that the proliferation of entrained CPCs was dependent on both HyA hydrogel stiffness and bspRGD (15) adhesion peptide density. Next, we verified that the HyA hydrogels would promote CPC differentiation to endothelial cells and subsequent formation of a tubular endothelial network via a TGFβ1-dependent mechanism. Furthermore, we demonstrated that addition of heparin in the HyA hydrogels also coordinates the presentation of TGFβ1 and supports the trophic function of the CPCs by sequestering secreted angiogenic factors. Finally, we demonstrated that the HyA hydrogels promoted CPC survival when implanted into murine hindlimbs and appeared to encourage their participation in the neovascular response to integrating the implant with the adjacent vasculature and tissues.

In this study, a tunable approach to hydrogel synthesis enabled a comprehensive investigation into the bioinspired HyA hydrogel properties that enhance donor cell function for MACT. The combinatorial method of synthesis enabled independent control of the hydrogel mechanical properties and biological features, including: (1) the density of peptide sequences for cell attachment via binding of integrin receptors; (2) the degradation kinetics; and, (3) sequestration via conjugated heparin of endogenously synthesized or exogenously added growth factors. While synthetic hydrogel matrices have been proposed for this clinical use, they have been synthesized using methods in which crosslinking molecules are necessarily put in competition with other biological agents for binding sites on the biopolymers. As a result, their mechanical properties are inversely dependent on the density of conjugated molecules used to functionalize the material. This dependency limits the utility of these hydrogels to direct the function of implanted cells, as it has recently become clear that matrix stiffness can affect cell fate determination and should be a critical design feature included in cell transplantation systems. By contrast, the mechanical properties of the hydrogel system developed in this work are dependent on both total weight percentage of HyA and the concentration of peptide crosslinkers, but independent of the biological features that are incorporated on the other AcHyA hydrogel components. With this approach it was also possible to overcome limitations reported for MACT systems, such as: (1) compromised crosslinking efficiencies due to competition between macromer chains and other bioactive moieties in the hydrogel network; (2) unreacted bioactive ligands entrained in the material acting as antagonists; and, (3) low molecular weight macromers rapidly degraded by the entrained cells.

Given our tunable method of HyA hydrogel synthesis, it was possible to examine a wide range of experimental parameters. Significantly, the material design space was not constrained by any dependencies between the hydrogel components, and therefore we could evaluate HyA-hydrogel based on first-principles of cell-material interactions without limitations imposed by the method of synthesis. To facilitate our investigation, response surface methodology (RSM) was employed using a previously validated experimental design, which allowed an efficient exploration of the effects of matrix mechanics (i.e., complex shear moduli, $G^*$, as a function of HyA weight percentage), integrin-engaging peptide concentration, and growth factor presentation on the proliferation, differentiation and neovascular function of CPCs that were entrained in these materials. This RSM analysis was augmented by additional experiments designed to investigate the TGFβ1-dependent effects of CPCs and to verify that they had differentiated into functional ECs. Finally, all of the in vitro findings were validated using an in vivo model, thus demonstrating that the outcomes of the RSM analyses were applicable once the material was implanted into a host tissue.

The covalently conjugated heparin in the HyA hydrogels made a significant contribution to the performance of this material. In addition to sequestering growth factors via their heparin-binding domain, this component also presented these growth factors in active forms. The presentation of the TGFβ1 by heparin substantially facilitates capillary tube formation, as an equimolar concentration of TGFβ1 supplied as a soluble mediator in HyA-hydrogels lacking heparin was insufficient to generate a similar neovascular response, as measured by either by the paracrine production of angiogenic growth factors (FIG. 30) or by direct induction of tubulogenesis (FIG. 27). When TGFβ1 is released from a matrix, it acts on the host tissues by modulating the extracellular matrix produced by the endogenous cells to the attenuate the fibrotic response. It is interesting to further note that the factor sequestering capacity of heparin will enable the bioinspired matrix to become enriched with endogenously produced angiogenic factors over time, which continued to promote their biological function.

Although the overall approach in this study was focused on CPC transplantation, these HyA hydrogels were designed for easy adaptation for other cell types and therapeutic applications. Significantly, we demonstrated that addition of heparin in the HyA hydrogels was necessary to coordinate the presentation of TGFβ1 and to support the trophic functions of the CPCs by sequestering multiple secreted angiogenic factors within the matrix. These sequestered growth factors were presented by the crosslinked polymer (i.e., solid phase), thereby enhancing their effectiveness in the hydrogel. In vivo these HyA hydrogels supported survival, proliferation, and engraftment of the transplanted CPCs. Additionally, they promoted an enhanced angiogenic response from both the transplanted and host cells. Integration of transplanted cells with a host vasculature is nearly a universal challenge following cell transplantation, and thus these HyA hydrogels have immense promise in a variety of MACT applications. Given the wide range of biological and mechanical parameters for these HyA hydrogels, it will be possible to engineer a matrix that promotes additional specific functions of donor cells to enhance their therapeutic potential. Therefore, we anticipate these biomaterials will be an enabling technology to improve the clinical outcomes for cell translation therapies.

Materials and Methods

Figure 18:
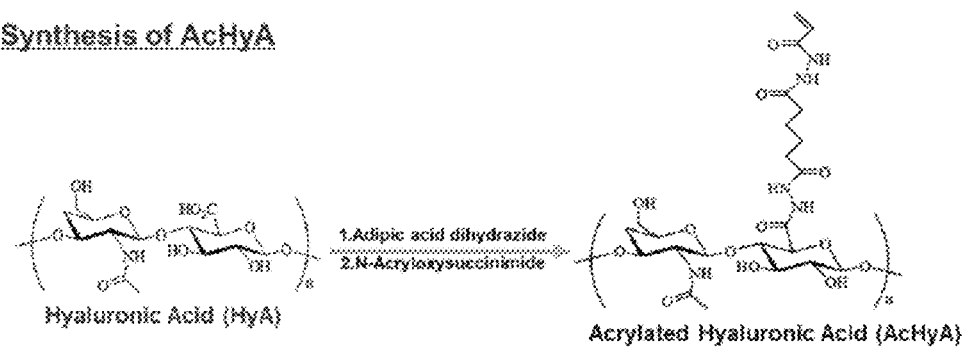
FIG. 18: Chemical Synthesis. (a) Synthesis of acrylated hyaluronic acid by sequential conjugation of adipic acid dihydrazide and N-acryloxysuccinimide. (b) Synthesis of thiolated heparin by carbodiimide conjugation with cysteamine and subsequent reduction using TCEP.
Figure 18:
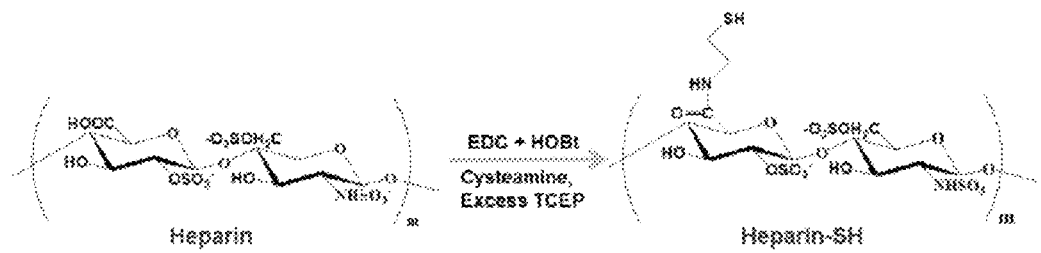
Figure 21:
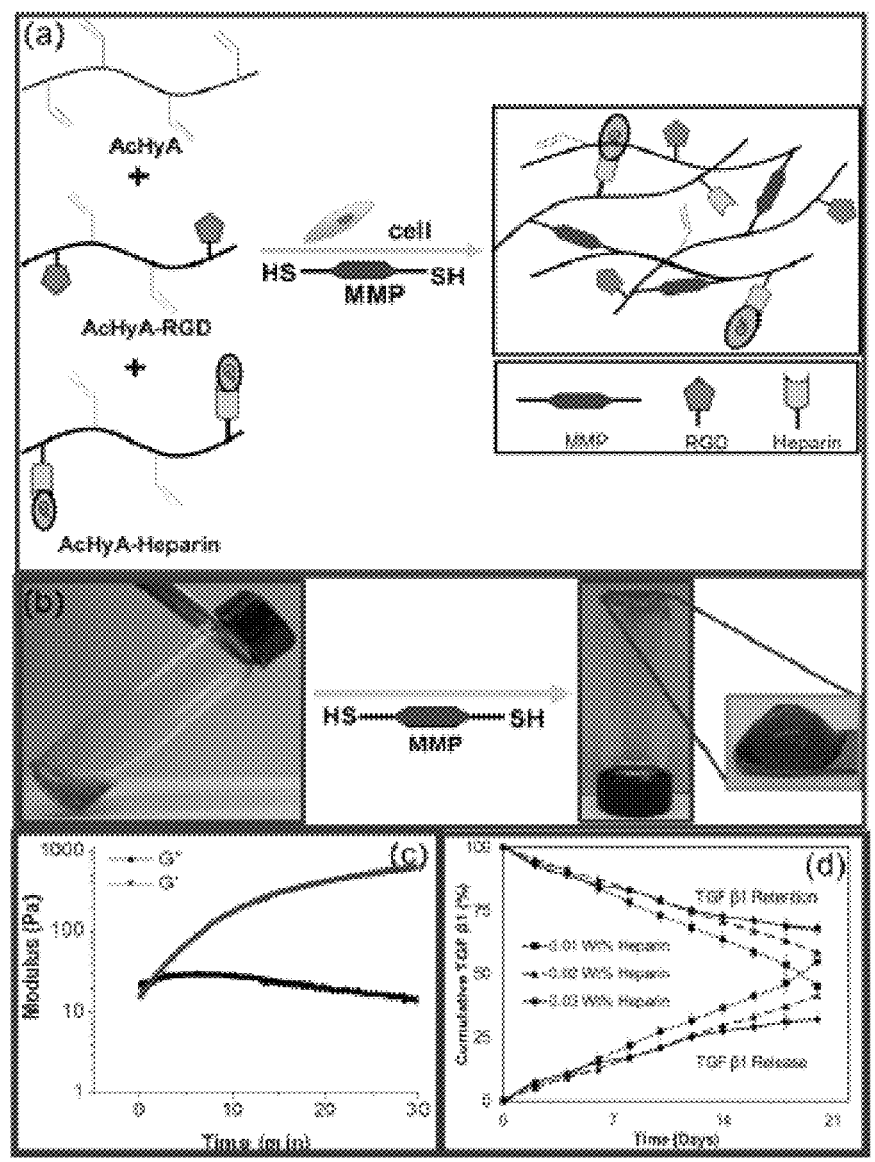
FIG. 21: Schematic for gel synthesis. (a) HyA hydrogels containing the cell adhesive bspRGD(15) peptide and heparin as a growth factor presenting/releasing agent were synthesized by using (b) bis-cysteine enzymatically-degradable peptide crosslinkers that reacted via the Michael-type addition to acryl groups on the functionalized HyA precursors. (c) The time required to initiate gelation, defined when the storage modulus (G') exceeds the loss modulus (G") occurred within 60 seconds. Gelation was considered complete when G' reached a plateau, and occurred within 15 minutes, depending on the weight ratio of HyA included in each hydrogel. (d) Depending on the weight percentage of heparin present, HyA hydrogels (0.03 wt. %) retain over 70% of the TGFβ1 for up to 20 days.
Figure 22:
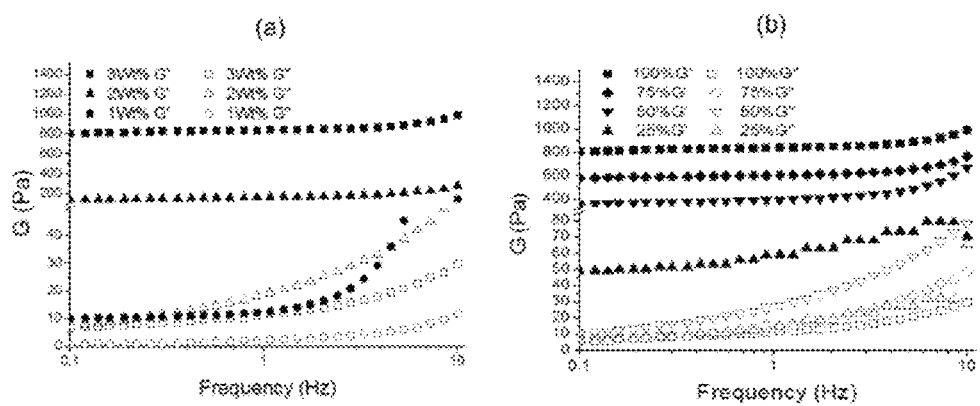
FIG. 22: Dynamic rheological properties of HyA hydrogels. Rheological properties of the hydrogel were determined (a) at various weight percentages HyA with constant crosslinking density (100% crosslinking density) and (b) at the various crosslinking densities (defined as moles of thiol on the peptide cross linker compared to moles of acrylate groups on AcHyA) with constant weight percentage (3 wt %) of the hydrogel. The filled symbol represents the storage modulus, and the open symbol represents the loss modulus. Three repeating measurements were performed on each sample.

Synthesis of HyA Hydrogels:

HyA-based hydrogels were prepared from AcHyA components as shown in the FIG. 21. A detailed description of the materials and methods used to synthesize the AcHyA hydrogel components is shown in FIGS. 18 and 19. AcHyA, AcHyA-RGD, and heparin-SH were dissolved at various ratios in 0.3 mL of triethanolamine-buffer (TEOA buffer; 0.3 M, pH 8) and incubated for 15 minutes at 37° C. Then, HyA hydrogels were generated by in situ crosslinking of the HyA precursors with the MMP-13-17 cleavable peptide sequence CQPQGLAKC (SEQ ID NO:8) (50 μL TEOA buffer), which could react with any free acrylate groups on the AcHyA chains.

Hyaluronic acid (HA, sodium salt, 1.0 MDa and 500 kDa) was obtained from Lifecore Biomedical (Chaska, Minn.). Adipic dihydrazide (ADH), 1-ethyl-3-[3-(dimethylamino) propyl]carbodiimide (EDC), sodium hydroxide (NaOH), hydrochloric acid (HCl) and 1-hydroxybenzotriazole (HOBt) were purchased from Aldrich (Milwaukee, Wis.). Dimethyl sulfoxide (DMSO), N-Acryloxysuccinimide (NAS), acetone, ethanol were obtained from Fisher Scientific (Waltham, Mass.). Paraformaldehyde (16% in H2O) was obtained from Electron Microscopy Sciences (Hartfield, Pa.). Calcein was purchased from BD Biosciences (Pasadena, Calif.). The linker peptide (CQPQGLAKC; SEQ ID NO:8) containing the 15 amino-acid bspRGD(15) adhesion peptide (CGGNGEPRGDTYRAY; SEQ ID NO:1) were synthesized by American Peptide (Sunnyvale, Calif.). Dialysis membranes (10000 MWCO, SpectraPor Biotech CE) were purchased from Spectrum Laboratories (Rancho Dominguez, Calif.). All chemicals were used as received. All cell culture reagents were purchased from Invitrogen (Carlsbad, Calif.). 1× Dulbecco's phosphate buffered saline (DPBS) was purchased from Invitrogen.

Rheological Characterization:

Viscoelastic properties of the hydrogel were determined using an oscillatory rheometer (MCR300, Anton Paar, Ashland, Va.) with 25 mm parallel plates and a gap height of 0.5 mm at 37 C. The sample was prevented from drying out by performing the analysis in a humidity-controlled chamber. The viscoelastic properties of the hydrogel were determined at frequencies ranging from 0.001-10 Hz at 5% strain.

Incorporation of TGF-b1 and Measurement of Release Kinetics:

Hydrogel macromers of AcHyA, AcHyA-RGD, and heparin-SH were dissolved at various ratios in 0.3 mL of triethanolamine-buffer (TEOA; 0.3 M, pH 8) and incubated for 15 minutes at 37° C. Then, TGFβ1 (350 ng, PeproTech Inc., Rocky Hill, N.J.) was mixed in the solution of HyA derivatives and incubated for another 15 min at 37° C. To determine the release kinetics, TGFβ1 containing HyA hydrogels were transferred to cell culture inserts (Millipore Corporation, Billerica, Minn.) and TGFβ1 was allowed to release into 400 μL of cell culture media per well. At predetermined time points over the course of 3 weeks, the supernatant was withdrawn and fresh media was replenished, and the mass of TGFβ1 in each supernatant was determined with sandwich ELISA kits (RayBiotech, Inc, Norcross Ga.).

Cell Culture:

The GFP+/Sca-1+/CD45− CPCs were isolated and cultured as previously described. Briefly, GFP+/Sca-1+/CD45− CPCs were cultured in Iscove's Modified Dulbecco's Medium (IMDM) basal media (Life Technologies, Grand Island, N.Y.) containing 10% Fetal bovine serum (FBS) and 1% Penicillin-Streptomycin (PS). The CPCs were seeded at an initial density of at 3000 cells/cm$^2$, and the culture medium was replaced every 2-3 days. Once the culture reached 80-90% confluency, subculture was performed using 0.05% Trypsin-EDTA (Life Technologies, Grand Island, N.Y.) diluted 1:5 in 1×DPBS (Life Technologies, Grand Island, N.Y.) for 5 minutes at 37 C. For cell encapsulation in the HyA hydrogels, confluent cells were trypsinized, collected into a pellet by centrifugation and resuspended in the uncrosslinked AcHyA macromer at a density of 5×10$^6$ cells/mL. Then, the peptide crosslinker was mixed into the HyA-cell suspension and transferred into cell culture inserts. Before adding the cell culture media, cell-gel constructs were incubated for 30 minutes at 37° C. to allow sufficient crosslinking to occur for gelation. The cell-seeded hydrogels were incubated for up to 28 days and the medium was replaced every two days.

Cell Viability, Adhesion and Proliferation:

Cell viability in the hydrogel was assessed by a Live/Dead staining kit (Invitrogen). Prior to imaging, the cells were incubated with propidium iodide (1:2000 in DPBS) and calcein (1:1000 in DPBS) for 5 min at room temperature. Cell adhesion was evaluated on the basis of actin cytoskeletal staining to assess cell spreading. The hydrogels were washed three times with PBS, and cells were fixed with 4% paraformaldehyde solution at room temperature for 30 min. Then, samples were incubated with rhodamine-labeled phalloidin (1:200) in the dark for 2 h at room temperature. Prior to imaging, cell nuclei were stained with DAPI (1:1000) for 5 min at room temperature. After washing with PBS, confocal images were acquired using two-photon confocal microscope (Prairie Technologies, Middleton, Wis.). Cell proliferation inside the hydrogels was quantified using the Alamar blue assay. Cell-gel constructs were incubated with medium containing 10% Alamar blue for 12 h, and then the absorbance of the medium from each sample was analyzed at 570 nm using a spectrophotometer (Molecular Devices).

Immunocytochemistry:

Hydrogel samples were fixed using 4% (v/v) paraformaldehyde in DPBS at 37° C. for 60 min. Samples were then rinsed 3 times in PBS and kept at 4° C. The cells were permeabilized with 0.1% Triton X-100 for 5 min, blocked by 3% BSA for 1 hr, and then incubated overnight at 4° C. with a 1:200 dilution of primary antibody (rabbit anti-CD31 IgG, Abcam; rabbit anti-α-actinin IgG, Abcam; rabbit anti-troponin I IgG, Abcam; rabbit anti-troponin T IgG, Abcam; rabbit anti-Smooth muscle actin IgG, Abcam). After washing the cells 3× with PBS, they were incubated with a 1:250 dilution of goat anti-rabbit AlexaFluor Texas red IgG (Invitrogen, Molecular Probes) for 2 h at RT. Prior to imaging, cell nuclei were stained DAPI for 5 min at RT. Cell-gel constructs were visualized using a two-photon confocal microscope Flow Cytometry:

Cells entrained with the hydrogels were fixed with 4% paraformaldehyde for 30 min and permeabilized with 0.1% Triton for 5 min. After blocking with Fc-blocker for 10 min, the cells were stained with R-phycoerythrin (PE)-conjugated anti-CD31 (PECAM-1) antibody or R-phycoerythrin (PE)-conjugated anti-CD144 (VE-cadherin) antibody at 1:100 dilution for 1 hr in dark. The hydrogels were then degraded by incubating them with 100 unit/mL hyaluronidase for 4 hr to release the encapsulated cells. The stained cells were then pelleted by centrifugation, rinsed twice in PBS, passed through a 36-µm mesh cell strainer, and analyzed using a FC500 FACS Vantage cell sorter (BD Biosciences; see FIG. 25 for gating information).

Mouse Angiogenesis Protein Profiler Assay:

The synthesis of endogenous vascularization-associated proteins by the CPCs were measured using a mouse angiogenesis protein profiler array (R&D Systems, Minneapolis, Minn.) following the manufacturer's instructions. In these experiments, an additional control was included consisting of HyA-P with soluble TGFβ1 at an equivalent concentration as the HyA-PHT hydrogels. The array was visualized by a chemiluminescence substrate using Bio-Rad ChemiDoc XRS System. The relative expression of the angiogenesis proteins that were produced by the CPCs in each of the hydrogels was measured by comparing the pixel density of each chemiluminescence image.

In Vivo Implantation Study:

To evaluate performance of the HyA hydrogels to promote CPC survival and to direct cell fate in vivo, we used a murine hind-limb injection model in syngenic C57BL/6 mice. To establish an in vivo reporter for CPC survival, we transduced the cells with a renilla luciferase (rLuc) gene under the control of a human ubiquitin promotor element using a lentiviral transduction system. The rLuc+ CPCs (5 million cells/mL) were suspended in HyA hydrogel macromers and then the peptide crosslinker was mixed into the suspension immediately prior to transplantation. The CPC/hydrogel suspension (100 µL) was injected into the subcutaneous tissues adjacent to the gastrocnemius muscle of the right hind limb. Gelation was allowed to occur in situ. An equivalent volume of PBS was used as a vehicle control for CPCs transplantation in the left leg of each mouse. Beginning 24 hours after the CPC transplantations, and continuing every 48 hours thereafter, in vivo bioluminescence imaging (BLI) was performed to assess cell survival and proliferation. Ten minutes prior to imaging, each mouse received 100 µL of coelenterazine (Promega, Madison, Wis. 1 mg/mL in PBS with 0.1% BSA) by intraperitoneal injection. BLI images were taken using a Spectrum IVIS (Perkin Elmer), and three images were obtained over a period of 30 minutes to ensure the steady-state bioluminescence had been obtained. Cell proliferation at each time point was assessed on the basis of radiance (p/s/cm2/SR) in each of the hind-limb regions of interest.

After 12 days, the mice were sacrificed and the hydrogel implants were harvested. Prior to dissection of the hind limbs, we accessed the heart via bilateral thoracotomy for intraventricular perfusion of the mouse with PBS using a syringe pump for approximately 5 minutes. Immediately following, we harvested the implanted hydrogel with the surrounding tissues and fixed the specimen with 4% PFA in buffered saline. After fixation, half of each specimen was cryopreserved with a 30% sucrose solution and suspended in OCT medium for cryosectioning. These sections were stained using either hematoxylin and eosin or Masson's trichrome. The other half of each section was stained for CD31 using the methods described above and imaged immediately using two-photon confocal microscopy.

Statistical Analysis:

All data are presented as means with error bars of the standard deviation, unless otherwise noted. We used oneway ANOVA for all statistical tests with post-hoc Tukey multiple comparison analysis.

Although the presently described compositions and methods have been described in some detail by way of illustration and example for purposes of clarity of understanding, one of skill in the art will appreciate that certain changes and modifications may be practiced within the scope of the appended claims. In addition, each reference, website, accession number, etc. is incorporated by reference in its entirety.

What is claimed is:

1. A method of performing matrix-assisted cell transplantation (MACT) comprising:
   contacting mammalian cells with matrix components comprising macromers and a crosslinker, wherein the crosslinker comprises a peptide that comprises CQPQGLAKC (SEQ ID NO:8); and
   administering the matrix components and cells to a mammalian subject to allow for in situ crosslinking of the matrix components thereby forming a matrix within the mammalian subject.

2. The method of claim 1, wherein the administering comprises injection.

3. The method of claim 1, wherein the matrix is conjugated to cysteine-terminating peptides.

4. The method of claim 1, wherein the mammalian subject has an injured heart.

5. The method of claim 4, wherein the administering is to the injured heart.

6. The method of claim 1, wherein the mammalian subject has an infarcted heart.

7. The method of claim 6, wherein the administering is to the infarcted heart.

8. The method of claim 1, wherein the mammalian subject has an ischemic heart.

9. The method of claim 8, wherein the administering is to the ischemic heart.

10. The method of claim 1, wherein the mammalian subject has damaged blood vessels.

11. The method of claim 10, wherein the administering is to the site of the damaged blood vessels.

12. The method of claim 1, wherein the mammalian subject is a human subject.

13. The method of claim 1, wherein the cells are autologous to the subject.

14. The method of claim 1, wherein the cells are allogeneic to the subject.

15. The method of claim 1, wherein the matrix further comprises a growth factor.

16. The method of claim 1, wherein the matrix and proliferated and differentiated cells further comprise a growth factor or an angiogenesis promoting factor.

17. The method of claim 10, wherein the damaged blood vessels are due to a disease or condition selected from the group consisting of peripheral arterial disease, critical limb ischemia, chronic wounds and stroke.

18. The method of claim 1, wherein the macromers comprise hyaluronic acid (HyA).

19. The method of claim 1, wherein the macromers comprise acrylayted hyaluronic acid (AcHyA).

20. The method of claim 1, wherein the cells are progenitor cells.

21. The method of claim 20, wherein the progenitor cells are Sca-1$^+$CD45$^-$ cells.

22. The method of claim 21, wherein the progenitor cells are obtained from cardiospheres from heart tissue.

23. The method of claim 22, wherein the heart tissue is human heart tissue.

24. The method of claim 20, wherein the progenitor cells are cardiac progenitor cells and at least 3% of the cardiac progenitor cells express Isl1.

25. The method of claim 24, wherein at least 10% of the cardiac progenitor cells express Isl1.

26. The method of claim 20, wherein the progenitor cells express a cell surface marker selected from the group consisting of c-kit, CD31, CD44, CD80, CD90, CD105, CD133, CD34, Sca-1, and CD45.

* * * * *